(12) United States Patent
Alvarez, Jr. et al.

(10) Patent No.: US 10,196,685 B2
(45) Date of Patent: Feb. 5, 2019

(54) METHODS AND SYSTEMS FOR DELIVERING PROCESS GASES TO CRITICAL PROCESS APPLICATIONS

(71) Applicant: RASIRC, INC., San Diego, CA (US)

(72) Inventors: Daniel Alvarez, Jr., Oceanside, CA (US); Jeffrey J. Spiegelman, San Diego, CA (US); Russell J. Holmes, San Diego, CA (US); Edward Heinlein, San Diego, CA (US); Zohreh Shamsi, San Diego, CA (US); Christopher Ramos, Bonita, CA (US); Alex Deptala, Spring Valley, CA (US); James Hogan, Coronado, CA (US)

(73) Assignee: RASIRC, Inc., San Diego, CA (US)

( * ) Notice: Subject to any disclaimer, the term of this patent is extended or adjusted under 35 U.S.C. 154(b) by 71 days.

(21) Appl. No.: 15/310,775

(22) PCT Filed: May 12, 2015

(86) PCT No.: PCT/US2015/030422
§ 371 (c)(1),
(2) Date: Nov. 13, 2016

(87) PCT Pub. No.: WO2015/175564
PCT Pub. Date: Nov. 19, 2015

(65) Prior Publication Data
US 2017/0072081 A1    Mar. 16, 2017

Related U.S. Application Data

(60) Provisional application No. 61/992,806, filed on May 13, 2014, provisional application No. 62/027,562, (Continued)

(51) Int. Cl.
*A61L 2/00* (2006.01)
*A61L 9/00* (2006.01)
(Continued)

(52) U.S. Cl.
CPC ............ *C12Q 1/6848* (2013.01); *A61L 2/186* (2013.01); *A61L 2/208* (2013.01); *C12Q 1/6806* (2013.01); *A61L 2202/24* (2013.01)

(58) Field of Classification Search
CPC ..... A61L 2/208; C12Q 1/6848; B01D 53/228; F22B 1/284; C01B 21/16
(Continued)

(56) References Cited

U.S. PATENT DOCUMENTS 2,178,496 A    10/1939  Schmidt
2,193,622 A    3/1940   Coulter
(Continued)

FOREIGN PATENT DOCUMENTS

CN    101966981 A    2/2011
EP    0302420 B1     6/1992
(Continued)

OTHER PUBLICATIONS

Schumb, et al. "Hydrogen Peroxide" Reinhold Publishing Corporation; 1955; New York; AATA No. 15-938; Chapter 5.
(Continued)

*Primary Examiner* — Monzer R Chorbaji
(74) *Attorney, Agent, or Firm* — Wagenknecht IP Law Group PC

(57) ABSTRACT

Methods and delivery systems for providing a gas phase of a multi-component liquid source for delivery to a critical process application are provided. The methods include concentration of a component of the liquid source which is less volatile than water for delivery of a gas stream comprising the less volatile component to a critical process application. Critical process applications include decontamination and microelectronic processing applications.

27 Claims, 34 Drawing Sheets

Related U.S. Application Data filed on Jul. 22, 2014, provisional application No. 62/058,987, filed on Oct. 2, 2014.

(51) Int. Cl.
| | |
|---|---|
| *B01D 47/02* | (2006.01) |
| *C12Q 1/6848* | (2018.01) |
| *A61L 2/20* | (2006.01) |
| *C12Q 1/6806* | (2018.01) |
| *A61L 2/18* | (2006.01) |

(58) Field of Classification Search
USPC .................. 422/1, 28, 292, 305–306; 261/76
See application file for complete search history.

(56) References Cited

U.S. PATENT DOCUMENTS

| | | |
|---|---|---|
| 2,741,584 A | 4/1956 | Holmes et al. |
| 3,205,934 A | 9/1965 | Vincent et al. |
| 3,750,735 A | 8/1973 | Chiang et al. |
| 3,952,089 A | 4/1976 | Kabisch et al. |
| 4,169,123 A | 9/1979 | Moore et al. |
| 4,169,124 A | 9/1979 | Forstrom et al. |
| 4,564,514 A | 1/1986 | Drauz et al. |
| 4,806,245 A | 2/1989 | Boeddekker |
| 4,826,681 A | 5/1989 | Jacquet et al. |
| 4,863,688 A | 9/1989 | Schmidt et al. |
| 5,013,436 A | 5/1991 | Lee et al. |
| 5,418,149 A | 5/1995 | Gelfand et al. |
| 5,612,200 A | 3/1997 | Dattagupta et al. |
| 5,649,996 A | 7/1997 | Softer et al. |
| 5,667,753 A | 9/1997 | Jacobs et al. |
| 5,674,450 A | 10/1997 | Lin et al. |
| 5,770,739 A | 6/1998 | Lin et al. |
| 5,785,934 A | 7/1998 | Jacobs et al. |
| 5,876,666 A | 3/1999 | Lin et al. |
| 5,910,448 A | 6/1999 | Atwater et al. |
| 5,928,409 A | 7/1999 | Sirkar |
| 6,042,704 A | 3/2000 | Joshi et al. |
| 6,290,820 B1 | 9/2001 | Carden |
| 7,122,166 B2 | 10/2006 | Parrish |
| 7,157,046 B2 | 1/2007 | McVey et al. |
| 7,354,551 B2 | 4/2008 | Mielnik et al. |
| 7,618,027 B2 | 11/2009 | Spiegelman |
| 7,625,015 B2 | 12/2009 | Spiegelman et al. |
| 7,790,104 B2 | 9/2010 | Adams et al. |
| 8,168,122 B2 | 5/2012 | Lee |
| 8,282,708 B2 | 10/2012 | Spiegelman et al. |
| 8,518,150 B2 | 8/2013 | Spiegelman et al. |
| 8,551,399 B2 | 10/2013 | Shannon et al. |
| 8,685,329 B2 | 4/2014 | Lee |
| 8,703,066 B2 | 4/2014 | Vaughn et al. |
| 9,410,191 B2 | 8/2016 | Alvarez, Jr. et al. |
| 9,610,550 B2 | 4/2017 | Alvarez, Jr. et al. |
| 9,932,630 B2 | 4/2018 | Alvarez, Jr. et al. |
| 2002/0114727 A1 | 8/2002 | McVey et al. |
| 2002/0192938 A1 | 12/2002 | Wada et al. |
| 2003/0007916 A1 | 1/2003 | Khorzad et al. |
| 2003/0086820 A1 | 5/2003 | McDonnell et al. |
| 2003/0105356 A1 | 6/2003 | Schiffer et al. |
| 2003/0219957 A1 | 11/2003 | Kuwabara et al. |
| 2004/0079491 A1 | 4/2004 | Harris et al. |
| 2005/0084415 A1 | 4/2005 | McVey et al. |
| 2005/0175500 A1 | 8/2005 | Adams et al. |
| 2005/0193758 A1 | 9/2005 | Wells |
| 2005/0250277 A1 | 11/2005 | Chang et al. |
| 2005/0252856 A1 | 11/2005 | Parrish |
| 2006/0021615 A1 | 2/2006 | Kertzman |
| 2007/0187320 A1 | 8/2007 | Mabuchi et al. |
| 2007/0199891 A1 | 8/2007 | Mabuchi et al. |
| 2008/0199355 A1 | 8/2008 | Berentsveig et al. |
| 2008/0237057 A1 | 10/2008 | Li et al. |
| 2009/0014901 A1 | 1/2009 | Spiegelman |
| 2009/0145831 A1 | 6/2009 | Manabe et al. |
| 2009/0145847 A1 | 6/2009 | Spiegelman et al. |
| 2009/0188863 A1 | 7/2009 | Knapp et al. |
| 2009/0263499 A1 | 10/2009 | Platt, Jr. et al. |
| 2010/0024816 A1 | 2/2010 | Weinstein et al. |
| 2010/0034697 A1 | 2/2010 | Weinberger et al. |
| 2010/0117246 A1 | 5/2010 | Sarigiannis et al. |
| 2010/0275629 A1 | 11/2010 | Erickson |
| 2011/0076192 A1 | 3/2011 | Robitaille et al. |
| 2011/0183598 A1 | 7/2011 | Holt |
| 2011/0186495 A1 | 8/2011 | Robinson et al. |
| 2012/0095178 A1 | 4/2012 | Pressel et al. |
| 2013/0199220 A1 | 8/2013 | Ma et al. |
| 2013/0204549 A1 | 8/2013 | Saito et al. |
| 2013/0233170 A1 | 9/2013 | Spiegelman et al. |
| 2013/0236355 A1 | 9/2013 | Dufresne et al. |
| 2013/0276357 A1 | 10/2013 | Shannon et al. |
| 2013/0302207 A1 | 11/2013 | Ahiska |
| 2014/0014138 A1 | 1/2014 | Spiegelman et al. |
| 2015/0068611 A1 | 3/2015 | Alvarez, Jr. et al. |
| 2015/0190736 A1 | 7/2015 | Alvarez, Jr. et al. |
| 2015/0329901 A1 | 11/2015 | Alvarez, Jr. et al. |
| 2016/0051928 A1 | 2/2016 | Spiegelman et al. |

FOREIGN PATENT DOCUMENTS

| | | | |
|---|---|---|---|
| EP | 0780130 A1 | 6/1997 | |
| EP | 1487503 B1 | 9/2007 | |
| EP | 1473044 B1 | 12/2007 | |
| JP | H02-273518 | 11/1990 | |
| JP | H08-168655 | 7/1996 | |
| JP | H09-089732 | 4/1997 | |
| JP | 2011125788 A | 6/2011 | |
| WO | 1997/015333 A1 | 5/1997 | |
| WO | 2002/0066082 A1 | 8/2002 | |
| WO | 2003/0082355 A1 | 10/2003 | |
| WO | 2005/113428 A1 | 12/2005 | |
| WO | 2006/117328 A1 | 11/2006 | |
| WO | 2007/098351 A2 | 8/2007 | |
| WO | 2008/092203 A1 | 8/2008 | |
| WO | 2009/064427 A3 | 5/2009 | |
| WO | 2012/024131 A2 | 2/2012 | |
| WO | 2013/148262 A1 | 10/2013 | |
| WO | WO 2013/0148262 | * 10/2013 | ............... B01F 3/04 |
| WO | 2014/014511 A1 | 1/2014 | |
| WO | 2014/165637 A2 | 10/2014 | |
| WO | 2015/175564 A1 | 11/2015 | |

OTHER PUBLICATIONS

EP13769881 Euopean Search Report dated Sep. 24, 2015.
EP15792856 European Search Report dated Dec. 22, 2017.
JP2015-503308 Office Action dated Mar. 28, 2017.
PCT/US2013/031519 International Search Report dated Jun. 14, 2013.
PCT/US2015/030422 ISR dated Sep. 21, 2015.

* cited by examiner

METHODS AND SYSTEMS FOR DELIVERING PROCESS GASES TO CRITICAL PROCESS APPLICATIONS

Various process gases may be used in the manufacturing and processing of micro-electronics and other applications such as decontaminating materials contaminated with bacteria, viruses, DNA, and other biological agents as well as other critical process applications. In addition, a variety of chemicals may be used in other critical process applications, including without limitation wafer cleaning, wafer bonding, photolithography mask cleaning, atomic layer deposition, chemical vapor deposition, manufacturing amorphous oxides including annealing of TFT and flat panel displays, disinfection of surfaces, industrial parts cleaning, pharmaceutical manufacturing, production of nano-materials, regenerating fuel cells membranes, and other applications in which process control and purity are critical considerations. In those processes, it is often necessary to deliver very specific amounts of certain process gases under controlled temperature, pressure and flow rate conditions.

There are numerous process gases used in critical process applications. One advantage of using process gases in critical process applications, as opposed to liquid-based approaches, is that gases are able to access high aspect ratio features on a surface. For example, according to the International Technology Roadmap for Semiconductors (ITRS), current semiconductor processes should be compatible with a half-pitch as small as 20-22 nm. At these dimensions, liquid-based chemical processing is not feasible, because the surface tension of the process liquid prevents it from accessing the bottom of deep holes or channels and the corners of high aspect ratio features. In addition, for applications requiring low mass flow for process chemicals, liquid delivery of process chemicals is not accurate or clean enough and process gases have further been used to overcome certain limitations of liquid-based processes, because gases do not suffer from the same surface tension limitations.

Ozone is a gas that is typically used to clean the surface of semiconductors (e.g., photoresist stripping) and as an oxidizing agent (e.g., forming oxide or hydroxide layers). Plasma-based processes have also been employed to overcome certain limitations of liquid-based processes. However, ozone- and plasma-based processes present their own set of limitations, including, inter alia, cost of operation, insufficient process controls, undesired side reactions, and inefficient cleaning. More recently, hydrogen peroxide has been explored as a replacement for ozone in certain applications. However, for several reasons, hydrogen peroxide has been of limited utility. Highly concentrated hydrogen peroxide solutions present serious safety and handling concerns and obtaining high concentrations of hydrogen peroxide in the gas phase has not been possible using existing technology. Similar concerns have limited the feasibility of using other potentially beneficial process gases, such as hydrazine.

Gaseous delivery would be desired from a standpoint of ease of delivery, accuracy and purity. Low vapor pressure liquids, such as water and hydrogen peroxide, are generally not available in the gas phase and, thus, the gas phase must be created in situ from the corresponding liquid. One approach is to vaporize the process chemical component directly at or near the point of use. Vaporizing liquids provides a process that leaves heavy contaminants behind, thus purifying the process chemical. There is an approximately 1000-fold increase in volume when changing from the liquid to the gas phase. Gas flow devices are better attuned to precise control than liquid delivery devices. Additionally, micro-electronics applications and other critical process applications typically have extensive gas handling systems that make gaseous delivery considerably easier than liquid delivery. However, for safety, handling, stability, and/or purity reasons, many process gases are not amenable to direct vaporization from their pure liquid phase.

Gas phase delivery of hydrogen peroxide presents a particularly unique set of problems. One approach is to provide a multi-component liquid source wherein the hydrogen peroxide is mixed with a more volatile solvent, such as water or an organic solvent (e.g., isopropanol). This is particularly suitable for aqueous hydrogen peroxide solutions, as high concentrations of hydrogen peroxide present an explosion hazard. However, when a multi-component solution is the liquid source to be delivered as a gas, such as hydrogen peroxide and water, Raoult's Law for multi-component solutions becomes relevant.

According to Raoult's Law, if a vacuum is pulled on the head space of a multi-component liquid solution or if a traditional bubbler or vaporizer is used to deliver the solution in the gas phase, the more volatile component of the liquid solution will be preferentially removed from the solution as compared to the less volatile component. This limits the concentration of the less volatile component that can be delivered in the gas phase. For instance, if a carrier gas is bubbled through a 30% hydrogen peroxide/water solution at room temperature, only about 295 ppm of hydrogen peroxide will be delivered, the remainder being all water (about 20,000 ppm) and the carrier gas. As a consequence of the preferential loss of water, the hydrogen peroxide concentration in the original liquid source will naturally begin to increase. For vapor pressure and vapor composition studies of various hydrogen peroxide solutions, see Hydrogen Peroxide, Walter C. Schumb, Charles N. Satterfield and Ralph L. Wentworth, Reinhold Publishing Corporation, 1955, New York.

The differential delivery rate that results when a multi-component liquid solution is used as the source of process gases prevents repeatable process control. Process recipes cannot be written around continuously changing mixtures. Controls for measuring a continuously changing ratio of the components of the liquid source are either not readily available, and if available, they are costly and difficult to integrate into the process. In addition, solutions may become hazardous if the relative ratio of the components of the liquid source changes. For example, hydrogen peroxide in water can become explosive at concentrations over about 75%; and thus, delivering hydrogen peroxide by bubbling a dry gas through an aqueous hydrogen peroxide solution, or evacuating the head space above such solution, can take a safe solution (e.g., 30% $H_2O_2/H_2O$) and convert it to a hazardous material that is over 75% hydrogen peroxide. Therefore, currently available delivery devices and methods are insufficient for consistent, precise, and safe delivery of controlled quantities of hydrogen peroxide in the gas phase.

For a variety of applications and processes, it would be advantageous to use gas phase processes based on chemicals that are more typically available as liquid solutions, e.g., organic and inorganic solvents, inorganic and organic acids and bases, and oxidizing agents and reducing agents. Example of such chemicals include, without limitation, hydrogen peroxide, hydrazine, or isopropanol. But the gas phase use of those chemicals has been limited by, inter alia, Raoult's Law, as well as safety, handling, and purity concerns.

With respect to critical process applications which are decontamination applications, the presence of biological or biologically derived materials in certain environments is a recognized problem. For example, materials contaminated with pathogenic microorganisms (e.g., bacteria, fungi, and viruses) present healthcare concerns. In addition to hospital settings, industrial and laboratory environments also suffer from the effects of contamination with biological materials.

For example, in vitro nucleic acid amplification techniques, such as those employed in diagnostic testing, may suffer from carryover amplification where products synthesized in one reaction undesirably enter into a subsequent reaction and serve as templates. Thus, if a product synthesized in one reaction is contaminated with a nucleic acid from a different reaction, then such contamination carryover can result in false-positive test results. Such a false positive would indicate the presence of the contaminant which may lead one to falsely conclude that a particular pathogen was also present.

Various approaches have been developed to minimize the incidence of false-positive results due to carryover contamination. For example, U.S. Pat. No. 5,418,149 discloses an approach whereby a dUTP nucleotide analog is incorporated into DNA amplification products during the polymerase chain reaction (PCR) or other amplification techniques. Unfortunately, the requirement in this technique for an enzyme (uracil-DNA glycosylase) adds to assay complexity, increases costs, and limits application of the technique to treatment of reaction mixtures rather than to whole instruments, surfaces, or enclosed spaces. Liquid bleach (e.g., sodium hypochlorite) was disclosed in U.S. Pat. No. 5,612,200 in a method of destroying the ability of a nucleic acid to serve as a template in in vitro nucleic acid amplification reactions. However, the well-known corrosive effects of bleach on metal components (e.g., stainless steel) renders treatment of certain machinery with ordinary bleach unacceptable. Likewise, inactivation of nucleic acid templates using ultraviolet light cannot effectively decontaminate recesses of instruments that are shadowed by other parts of a mechanical assembly. Other decontamination methods involving exposure to high-energy plasma (see U.S. Pat. No. 5,674,450) may not be appropriate for treatment of delicate machinery that includes sensitive electronics or other components.

With respect to the control of living microorganisms on or in other materials, a number of chemical agents have been used for disinfecting or sterilizing healthcare, industrial, and other environments. Common agents include ethylene oxide, compositions of aldehydes, especially formaldehyde and dialdehyde (e.g., glutaraldehyde). Hydrogen peroxide solutions have also found a use for disinfection.

Hydrogen peroxide is known as a potent non-irritating germicide that has been used as a topical antiseptic, especially in a 3% aqueous solution. Of the known disinfectants and biocidals, hydrogen peroxide appears to have exceptional potential, because the decomposition products, water and oxygen, are not toxic and not harmful to the environment. Also, it tends to have a broad spectrum biocidal activity. Broad spectrum activity is important for instance in situations where harmful organisms are present but their identity is not known. Hydrogen peroxide-based disinfectants are useful in many different applications, including in hospitals, clinics, laboratories, dental offices, home care and chronic care facilities. They may also be used in food and beverage processing and preparation, laboratory environments, animal husbandry, the hospitality industry and for general sanitation modes of transportation such as aircraft, buses, trucks, and cars, surgical equipment, and biological hoods. However, high concentrations of hydrogen peroxide solutions are known to be corrosive to metal and potentially dangerous.

It would be advantageous to use gas-phase hydrogen peroxide to treat microorganisms thus not suffering the drawbacks of solution-based hydrogen peroxide. In addition, gas-phase hydrogen peroxide will be able to reach inaccessible sample surfaces that would otherwise not be available to liquids. Gasses can reach areas that are not directly viewable, or are out of the line of sight. Although vapor-phase hydrogen peroxide is known to have decontamination and sterilization properties (U.S. Pat. Nos. 2,193,622; 4,169,123; 4,169,124 and 4,863,688), the stability of the concentration of the hydrogen peroxide delivered is poor. In part, stable and consistent delivery is hampered by the presence of liquid phase water and/or hydrogen peroxide droplets, or mist or fog in the gas stream.

The gas phase use of hydrogen peroxide has been limited by, inter alia, Raoult's Law, as well as safety, handling, and purity concerns. Therefore, a technique is needed to overcome these limitations and, specifically, to allow the use of highly pure gaseous hydrogen peroxide to be delivered in a consistent, safe, and precise manner so as to be effective in decontaminating or degrading DNA; and in killing microorganisms on surfaces, in foods, in rooms, or in other anti-microbial applications.

To overcome these limitations, methods, systems, and devices are provided wherein a carrier gas at various levels of saturation or no or substantially no saturation is in fluid contact with the gas phase of a multi-component liquid source. The carrier gas may comprise an inert gas and may also comprise an amount of a high volatility component of the liquid source, which is typically water. Using the methods, systems, and devices provided herein the concentration of the high volatility component of the liquid source may be substantially maintained over time.

The methods, systems, and devices provided herein are particularly useful in micro-electronics applications and other critical process applications such as decontamination applications and such applications directed to the microelectronics industry and semiconductors and provide for the safe and controlled transfer and/or purification of low volatility compounds (e.g., hydrogen peroxide or hydrazine) from multi-component liquid solutions (e.g., aqueous hydrogen peroxide or aqueous hydrazine) into a gas in a carrier gas optionally employing a substantially gas-impermeable membrane. In certain embodiments, the low volatility compound is hydrogen peroxide or hydrazine.

SUMMARY

In one aspect of the invention, a method comprising providing a gas phase of a liquid of a multicomponent source comprising a first component and a second component which is less volatile than the first component, and wherein a carrier gas containing the more volatile component as a gas is contacted with the gas phase, is provided. Said contacting results in a gas stream comprising the less volatile component which is delivered to a decontamination application wherein the amount of the more volatile component in the carrier gas is sufficient to keep the ratio of the less volatile component to the more volatile component relatively constant in the liquid source or the gas phase or both. In such aspects, the multicomponent liquid source may be separated from the gas phase with a membrane. Typical membranes are gas-impermeable ion-exchange membranes such as fluorinated ion-exchange membranes or fluorinated ion-exchange membranes prepared as salts. One may further replenish the multicomponent liquid source as it becomes depleted. In many embodiments, the multicomponent liquid source comprises water and hydrogen peroxide wherein water is the more volatile component and hydrogen peroxide the less volatile component.

In a further aspect of the invention, a delivery system for decontamination applications is provided comprising a multicomponent liquid source comprising a first component and a second component which is less volatile than the first component and a gas phase of said source, a carrier gas containing the more volatile component in a gas that is in fluid contact with the gas phase, and an apparatus for delivering a gas stream comprising the less volatile component to a decontamination application such that the amount of the more volatile component in the carrier gas is sufficient to keep the ratio of water and the less volatile component in the liquid source or gas phase or both relatively constant. In such aspects, the multicomponent liquid source may be separated from the gas phase with a membrane. Typical membranes are gas-impermeable ion-exchange membranes such as fluorinated ion-exchange membranes. One may further replenish the multicomponent liquid source as it becomes depleted. In many embodiments, the multicomponent liquid source comprises water and hydrogen peroxide wherein water is the more volatile component and hydrogen peroxide the less volatile component. The apparatus in such delivery systems for delivering a process gas is often an outlet of a head space, which contains the gas phase, connected directly or indirectly to decontamination application, thereby allowing the process gas to flow from the head space to where it will be used.

In another aspect of the invention, a method of delivering hydrogen peroxide gas to a critical process application is provided. The method comprises: (a)
providing a gas phase of an aqueous hydrogen peroxide source that comprises hydrogen peroxide at an initial concentration; (b) contacting the gas phase of the aqueous hydrogen peroxide source with a carrier gas, whereby the concentration of hydrogen peroxide in the aqueous hydrogen peroxide source increases to a second concentration that is higher than the initial concentration; (c) adding to the aqueous hydrogen peroxide source, while step (b) is occurring, an aqueous hydrogen peroxide solution comprising hydrogen peroxide at a third concentration that is lower than the second concentration; (d) withdrawing, after step (c) has begun, a gas stream comprising the resulting combined gas phase of the aqueous hydrogen peroxide source and the carrier gas at a stable steady-state concentration of hydrogen peroxide; and (e) delivering the gas stream to the critical process application.

In another aspect of the invention, a hydrogen peroxide delivery device for a critical process application is provided. Such a device comprises (a) an aqueous hydrogen peroxide source and a gas phase provided by the aqueous hydrogen peroxide source, wherein the aqueous hydrogen peroxide source comprises hydrogen peroxide at an initial concentration, and wherein the gas phase comprises hydrogen peroxide and water; (b) a carrier gas in fluid contact with the gas phase, whereby a hydrogen peroxide gas stream is formed, and whereby formation of the hydrogen peroxide gas stream the concentration of hydrogen peroxide in the aqueous hydrogen peroxide source increases to a second concentration that is higher than the initial concentration; (c) a fill tube that replenishes the aqueous hydrogen peroxide source using an aqueous hydrogen peroxide solution comprising hydrogen peroxide at a third concentration that is lower than the second concentration; and (d) an apparatus that delivers the hydrogen peroxide gas stream to the critical process application, wherein the delivered hydrogen peroxide gas stream comprises hydrogen peroxide at a stable steady-state concentration.

In another aspect of the invention, a method is provided comprising: (a) providing a multi-component liquid source having a gas phase optionally separated from the liquid source by a membrane wherein one component is water; (b) contacting a carrier gas with the gas phase, wherein the carrier gas comprises a carrier gas, such as an inert gas, and may further comprise water, wherein the gas is undersaturated with respect to water; and (c) delivering a stable steady-state gas stream comprising the low volatility compound to a critical process application.

In a further aspect of the invention, a method is provided comprising providing a gas phase of a multi-component liquid source wherein the liquid comprises a component less volatile than water and water, and wherein the component less volatile than water has an initial concentration; contacting an undersaturated carrier gas with the gas phase, wherein the carrier gas comprises a carrier gas and optionally water such that the concentration of the component less volatile than water in the multi-component liquid source increases to a relatively constant higher second concentration; delivering further amounts of a multi-component liquid solution— including the component less volatile than water at a third concentration—to the multicomponent liquid source such that the volume of the multi-component liquid source remains relatively constant or is changed to a volume that is kept relatively constant; and delivering a stable steady-state concentration gas stream comprising water and the component less volatile than water to a critical process application.

In a further aspect of the invention, a method is provided comprising providing a gas phase of a multi-component liquid source wherein the liquid comprises a component less volatile than water, and water and wherein the component less volatile than water has an initial concentration; contacting a carrier gas with the gas phase, wherein the carrier gas comprises a dry or substantially dry carrier gas; replenishing the multicomponent liquid source; and delivering a substantially stable steady-state concentration gas stream comprising water and the component less volatile than water to a critical process application.

In yet another aspect of the invention, a method comprising providing a gas phase of a multi-component liquid source, wherein the liquid source comprises water and a component less volatile than water; contacting the gas phase of the liquid source with a dry or substantially dry carrier gas so as to increase the concentration of the less volatile component in the multi-component liquid source; withdrawing a gas stream comprising the resulting combined gas phase of the liquid source and substantially dry carrier gas at a substantially stable steady-state concentration of the less volatile component; and replenishing the liquid source to maintain it at a relatively constant volume, or to change it to a volume that is kept relatively constant. In such aspects of the invention, the withdrawn gas stream may be delivered to a critical process application.

In a further aspect of the invention, a method comprising contacting the gas phase of an aqueous hydrogen peroxide solution with a substantially dry carrier gas or undersaturated carrier gas and replenishing the hydrogen peroxide solution so as to deliver hydrogen peroxide in the gas phase at a steady-state concentration of hydrogen peroxide in the gas phase that is stable to within 5% of the steady-state concentration average is provided. In such aspects of the invention, the withdrawn gas stream may be delivered to a critical process application.

In another aspect of the invention, a method comprising providing a gas phase of a multi-component liquid source, wherein the liquid source comprises water and a component less volatile than water; contacting the gas phase of the liquid source with a pre-loaded carrier gas that is undersaturated with respect to water so as to increase the concentration of the less volatile component in the multi-component liquid source; modifying the amount of water in the pre-loaded carrier gas to maintain a relatively stable increased concentration of the less volatile component in the liquid source; withdrawing a gas stream comprising the resulting combined gas phase of the liquid source and pre-loaded carrier gas; and replenishing the liquid source to maintain it at a relatively constant volume or is changed to a volume that is kept relatively constant. In such aspects of the invention, the withdrawn gas stream may be delivered to a critical process application. By "relatively stable" in this aspect what is meant is that the deviation from the mean does not vary by more than 5%. In some embodiments, the deviation is less than 3%.

In yet a further aspect of the invention, a method of delivering a process gas to a critical process application is provided comprising: (a) providing a gas phase of an multi-component liquid source comprising a first component and a second component which is less volatile than the first component, wherein the less volatile component is present at an initial concentration; (b) contacting the gas phase of the multicomponent liquid source with a carrier gas, whereby the concentration of the less volatile component in the multicomponent liquid source increases to a second concentration that is higher than the initial concentration; (c) adding to the multicomponent liquid source, while step (b) is occurring, a multicomponent liquid source comprising the first component and the second component which is less volatile than the first component, at a third concentration of the less volatile component that is lower than the second concentration; (d) withdrawing, after step (c) has begun, a gas stream comprising the resulting combined gas phase of the multicomponent liquid source and the carrier gas at a stable steady-state concentration of the less volatile component; and (e) delivering the gas stream to a critical process application.

In yet another aspect of the invention, a process gas delivery device for critical process applications is provided. Such a device comprises (a) an aqueous source comprising water and a component less volatile than water and a gas phase provided by the aqueous source, wherein the aqueous source comprises the component less volatile than water at an initial concentration, and wherein the gas phase comprises the component less volatile than water and water; (b) a carrier gas in fluid contact with the gas phase, whereby a gas stream comprising the component less volatile than water is formed, and whereby the formation of the gas stream, the concentration of component less volatile than water in the aqueous source increases to a second concentration that is higher than the initial concentration; (c) a fill tube that replenishes the aqueous source using an aqueous solution comprising the component less volatile than water at a third concentration that is lower than the second concentration; and (d) an apparatus that delivers the gas stream to the critical process application, wherein the delivered gas stream comprises the component less volatile than water at a stable steady-state concentration.

In other aspects of the invention, systems and devices for delivering a low volatility compound as a gas using the methods described herein are also provided. Generally, the systems and devices comprise (a) a multi-component liquid source having a gas phase optionally separated from the liquid source by a membrane wherein one component is water; (b) a carrier gas source that is in fluid contact with the gas phase, wherein the carrier gas comprises a carrier gas wherein the gas is undersaturated with respect to the moisture including where there is no or substantially no moisture; (c) a fill tube for replenishing the liquid source to maintain it at a relatively constant volume or is changed to a volume that is kept relatively constant; and (d) an apparatus for delivering a gas stream comprising at least one component of the liquid source.

In one other aspect of the invention, a method for reducing the concentration of hydrogen peroxide in an aqueous solution is provided comprising contacting the gas phase of the aqueous hydrogen peroxide solution with an oversaturated pre-loaded carrier gas comprising water to decrease the concentration of hydrogen peroxide to a relatively constant lower concentration wherein the amount of the water in the pre-loaded carrier gas is sufficient to keep the ratio of hydrogen peroxide and water in the reduced concentration solution relatively constant.

In yet another aspect of the invention, a method for reducing the concentration of hydrogen peroxide in an aqueous solution is provided comprising providing a gas phase of a multi-component liquid source having an initial concentration of a component less volatile than water and water; contacting an oversaturated pre-loaded carrier gas with the gas phase, wherein the pre-loaded carrier gas comprises a carrier gas and water such that the concentration of the component less volatile than water in the multi-component liquid source decreases to a relatively constant lower concentration; adjusting the water content in the pre-loaded carrier gas sufficient to keep the ratio of components in the multi-component liquid source at the lower concentration relatively constant; and delivering further amounts of a multi-component liquid to the multicomponent liquid source such that the volume of the multi-component liquid source remains relatively constant or is changed to a volume that is kept relatively constant.

It is to be understood that both the foregoing general description and the following detailed description are exemplary and explanatory only and are not restrictive of the invention.

The accompanying drawings, which are incorporated in and constitute a part of this specification, illustrate several embodiments of the invention.

DETAILED DESCRIPTION

Figure 1:
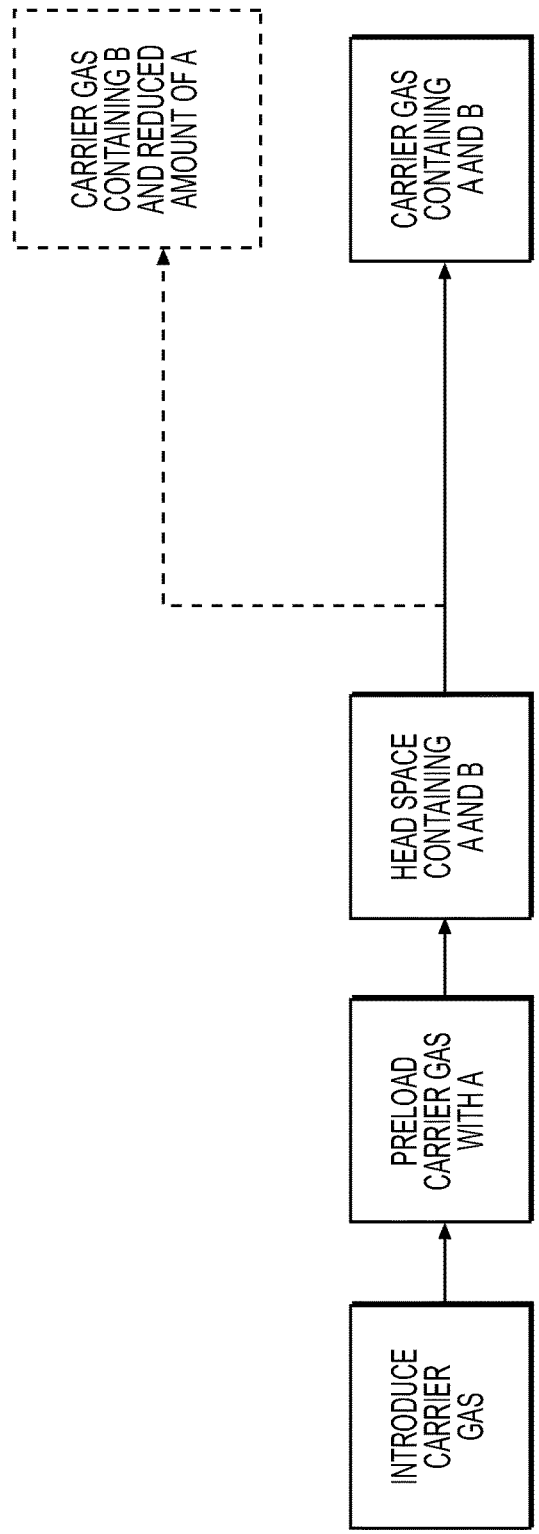
FIG. 1 is a process flow diagram illustrating certain embodiments of the present invention.

In embodiments wherein the amount of the high volatility component, such as, for example, water, in the carrier gas is keeping the ratio of the higher volatile component and the lower volatile component, such as, for example, hydrogen peroxide, relatively constant in the liquid source or gas phase or both, it may be helpful to consider Raoult's law. As an approximation, the following equation shows the partial pressure of the preloaded component for ideal solutions that follow Raoult's Law:

$$P(preload_a) = P'_a - (x_a/x_b)P'_b$$

$$P(preload_a) = P_a x_a - x_a P_b$$

$$P(preload_a) = x_a(P_a - P_b)$$

Wherein, $P(preload_a)$ is the partial pressure of component (A) in the carrier, $P'_a$ is the partial pressure of high volatility component A in the gas phase, $P'_b$ is the partial pressure of less volatile component B in the gas phase, $P_a$ is the vapor pressure of a pure solution of component A, $P_b$ is the gas pressure of a pure solution of component B, and $x_a$ and $x_b$ are the relative mole fractions of components A and B in the liquid source. Typically, the amount of the higher volatility component would need to be determined experimentally, because Raoult's Law is an idealized approximation and most solutions are non-ideal. But the approximation provided in these equations typically provides a useful starting point.

In many embodiments of the invention, the multi-component liquid source used is an aqueous hydrogen peroxide liquid source which is provided at an initial concentration. The gas phase over the liquid source may be located in a head space in fluid contact with the aqueous hydrogen peroxide source. When contacting the gas phase of the aqueous hydrogen peroxide source with an undersaturated carrier gas, such as a substantially dry carrier gas, the concentration of hydrogen peroxide in the aqueous hydrogen peroxide source increases to a second concentration, which may or may not be measured, that is higher than the initial concentration. The carrier gas typically contacts the gas phase of the aqueous hydrogen peroxide source in a continuous flow arrangement, so that the gas phase of the aqueous hydrogen peroxide source is continuously swept away from (i.e., removed from) the aqueous hydrogen peroxide source. In some embodiments, a separate measurement or calibration procedure is conducted so that the second concentration of hydrogen peroxide is established, at least approximately. This measurement or calibration procedure may involve carrying out the contacting step for a predetermined period of time, for example under controlled conditions of factors including, but not limited to, carrier gas flow rate and temperature. In fact, it naturally follows from preferential removal of water from the aqueous hydrogen peroxide source that the indicated second concentration of hydrogen peroxide will be higher than the initial concentration of hydrogen peroxide in the aqueous hydrogen peroxide source at a time after the gas phase of the aqueous hydrogen peroxide source was contacted with the carrier gas.

In these and other embodiments, while the contacting step is occurring, an aqueous hydrogen peroxide solution that includes hydrogen peroxide at a third concentration, where the third concentration is lower than the second concentration may be added. In many embodiments, the third concentration is the same as the initial concentration. The third concentration may be at a higher or lower concentration than the initial concentration provided that it is lower than the second concentration. Simply put, at the equilibrium concentration, the molar ratio of peroxide to water in the solution phase will equal the gas phase. The adding step can involve periodic or continuous addition, but generally takes place while the carrier gas is contacting the gas phase of the aqueous hydrogen peroxide source. For example, the carrier gas can contact the gas phase of the aqueous hydrogen peroxide source, sweep away the gas phase of the aqueous hydrogen peroxide source, and so remove mass or volume from the aqueous hydrogen peroxide source. In some embodiments, the step of adding the aqueous hydrogen peroxide solution that includes hydrogen peroxide at the third concentration can be carried out to maintain an essentially constant mass, or an essentially constant volume. The maintained constant mass or volume can be the same or different from the starting mass or volume of the aqueous hydrogen peroxide source at the time the method was initiated. For example, the maintained constant mass or volume can be the mass or volume resulting after the carrier gas has swept away a sufficient amount of the gas phase of the aqueous hydrogen peroxide source to reduce the mass or volume below the level at the start of the method. Further, such methods include the step of withdrawing, typically after the adding step has begun, a gas stream that includes the resulting combined gas phase of the aqueous hydrogen peroxide source and the carrier gas at a stable steady-state concentration of hydrogen peroxide. While the gas stream can be withdrawn and used prior to any addition of the aqueous hydrogen peroxide solution to the aqueous hydrogen peroxide source, such a gas stream may undesirably vary in its concentration of hydrogen peroxide. Conversely, withdrawing the gas stream after at least the initial addition (i.e., after the adding step has begun) of the aqueous hydrogen peroxide solution to the aqueous hydrogen peroxide source advantageously facilitates the stable steady-state concentration of hydrogen peroxide. In these and other embodiments, the gas stream may be delivered to a critical process application. For example, the critical process application may be directed to a material that is to be decontaminated and thereby becomes decontaminated. The embodiments described herein may be performed as a continuous process.

In many embodiments, the gas phase of the multi-component liquid source and the liquid phase are separated by a substantially gas-impermeable membrane. In many of these embodiments, the multicomponent liquid source is an aqueous hydrogen peroxide source and gas phase comprises hydrogen peroxide in the gas phase. The substantially gas-impermeable membrane may be a fluorinated ion-exchange membrane. In these and other embodiments, the carrier gas used to contact the gas phase can be a substantially dry carrier gas. Such embodiments further provide that the third concentration of the less volatile component of the multicomponent liquid source, such as for example, hydrogen peroxide in an aqueous hydrogen peroxide solution, can be the same as the initial concentration of the lower volatile component in the multicomponent liquid source, such as with aqueous hydrogen peroxide. With respect to hydrogen peroxide, exemplary embodiments include initial concentrations of hydrogen peroxide include between about 5% and about 50%.

In decontamination embodiments, the material to be decontaminated may be one of a number of different kinds of materials. For example, the material may be a device that amplifies nucleic acid or it may be a component removed from such a device that amplifies nucleic acid. When the material to be decontaminated contains DNA, the amount of amplifiable DNA may be reduced by at least 4 logs. When the material is a kind of material containing microorganisms, the number of viable microorganisms may be reduced by at least 6 logs. During the decontamination process, the gas stream may, for example, delivered to the material to be decontaminated for up to 60 minutes. When the material is the kind of material containing bacteria, the number of viable bacteria may be reduced by between about 6 logs and about 7 logs. Other materials which may be decontaminated according to the methods herein include those materials containing DNA products of an in vitro nucleic acid amplification reaction. The temperature may further be controlled during the decontamination process. For example, the decontamination can be done where the temperature of the material does not exceed about 40° C. In other examples, the temperature does not exceed about 30° C. In embodiments where the multicomponent liquid source is aqueous hydrogen peroxide, a gas-impermeable membrane separating the aqueous hydrogen peroxide source from the gas phase may be used in such embodiments with one such membrane being a fluorinated ion-exchange membrane. Additionally, in such embodiments, the materials to be decontaminated may be positioned in a vented chamber configured to permit continuous flow of the delivered gas stream either in cases where a membrane is present or not.

Other embodiments of the invention are directed to devices for decontaminating materials. Such devices may be used, for example, to deliver process gasses such as hydrogen peroxide gas to the material to be decontaminated. In the devices of the invention, the gas phase comprising a process gas such as hydrogen peroxide may be separated from the liquid source, such as aqueous hydrogen peroxide source by a substantially gas-impermeable membrane, such as with a fluorinated ion-exchange membrane. In these and other embodiments, the device may comprise an assembly whereby a carrier gas is delivered to the gas phase that comprises, for example, hydrogen peroxide and water so that the gas phase is continuously removed to form the hydrogen peroxide gas stream. This removal raises the initial concentration of the aqueous hydrogen peroxide to a second concentration. When the process gas is hydrogen peroxide, the aqueous hydrogen peroxide source is replenished with hydrogen peroxide at a concentration that is lower than the second concentration. For example, that replenished hydrogen peroxide concentration may be at the same concentration as the initial hydrogen peroxide concentration. The hydrogen peroxide gas is delivered via an apparatus to the material to be decontaminated wherein the apparatus comprises an outlet of a head space containing the gas phase, and wherein the outlet leads to the material to be decontaminated so that the hydrogen peroxide gas stream flows from the head space to the material to be decontaminated. Other process gasses may be utilized in connection with multicomponent liquid sources comprising a first component and a second component which is less volatile than the first component, wherein the less volatile component, when in the gas phase, may be a process gas.

By adjusting the operating conditions of the methods, systems, and devices provided herein, such as the temperature, saturation conditions, flow rate and pressure of the carrier gas, and/or the concentration of the multicomponent liquid source, the concentration of the replenishment source of the multicomponent liquid source, and the temperature and pressure of the multicomponent liquid source, the less volatile component in the multicomponent liquid source can be effectively and safely delivered as a process gas at various concentrations.

When aqueous hydrogen peroxide is the multicomponent liquid source, then by adjusting the operating conditions of the methods, systems, and devices provided herein, such as the temperature, saturation conditions, flow rate and pressure of the carrier gas, and/or the concentration of the liquid source hydrogen peroxide, the concentration of the replenishment source of hydrogen peroxide, and the temperature and pressure of the aqueous hydrogen peroxide source, hydrogen peroxide can be effectively and safely delivered as a process gas at various concentrations, such as for decontamination applications.

In certain embodiments, the carrier gas may be obtained, stored, and used directly in methods, system, and devices provided herein. In certain other embodiments, the carrier gas may be generated at the point of use from a carrier gas and at least one component of the liquid source, e.g., by a device for adding such component(s) to a carrier gas. Exemplary carrier gases comprise a carrier gas and water, alcohols, ketones, ethers, organic acids, inorganic acids, organic solvents, or inorganic solvents. One preferred carrier gas comprising, such as, for example, humidified nitrogen, which may be generated by contacting a nitrogen carrier gas with a humidifier device, e.g., a membrane contactor or a RainMaker™ humidification device available from RASIRC, Inc. of San Diego, Calif. Other exemplary carrier gases, may include other carrier gases as set forth herein including one or more of nitrogen, argon, hydrogen, oxygen, CO2, clean dry air, helium, or other gases that are stable at room temperature and atmospheric pressure. In other embodiments, a preferred carrier gas is a nitrogen carrier gas that has not been humidified. Clean dry air is another carrier gas. Clean room air is yet another carrier gas.

In some embodiments, an apparatus for delivering a process gas containing gas stream is an outlet of a head space, which contains the gas phase, connected directly or indirectly to a material to be decontaminated, allowing the process gas containing gas stream to flow from the head space to the material in which it will be used. For example, when hydrogen peroxide is a liquid source, such as an aqueous hydrogen peroxide liquid source, is enclosed in a compartment, a gas phase of the liquid source may be described as head space. In certain embodiments, the head space may be a space located adjacent to the liquid source and may be separated from the liquid source by a substantially gas-impermeable membrane. In those embodiments with a liquid source and a head space separated by a substantially gas-impermeable membrane, the head space may be located above, below, or on any side of the liquid source, or the head space may surround or be surrounded by the liquid source. For example, the head space may be the space inside a substantially gas-impermeable tube (e.g., a membrane lumen) running through the liquid source or the liquid source may be located inside a substantially gas-impermeable tube (e.g., a membrane lumen) with the head space surrounding the outside of the tube.

In certain embodiments the carrier gas is not humidified and contains no or substantially no water. In such embodiments, the maximum gas-phase output of the component that is less volatile, under stable steady-state conditions, will have a molar ratio of the less volatile component to the higher volatile component in the gas phase which will be equivalent to the molar ratio of the less volatile component to the higher volatile component in the solution phase of the liquid used to replenish the multi-component liquid source which may be, for example, aqueous hydrogen peroxide.

In many of these embodiments, the solution-phase concentration of the less volatile component, such as hydrogen peroxide, is concentrated with a dry or substantially dry carrier gas such as nitrogen, room air, or clean dry air or a combination thereof. In some embodiments the dew point of the solution is less than about 0° C. The liquid may be replenished so that as between the replenishment and the carrier gas flow rate, the desired concentration is maintained. Under these conditions, one can reach molar balance between the initial concentration of the less volatile component in the replenishment solution and the less volatile component in the gas phase for delivery for example, a material to be decontaminated. The replenishment solution concentration of the less volatile component to the more volatile component is typically of substantially the same concentration as that found in the initial concentration.

In some embodiments of the invention, the less volatile component from the multi-liquid source, which may be an aqueous hydrogen peroxide liquid source, is delivered in the gas phase. In other embodiments, the less volatile component may be delivered from bubbling through a solution.

Exemplary multi-component solutions are solutions containing organic or inorganic solvents; water- or alcohol-containing solutions of inorganic acids, inorganic bases, or oxidizing or reducing agents; aqueous $H_2O_2$ solutions; water-alcohol solutions, such as water-isopropanol solutions; $H_2O_2/H_2O$/isopropanol solutions; and aqueous hydrazine solutions. Such components may be selected such that they are less volatile than water. As discussed above, the composition of this solution may be dynamic and, according to Raoult's Law, the concentration of the low volatility compound may increase over time if the more volatile component is not replenished. In many embodiments, the liquid source comprises an aqueous $H_2O_2$ solution. In one embodiment, the initial concentration of the $H_2O_2$ solution prior to concentrating according to the invention is about 5% by weight. Unless otherwise specified, all percentages of concentrations set forth herein are weight percent. In other embodiments, the $H_2O_2$ solution prior to concentrating are about 25%, about 30%, about 35%, about 40%, about 45%, about 50%, about 55%, about 60%, about 65%, about 70%, about 75%, about 80%, about 85%, about 90%, as well as concentrations in between including about 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, or even 85-90%, by weight. For example, the initial hydrogen peroxide concentration can be between 5-90%, 25-75%, 30-50% or about 31.3%. At 31.3%, for example, this corresponds to a molar ratio of water to hydrogen peroxide of about 4:1. When such hydrogen peroxide concentrations are concentrated according to the invention, the resulting concentrations may be between about 50% and 90%, 60% and 90%, 60% and 80%, or about 70% and about 78%, for example. In these and other embodiments of the invention, the stable steady-state concentration of hydrogen peroxide can be between about 500 ppm and about 300,000 ppm including about 500 ppm to about 800 ppm. Other ranges include about 1 ppb to 1000 ppm, about 1000 ppm to about 5,000 ppm, about 5,000 ppm to about 15,000 ppm and about 15,000 ppm to about 60,000 ppm.

Although aqueous solutions are commonly used liquid sources in the methods, systems, and devices disclosed herein, the selection of applicable multi-component liquid solutions is not so limited. Selection of an appropriate multi-component liquid solution will be determined by the requirements of a particular application or process.

In some embodiments, the multi-component liquid source, such as an aqueous $H_2O_2$ solution, is provided at an initial concentration of the lower-volatile component which is then raised until it achieves a stable increased concentration. The initial concentration may be raised by providing a carrier gas which is undersaturated in the higher volatile component. In some embodiments, such undersaturation is achieved by having no or substantially no water content. In the case of an aqueous $H_2O_2$ solution, the water content is the higher volatile component. Following Raoult's law, the concentration of the lower-volatile multi-component liquid source, such as $H_2O_2$ will increase. In order to prevent the creation of such high concentrations so as to be hazardous, in some embodiments, the $H_2O_2$ liquid source can be replenished with a liquid having the initial concentration of the lower volatile component, or at a concentration lower than the initial concentration or lower than the concentration to which the initial concentration has increased due to the contact with the carrier gas. The amount added may be delivered so as to keep the overall volume of the $H_2O_2$ liquid source relatively constant. When a carrier gas contains water, the level of saturation of the carrier gas may be adjusted, depending on the amount of liquid replenished and its concentration so as to provide a stable increased concentration. The rate of the carrier flow gas may also be adjusted so as to provide a stable increased concentration. In some embodiments, the carrier gas together with the gas from the multi-component liquid source are delivered to a material to be decontaminated.

In certain embodiments, the methods, systems, and devices provided herein may employ a variety of membranes. The membrane is preferably permeable to a low volatility compound (e.g., hydrogen peroxide), particularly a substantially gas-impermeable membrane, e.g., a fluorinated ion-exchange membrane, such as a NAFION® membrane or other fluorinated ion-exchange membrane or derivatives or salts thereof. Aquivon® or Aquivon® P985 by Solvay, which is a proprietary short side chain copolymer of tetrafluorethylene and a sulfonyl fluoride vinyl ether may be used. In this manner, the low volatility compound passes through the membrane and is introduced into the gas stream on the other side of the membrane, thus providing a gas stream comprising the low volatility compound that can be used in various decontamination applications. In one embodiment, the membrane is a substantially gas-impermeable membrane with a high permeability for a low volatility compound (e.g., hydrogen peroxide). Permeability features of the membrane can be changed by varying the area, thickness, and type of membrane.

The devices provided herein may further comprise various components for containing and controlling the flow of the gases and liquids used therein. For example, the devices may further comprise mass flow controllers, valves, check valves, pressure gauges, regulators, rotameters, gravity feeds, pressurized refill containers, and pumps. The devices provided herein may further comprise various heaters, thermocouples, and temperature controllers to control the temperature of various components of the devices and steps of the methods. In certain embodiments, where an undersaturated carrier gas is employed, such devices are sometimes referred to herein as "Concentrators."

In many embodiments where the multicomponent liquid source is aqueous hydrogen peroxide, the source of aqueous hydrogen peroxide has a starting volume in equilibrium with a gas phase that includes water and hydrogen peroxide. Starting concentrations of hydrogen peroxide for the source of aqueous hydrogen peroxide solution may be about 30% by weight. In other embodiments, the $H_2O_2$ solution prior to concentrating are about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, as well as concentrations in between including about 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, or even 85-90%, by weight. A substantially dry carrier gas, in fluid contact with the gas phase, is also provided to form a gas that contains hydrogen peroxide. Examples of gasses that may be used include one or more of nitrogen, argon, hydrogen, oxygen, $CO_2$, clean dry air, helium, combinations thereof or other gases that are stable at room temperature and atmospheric pressure. Further, the device may include a fill tube that delivers aqueous hydrogen peroxide to the aqueous hydrogen peroxide source. This tube may be used to replenish aqueous hydrogen peroxide solution due to losses to the gas phase. In some embodiments, the amount of replacement volume is based on a weight determination. In some embodiments, this may be based on liquid level sensors. In some embodiments, the aqueous hydrogen peroxide solution that is used for the replenishing is the same as the starting concentration of hydrogen peroxide used for the original source of aqueous hydrogen peroxide solution. A pump connected to the fill tube can be used to replenish the liquid volume of hydrogen peroxide through the fill tube. The fill tube may be used to replenish the aqueous hydrogen peroxide source so that the aqueous hydrogen peroxide source maintains a substantially constant volume.

In some embodiments, the replenishment solution may be gravity fed from a container or from a pressurized vessel or circulation loop. In certain preferred embodiments, a pathway by which the substantially dry carrier gas is delivered to the gas phase of the aqueous hydrogen peroxide solution is provided. In these and other embodiments, the gas phase may be removed to provide a hydrogen peroxide gas stream. Such removal may be continuous. In some embodiments the assembly includes pipes or conduits, as may be temperature-controlled by the use of heat tracing, serve to guide the substantially dry carrier gas to the gas phase, and further to sweep away the gas phase, thereby providing the hydrogen peroxide gas stream and prevent condensation of the less volatile component of the gas stream.

The gas phase may be located adjacent to the liquid source, such as, for example, aqueous hydrogen peroxide, and may be separated from the liquid source by a substantially gas-impermeable membrane. In such instances the head space may be located above, below, or on any side of the liquid source, or the head space may surround or be surrounded by the liquid source. In certain embodiments, the head space may be the space inside a substantially gas-impermeable tube, such as a membrane lumen, running through the liquid source or the liquid source may be located inside a substantially gas-impermeable tube (e.g., a membrane lumen) with the head space surrounding the outside of the tube. Accordingly, the assembly component of such devices can include a substantially gas-impermeable membrane separating the gas phase from the liquid volume of the multicomponent liquid source such as, for example, aqueous hydrogen peroxides.

Such devices may include an apparatus that delivers the process gas to the critical process application. The apparatus may include some kind of tubing or conduit for guiding delivery of the process gas. There also can be a nozzle and/or a valve for directing and controlling flow of the process gas. For decontamination applications, for example, the process gas stream may be directed into an enclosed or vented chamber into which components to be decontaminated may be placed at the start of the decontamination procedure. The process gas stream so delivered includes the process gas at a stable steady-state concentration. In many such embodiments, the process gas is hydrogen peroxide and the multi-component liquid source is aqueous hydrogen peroxide.

In decontamination applications, the devices and methods herein may be used for reducing the number of viable microorganisms and/or rendering DNA non-amplifiable on various materials including, but not limited to, environmental surfaces, medical devices, medical diagnostic instruments, medical waste products, food products and containers, and fresh produce Enclosed spaces and surfaces within such enclosed spaces may also be decontaminated. For example, the devices of the invention may be placed in rooms in hospitals or other healthcare venues for a period of time sufficient to reduce or eliminate pathogens, such as bacterial pathogens. Other materials may be surfaces including internal or external parts of instruments used for performing in vitro nucleic acid amplification reactions. For example, gas phase hydrogen peroxide employed for decontaminating such instruments would be able to access internal spaces that could not practically be decontaminated by other approaches such as irradiation with ultraviolet light.

In some embodiments, the disclosed hydrogen peroxide delivery devices deliver hydrogen peroxide gas streams at temperatures well above room temperatures such as about 100° C. This allows for substantially higher concentrations of hydrogen peroxide in the gas phase without condensation occurring. This has particular application for decontaminating or sterilizing medical instruments at high temperatures. In other embodiments, lower temperatures can be used. Lower temperature operation, such as at room temperature, 30° C., 40° C., or temperatures in between is generally associated with lower amounts of hydrogen peroxide due to saturation pressure limits at those temperatures. However, when decontaminating a room or other large area, it is possible to generate the hydrogen peroxide gas at high temperature, and then dilute at high flow rate. This would allow for rapid filling of a room with hydrogen peroxide gas. For example, an average concentration of about 50,000 ppm hydrogen peroxide gas can be achieved from the devices of the invention. When expanded into a typical room to be decontaminated, it is expected that the concentration of hydrogen peroxide would be on the order of 1000 ppm.

The term "critical process application" as used herein includes decontamination applications or applications directed to microelectronics and semiconductors. Such applications include those which could benefit from techniques which allowed for the use of gaseous process chemicals obtained from a multi-component liquid source. Critical process applications further include, but are not limited to atomic layer deposition, atomic layer etch, wafer: bonding, cleaning, annealing, stripping, thermal oxidation, chemical oxidation, chemical vapor deposition, sputtering, MBE, and surface passivation; decontamination: of materials such as medical instruments, genetic sequencing equipment, food preparation surfaces, food surfaces, and surfaces in hospital rooms, public spaces and transportation vehicles by killing or reducing the number of DNA, bacteria, viruses, spores, mold, and/or pyrogens from materials; annealing of amorphous oxides for displays and TFTs, industrial application such as plasma oxidation of surfaces for painting and hydrophobic conversion, CVD, sputtering, oxidation, and passivation.

The term "process gas" as used herein is a broad term, and is to be given its ordinary and customary meaning to a person of ordinary skill in the art (and is not to be limited to a special or customized meaning), and refers without limitation to a gas that is used in a critical application process, such as the decontamination of a material or cleaning the surfaces of semiconductors or the chemical modification of semiconductor surfaces to form an oxide, hydroxyl ligand. Similarly, such surfaces may be passivated by the removal of carbon atoms, or reacted with photoresist or photoresist byproducts, or annealing spin-on dielectrics or spin-on silicon based precursors. Exemplary process gases are water, inorganic acids, organic acids, inorganic bases, organic bases, and inorganic and organic solvents. A particular process gas is hydrogen peroxide gas.

The term "carrier gas" as used herein is a broad term, and is to be given its ordinary and customary meaning to a person of ordinary skill in the art (and is not to be limited to a special or customized meaning), and refers without limitation to a gas that is used to carry another gas through a process train, which is typically a train of piping. Exemplary carrier gases are nitrogen, argon, hydrogen, oxygen, $CO_2$, clean dry air, room air, helium, or other gases or combinations thereof that are stable at room temperature and atmospheric pressure. A carrier gas may be an inert gas. In one embodiment, the carrier gas is nitrogen. The carrier gas may be solely an inert gas or it may have one or more additional components. A carrier gas may further comprise water, for example. By "dry nitrogen" what is meant is a nitrogen gas substantially free of water. In other embodiments, the carrier gas may be hydrogen, clean dry air, oxygen, ozone, or combinations thereof. In some embodiments, the carrier gas may be substantially free of water. In certain embodiments, the carrier gas is not passed through a humidifier. In one embodiment, the carrier gas contains an inert gas and water. As used herein in the invention, when water is identified as a component of the gas, unless otherwise provided, it is understood to be water in the gas phase.

The term "inert gas" as used herein is a broad term, and is to be given its ordinary and customary meaning to a person of ordinary skill in the art (and is not to be limited to a special or customized meaning), and includes without limitation a gas that is not permeable to the membrane as described herein. In one embodiment, the inert gas is nitrogen. In another embodiment, the inert gas is dry nitrogen.

The term "liquid source" as used herein is a broad term, and is to be given its ordinary and customary meaning to a person of ordinary skill in the art (and is not to be limited to a special or customized meaning), and refers without limitation to a liquid solution that provides the source of a gas used in an application or process, specifically a process gas.

The term "head space" as used herein is a broad term, and is to be given its ordinary and customary meaning to a person of ordinary skill in the art (and is not to be limited to a special or customized meaning), and refers without limitation to a volume of gas in fluid contact with a liquid source that provides at least a portion of the gas contained in the head space. There may be a permeable or selectively permeable barrier separating the head space from the liquid source.

The term "pre-loaded carrier gas" means a carrier gas containing an amount of one or more component(s) of a liquid source. In one embodiment, the pre-loaded carrier gas contains an inert gas and water. In another embodiment, the pre-loaded carrier gas comprises one or more of nitrogen, argon, hydrogen, oxygen, $CO_2$, clean dry air, helium, or other gases that are stable at room temperature and atmospheric pressure and water. A pre-loaded carrier gas is also considered a carrier gas.

The term "substantially gas-impermeable membrane" as used herein is a broad term, and is to be given its ordinary and customary meaning to a person of ordinary skill in the art (and is not to be limited to a special or customized meaning), and refers without limitation to a membrane that is relatively permeable to other components that may be present in a gaseous or liquid phase, e.g., water or hydrogen peroxide, but relatively impermeable to other gases such as, but not limited to, hydrogen, nitrogen, oxygen, carbon monoxide, carbon dioxide, clean dry air, room air, hydrogen sulfide, hydrocarbons (e.g., ethylene), volatile acids and bases, refractory compounds, and volatile organic compounds. Examples of substantially gas-impermeable membranes include NAFION®, AQUIVON® or 3M IONOMER® and others known in the art.

The term "substantially dry carrier gas" means gas, or a particularly kind of gas if in relation to clean dry air or nitrogen for example, that is dehumidified by methods known in the art reduce moisture in a gas so as to deliver a gas that is as dry as practicable. Such methods include, but are not limited to using gas purifiers such as those available from commercial manufacturers.

The term "ion-exchange membrane" as used herein is a broad term, and is to be given its ordinary and customary meaning to a person of ordinary skill in the art (and is not to be limited to a special or customized meaning), and refers without limitation to a membrane comprising chemical groups capable of combining with ions or exchanging with ions between the membrane and an external substance. Such chemical groups include, but are not limited to, sulfonic acid, carboxylic acid, phosphoric acid, phosphinic acid, sulfamides, sulfonyl imides, arsenic groups, selenic groups, and phenol groups. Such ion exchange membranes, including fluorinated ion-exchange membranes, often contain acid functionalities and, therefore, may be considered in an acid form. NAFION®, which is a fluorinated ion-exchange membrane, or other fluorinated-ion exchange membranes, may be chemically treated, for example, with an acid, base or salt, to modify reactivity. In certain embodiments, fluorinated ion-exchange membranes may be treated under suitable conditions to form various salt species. Examples of such salts include the sodium, pyridinium, ammonium, potassium, magnesium, iron, aluminum, and calcium salts.

The term "relatively constant" as used herein is a broad term, and is to be given its ordinary and customary meaning to a person of ordinary skill in the art (and is not to be limited to a special or customized meaning), and refers without limitation to a value that, although it may change with time, does not change so substantially so as to render the value inoperative or substantially less operative. In the context of increasing the concentration of a low volatile component, such as $H_2O_2$, it means maintaining a concentration at sufficiently high levels so as to provide a stable gas delivery of the low component gas for sufficient time to be applied to a critical process application. For example, maintaining a standard deviation of to within 3% or up to 5% of the mean for an hour would be considered relatively constant with respect to a concentration or a volume.

The term "undersaturated" means, in the context of a gas, such as a carrier gas or carrier gas, that the partial pressure of the gas is less than the maximum partial pressure for that gas in the head space or the carrier gas or carrier gas for the given temperature and pressure. The term undersaturated applies at a point specific point in time. The carrier gas may be saturated for a specific temperature and pressure and later be modified by reducing the pressure or increasing the temperature such that the head space or carrier gas is now undersaturated.

The term "oversaturated" means, in the context of a gas, such as a carrier gas or carrier gas, that the that the partial pressure of the gas is greater than the maximum partial pressure for that gas in the head space or the carrier gas or carrier gas for the given temperature and pressure. In some embodiments of the invention, the gas stream delivered to the critical process application is at a higher partial pressure of the component less volatile than water than the partial pressure of that component from the multi-component liquid source used to replenish prior to delivery of that liquid.

The term "equilibrium concentration" as used herein means the maximum amount of the less volatile component that may be delivered into the gas phase to be used, for example, to decontaminate a material and will be dependent upon temperature and head space pressure. Under such equilibrium conditions, the molar ratio of the less volatile component to the higher volatile component in the gas phase will be equivalent to the molar ratio of the less volatile component to the higher volatile component in the solution phase of the liquid used to replenish the multi-component liquid source. In solutions with multiple components, under such equilibrium conditions in accordance with the present invention, the molar ratio of the less volatile component to the higher volatile components in the gas phase will be equivalent to the molar ratio of the less volatile component to the higher volatile components in the solution phase of the liquid used to replenish the multi-component liquid source.

The term "stable" in the context of the output gas comprising the less volatile component from the multi-component liquid source, such as hydrogen peroxide in the gas-phase at a stable stead-state concentration means an output concentration that does not vary beyond certain parameters such as, for example, by more than 10% in some embodiments and not by more than 5%, 3% or 2% in other embodiments. The term applies once an equilibrium concentration of the less volatile component in the gas phase has been achieved and is being delivered to a critical process application. The percentages herein are the standard deviation from the mean with respect to the mean of measured gas output.

The term "stable steady-state concentration" in the context of the output gas comprising the less volatile component from the multi-component liquid source means an output that has increased to a concentration that is stable and in equilibrium as those terms are used herein.

The terms "decontaminate" and "decontamination" and "decontaminating" refer to killing or lysing any microorganism, or rendering a DNA molecule incapable of being amplified in an in vitro nucleic acid amplification reaction, such as in a PCR reaction. For example, in some embodiments, decontamination may reduce the number of viable microorganisms or the amount of DNA that can be amplified in an in vitro nucleic acid amplification reaction, such as in a PCR reaction, by at least 1 log compared to the material before processing for decontamination. A reduction of 1 log means that 10% of the original number of microorganisms or DNA material remains after a particular decontamination. Decontamination as used herein often results in a reduction of between about 1 log and 8 logs; including between about 3 logs and 7 logs. In some embodiments, decontamination can also succeed in sterilizing (i.e., 100% killing). In some embodiments, decontamination can completely inactivate DNA as a template in a PCR reaction. The invention may be used to kill or lyse any microorganism that is sensitive to hydrogen peroxide, as may be determined from the literature available to one of ordinary skill in the art. Examples include gram (−) bacteria including medically relevant gram (−) bacteria such as *E. coli, Acinetobacter baumanii, Pseudomonas aeruginosa, Klebsiella pneumonia*, and *Neisseria gonorrhoeae*. Examples further include gram (+) bacteria including medically relevant gram (+) bacteria such as *Corynebacterium, Mycobacterium, Listeria, Bacillus, Clostridium, Nocardia, Streptococcus, Staphylococcus*, and *Streptomyces*. Other microorganisms sensitive to hydrogen peroxide which may be killed or lysed by the methods and devices of the invention include viruses, yeasts, and fungi. Decontamination further includes disinfecting such as killing or lysing microbials or denaturing or destruction of DNA or RNA. Such disinfection may be applied to analytical instruments, such as polymerase chain reaction instruments, clinical instruments, hospitals, clinics, laboratories, dental offices, home care and chronic care facilities.

As used herein, the term "substantially reduce" with respect to decontamination denotes reduction of viable microorganisms in a sample by 1 log.

The term "gas" means gaseous species that is not a liquid or a solid as those terms are well understood in the art. Further, a gas is not a mist or a fog as would be generated, for example, by a nebulizer or atomizer. As used herein, the term gas further means that there are fewer than 100 particles of greater than 100 nm in size at standard temperature and pressure conditions in a volume of one liter as measured with a standard condensation nucleation counter. In a multicomponent liquid, such as water and hydrogen peroxide, when volatilized and delivered to a critical process application such as a material to be decontaminated, the hydrogen peroxide is in the gas phase. By comparison, it is possible that water, when volatilized and introduced into a carrier gas, may be either a gas or a vapor provided, however, that the output to the critical process application such as a material to be decontaminated is a gas.

In these and other embodiments of the invention, the further amounts of a multi-component liquid added to the multicomponent liquid source such that the volume of the multi-component liquid source is relatively constant or is changed to a volume that is kept relatively constant, may be of the same or of a different ratio of components as the original multi-component liquid. This process serves to replenish the multi-component liquid source In these and other embodiments of the invention, the concentration of the less volatile component in the gas phase may be changed by changing at least one of the following parameters: (a) the temperature of the liquid source, (b) the pressure of the liquid source, (c) the concentration of the liquid source, (d) the temperature of the carrier gas, (e) the pressure of the carrier gas, (f) replenishment liquid concentration of the components, and (g) the carrier gas flow rate. When a gas impermeable membrane is present, such as a fluorinated ion-exchange membrane, the surface area, thickness, and type of the membrane may also be changed.

In many embodiments of the invention, a gas phase of the less volatile component of the multi-component liquid source, such as hydrogen peroxide, is provided so that it may be delivered to a material to be decontaminated such that a steady-state concentration of the less volatile component in the gas phase is stable to within 10%, 5%, 3% or 2%.

The gas stream to be delivered to the material to be decontaminated may be heated in multiple embodiments of the invention. The temperature may be maintained at ambient temperature such as at about 20° C. or may be raised to about 120° C. Other temperatures include temperatures in between including about 70° C. In other embodiments, the pressure of the environment wherein the critical process application is maintained may be at atmospheric pressure or less. For example, that pressure may be at about 3.0 to about 1.0 atmospheres. In other examples, the atmospheric pressure may be less than 1.0 or 0.1 atmospheres.

By changing the temperature of the gas stream and pressure, the concentration of the component less volatile than water in the gas stream, such as hydrogen peroxide, may be changed. For example, with respect to hydrogen peroxide, the concentration may be as high as about 60,000 ppm such when the pressure of the environment of the critical process application is about atmospheric pressure. In other embodiments, the amounts may be about 20,000 to about 40,000 ppm including 20,000 ppm, 25,000 ppm 30,000 ppm 35,000 ppm, and 60,000 ppm and values in between under such atmospheric conditions. In embodiments where the pressure is reduced, such as to between about 1 mtorr and about 1 atmosphere, or 0.5 atmosphere to about 1 atmosphere, or about 1 mtorr to about 0.1 atmosphere, the concentration of the component less volatile than water in the gas stream, such as hydrogen peroxide, may be as high as about 330,000 ppm.

Methods for killing microbes or disinfecting methods typically provide for hydrogen peroxide gas streams wherein the mean concentration of hydrogen peroxide in the gas stream is at least 100 ppm. In some embodiments, the mean concentration is greater than 500 ppm. In other embodiments, the mean concentration is between about 500 ppm and 15,000 ppm. In many embodiments, the hydrogen peroxide gas concentration in the gas stream to be delivered to a decontamination application is stable to within 10% or better of the mean concentration such as 9%, 8%, 7%, 6%, or 5% of the mean concentration. In some embodiments the stability is to within 4% of the mean of the concentration, such as 3%, 2% 1% or less. Such percentages represent a standard deviation during the course of experimentation. Further, the peroxide delivery system of the invention can provide such hydrogen peroxide gas streams. Solutions containing hydrogen peroxide and water may have a concentration of peroxide ranging from about 5% to about 84% or even higher.

In many embodiments of the invention, the hydrogen peroxide concentrations produced are able to produce a rate of 6 log kill or greater in less than five hours and in many embodiments, less than thirty minutes.

FIG. 1 shows a process flow diagram illustrating certain embodiments of the methods, systems, and devices of the present invention. As shown in FIG. 1, a carrier gas pre-loaded with a component A can be introduced into a device or system. The carrier gas can be preloaded with a component A (e.g., water) utilizing a humidifier, chemical volatilizer or other like device. When used with a humidifier, the carrier gas is pre-loaded with water. One can adjust the saturation of the water in the carrier gas, by changing the temperature of the carrier gas for example. The carrier gas preloaded with A can then flow through a membrane contactor containing component A and a component B (e.g., $H_2O_2$). If the carrier gas pre-loaded with A is undersaturated with water (where A is water), then it will cause the concentration of component B to increase in the liquid phase. Optionally, the liquid source corresponding to the head space containing A and B, can be replenished with B in the liquid phase so as to maintain an approximately constant volume in the liquid phase. Carrier gas discharged from the membrane contactor can contain component A and component B, which can be provided as a process gas. Carrier gas containing component B and a reduced amount of A can then be provided as a process gas.

Figure 2A:
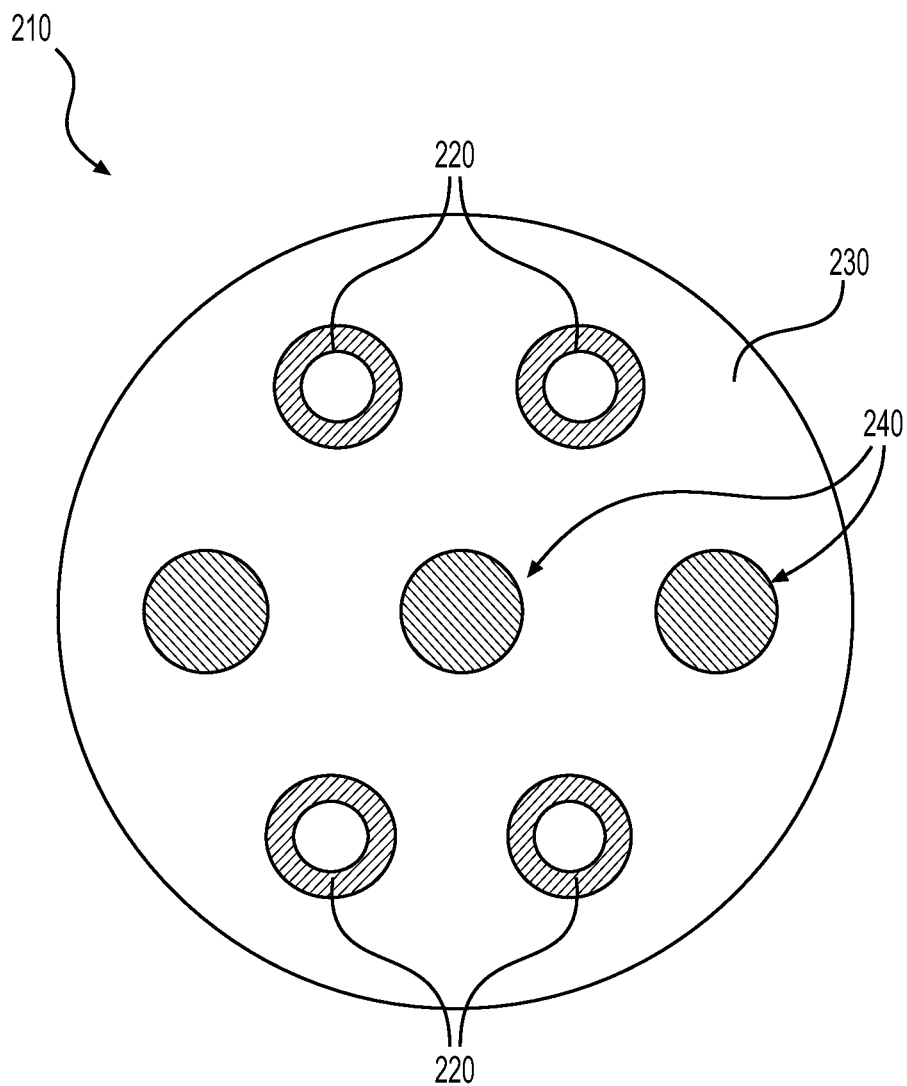
FIG. 2A is a diagram illustrating a part of a membrane assembly useful in certain embodiments of the present invention.
Figure 2B:
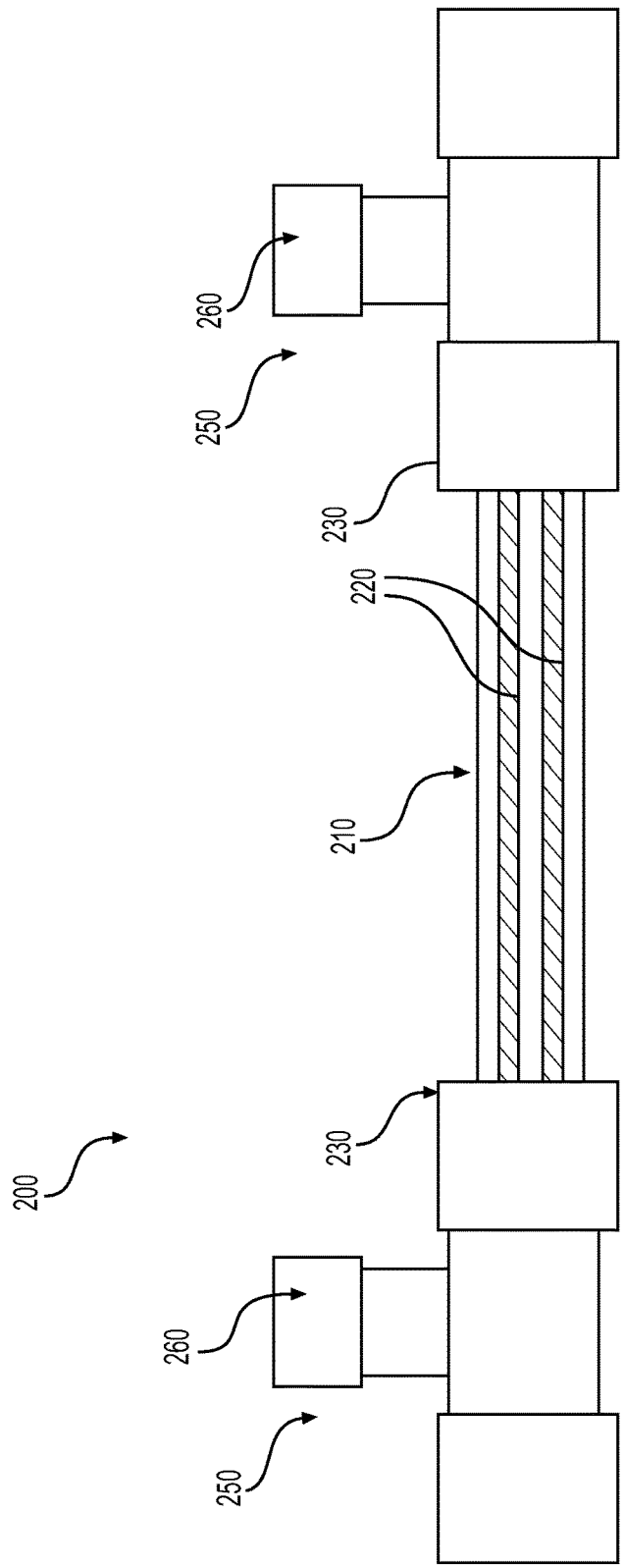
FIG. 2B is a diagram illustrating a membrane contactor assembly useful in certain embodiments of the present invention, such as a hydrogen peroxide delivery assembly (HPDA).

FIGS. 2A and 2B depict different views of one embodiment of a membrane contactor assembly 200 (e.g., a hydrogen peroxide delivery assembly) and a membrane assembly 210 that forms part of a membrane contactor assembly that can be used as provided herein. FIG. 2A shows membrane assembly 210 comprising a plurality membranes 220, for example, 5R NAFION® membrane, which can be configured as lumens. As depicted in FIG. 2A, membranes 220 configured into lumens are inserted into a collector plate 230 through a plurality of holes within collector plate 230. Membrane assembly 210 also comprises a plurality of polytetrafluoroethylenene (PTFE) rods 240 inserted into collector plate 230. As shown in FIG. 2B, as part of membrane contactor assembly 200, membrane assembly 210 comprises membrane lumens 220 spanning collector plates 230. Membrane contactor assembly 200 further comprises endcaps 250 at each end of membrane assembly 210. Endcaps 250 further include branches 260, which can be fitted with tubing to provide access to the interior of membrane contactor assembly 200, e.g., to fill, empty, clean, or refill the membrane contactor assembly.

Figure 3:
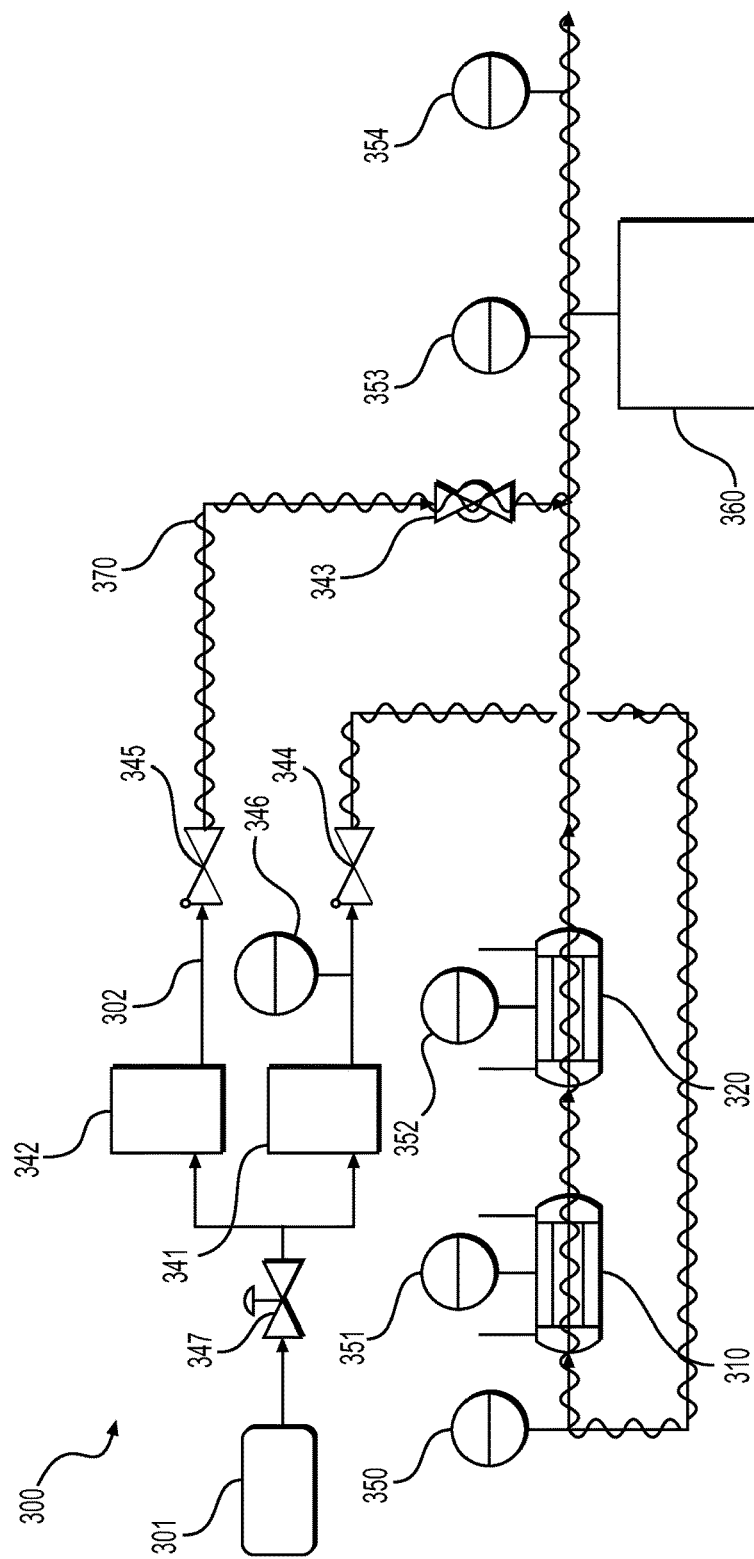
FIG. 3 is a P&ID of a delivery system according to certain embodiments of the present invention.

An embodiment according to an aspect of the methods, systems, and devices provided herein is described below by reference to FIG. 3. A delivery device 300 can comprise a humidifier 310, and a membrane contactor 320 as shown in FIG. 3. A carrier gas 301 (e.g., nitrogen) can flow through a head space in membrane contactor 320. A mass flow controller (MFC) 341 can be used to control the flow rate of nitrogen carrier gas 301. A mass flow controller (MFC) 342 can control a dilution gas 302 (e.g., nitrogen) flow rate. A valve 343 can isolate the dilution line when it is not desired. Check valves 344, 345 can be placed downstream of both MFC 341 and MFC 342 to protect them, e.g., from exposure to process gases (e.g., $H_2O$ and $H_2O_2$). A pressure gauge 346 can be placed between MFC 341 and check valve 344 to insure that the manifold's pressure does not exceed a maximum pressure, e.g., 5 psig for certain types of an analyzer 360.

The carrier gas pressure can be maintained with a forward pressure regulator 347, typically set to 15 psig. Carrier gas can flow through humidifier 310 and become pre-loaded with water, or other more volatile component of a multi-component solution (i.e., component A as described above by reference to FIG. 1). The humidifier can be configure so that the carrier gas leaving the humidifier is undersaturated, saturated, or oversaturated with moisture or other more volatile component of a multi-component solution. The degree of saturation can be controlled by controlling the temperature and flow rate. A thermocouple 350 can measure the temperature of carrier gas before it enters humidifier 310. A thermocouple 351 can measure the temperature of the liquid in humidifier 310. After exiting humidifier 310, the carrier gas can enter membrane contactor assembly 320 where a low volatility component can be added to the carrier gas from a multi-component solution (i.e., component B as described above by reference to FIG. 1), e.g, hydrogen peroxide. A thermocouple 352 can measure the temperature of the multi-component solution in membrane contactor assembly 320. A thermocouple 353 can measure the carrier gas temperature before optionally entering analyzer 360. After being analyzed, the remaining gas can be sent to a humidity transmitter 354 to measure the relative humidity (RH) and temperature before venting it.

Heater tape 370 can be placed on certain sections of delivery device 300 as shown in FIG. 3. Delivery device 300 can be controlled in two separate zones, the membrane assemblies and the remaining tubing using a Watlow controller. The entire device can be setup inside of a fume hood.

Figure 5:
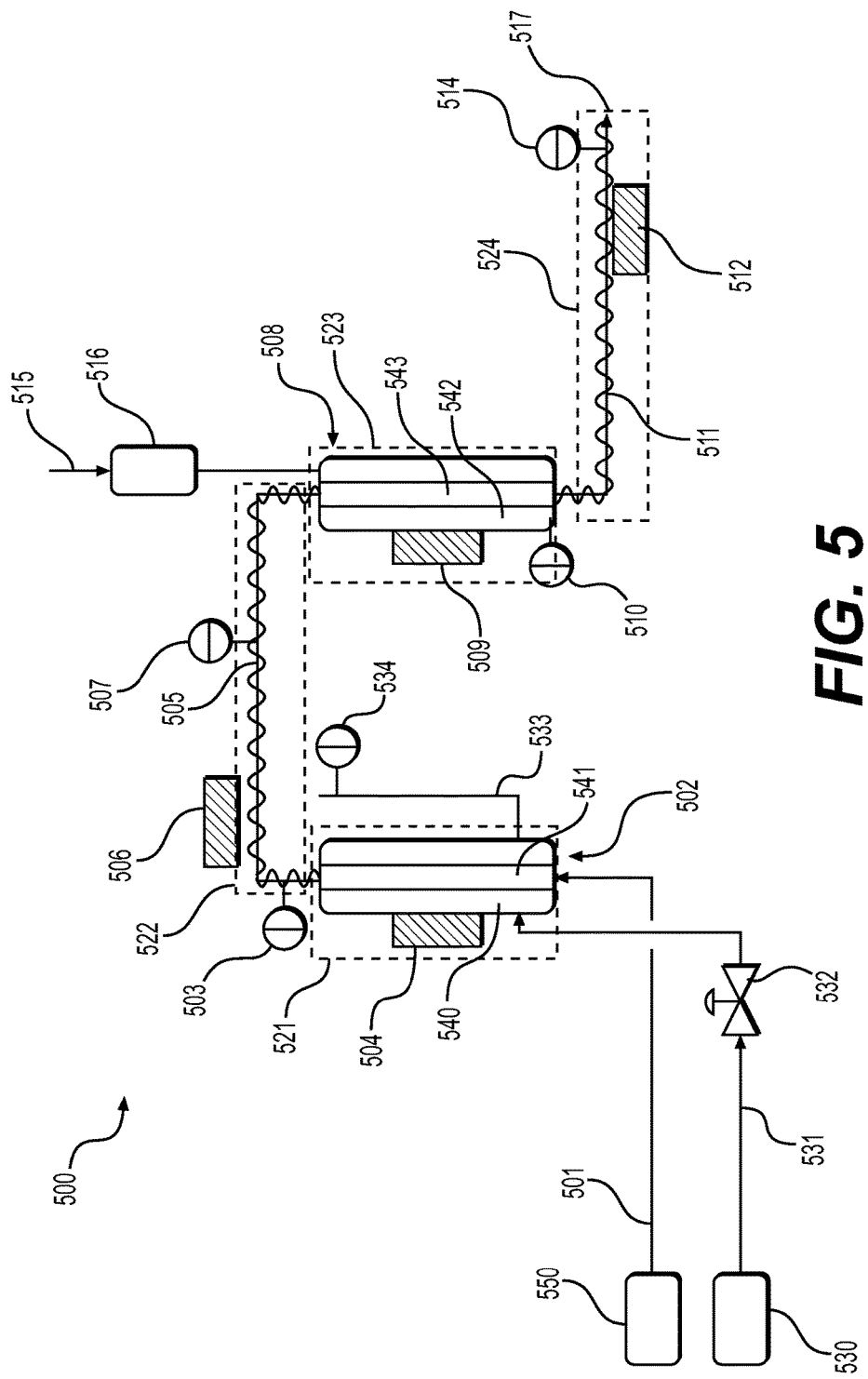
FIG. 5 is a P&ID of a delivery system according to certain embodiments of the present invention.

FIG. 5 shows a P&ID of certain embodiments of the invention for a delivery system 500 for delivering a low volatility component, e.g., hydrogen peroxide, of a multi-component liquid solution, e.g., an aqueous hydrogen peroxide solution. When configured as a hydrogen peroxide delivery system (HPDS), delivery system 500 can comprise a humidifier 502 in fluid communication with an HPDA 508, e.g., a membrane. In such configuration, delivery system 500 can be configured to receive a carrier gas 550 into humidifier 502 through a gas tubing 501. Carrier gas 550 can flow into a plurality of membranes 541 within humidifier 502.

In addition, humidifier 502 can be configured to receive a water source 530 (e.g., DI water) through a water tubing 531 into water/gas chamber 540 within humidifier 502. Humidifier 502 can be configured to increase the moisture content of carrier gas 550 flowing through membranes 541. The moisture concentration of the pre-loaded/humidified carrier gas exiting humidifier 502 can be controlled by a heater 504 and a dewpoint probe 503. The moisture concentration of the pre-loaded/humidified carrier gas can be increased or decreased to a setpoint by increasing or decreasing the temperature setpoint of heater 504. By changing the setpoint, one can provide a carrier gas that is undersaturated, saturated, or oversaturated with humidity. The flow rate of the carrier gas can also be changed to alter the saturation of the carrier gas.

Pre-loaded/humidified carrier gas can exit humidifier 502 into a gas tube 505. The temperature of the carrier gas can be maintained above the dew point by heating gas tube 505 with heater 506, and the temperature can be measured and controlled with thermocouple 507. Alternatively, the temperature of the carrier gas can be maintained below the dew point by selectively heating gas tube 505 with heater 506, and the temperature can be measured and controlled with thermocouple 507. The temperature setpoint of heater 506 can be greater than the temperature setpoint of heater 504 in order to limit condensation of water from the pre-loaded/ humidified carrier gas. Alternatively, by setting the temperature of heater 506 so that it is less that the temperature setpoint of heater 504, one can create an undersaturated pre-loaded/humidified carrier gas.

Pre-loaded/humidified carrier gas can then flow into membrane contactor assembly 508, which can be an HPDA. Membrane contactor assembly 508 can comprise a plurality of membrane lumens 543 and a multi-component solution 542 (e.g., aqueous hydrogen peroxide solution) contained within the shell of membrane contactor assembly 508. Pre-loaded/humidified carrier gas can flow into membrane lumens 543 where multi-component solution 542 is volatized through membrane lumens 543. The concentration of gas from the multi-component solution entering the pre-loaded/humidified carrier gas can be controlled through thermal regulation. The temperature of the multi-component solution can be controlled with a heater 509, and the temperature of the multi-component solution can be measured with thermocouple 510. The concentration of components of the multi-component solution in the gas phase can be increased or decreased to a setpoint by increasing or decreasing the setpoint of heater 509.

The carrier gas exiting membrane contactor assembly 508 through gas tube 511 contains both components of the multi-component solution in the gas phase. The temperature of that carrier gas can be controlled using a heater 512 and a thermocouple 514. Heater 512 can wrap around gas tube 511. That carrier gas, which contains the desired low volatility component can be delivered to a process throughout outlet 517.

The water level in humidifier 502 can be maintained through automatic filling. As the water in humidifier 502 is transferred to gas phase into carrier gas 550 the water level can drop. When the level drops below a set level sensed by fill sensor 534 located on a water level leg 533, a valve 532 can open to allow flow into humidifier 502. The water level can rise in the humidifier 502 up to a set level sensed by fill sensor 534. When the water level reaches the set level of fill sensor 534, valve 532 can close.

The multi-component solution 542 contained in membrane contactor assembly 508 can be filled and replenished through fill tube 515, which fills membrane contactor assembly 508 and then a reservoir 516. This can be accomplished automatically in a manner similar to humidifier 502. In one embodiment, this replenishment occurs so that the volume of multi-component solution 542 remains approximately constant. Reservoir 516 can serve the purpose of maintaining level of multi-component solution 542 in membrane contactor 508 for longer periods of time.

Delivery system 500 (e.g., an HPDS) can be separated into four temperature controlled zones, a first zone 521, a second zone 522, a third zone 523, and a fourth zone 524. Carrier gas can flow through delivery system 500 and the corresponding temperature zones starting in first zone 521 and then flowing into second zone 522, third zone 533, and ending in fourth zone 524 before being discharged. First zone 521 can have the lowest temperature, second zone 522 can have setpoint greater than first zone 521, third zone 523 can have a setpoint great than second zone 522, and fourth zone 524 can have the highest temperature setpoint in order to limit the possibility of condensation of water out of the carrier gas.

Figure 6:
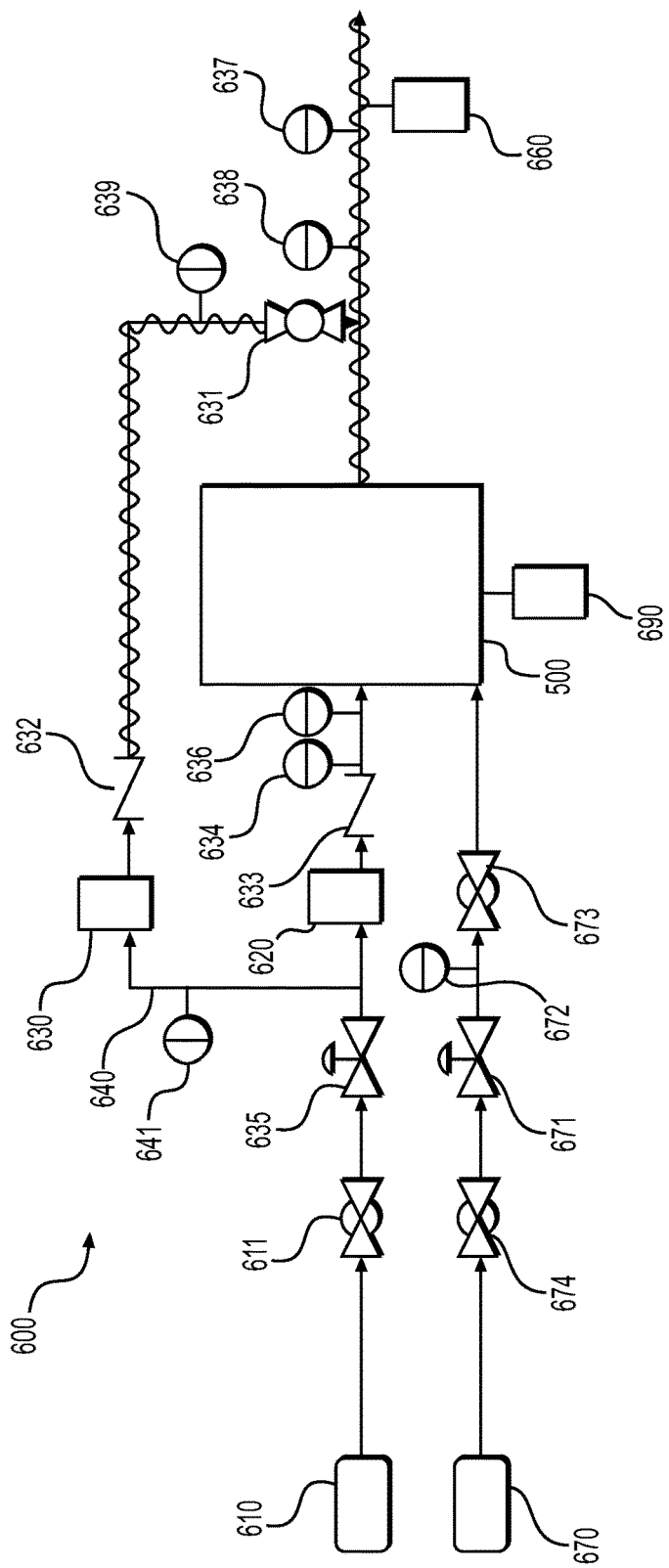
FIG. 6 is a P&ID of a delivery system according to certain embodiments of the present invention.

FIG. 6 shows a P&ID of delivery and monitoring system 600 that can be used to deliver gas from a low volatility component, e.g., hydrogen peroxide, of a multicomponent solution, according to certain embodiments of the methods, systems, and devices provided herein. Delivery and monitoring system 600 can be configured to connect a delivery system 500 (e.g., an HPDS) as described above.

Delivery system 600 can be configured to receive a carrier gas 610 (e.g., nitrogen gas) through a mass flow controller (MFC) 620. MFC 620 can be used to control the flow rate of carrier gas 610 into delivery system 500.

MFC 630 can be configured to control the flow rate of a carrier dilution gas 640 that can be configured to bypass delivery system 500. A valve 631 can be used to isolate the dilution line when desired. A pair of check valves 632, 633 can be placed downstream of MFC 620 and MFC 630 to protect them, e.g., from possible exposure to process gases (e.g., $H_2O$ or $H_2O_2$). A pressure gauge 634 can be placed between MFC 620.

The pressure of carrier gas 610 pressure can be maintained with a forward pressure regulator 635. A thermocouple 636 can measure the temperature of carrier gas 610 before it enters delivery system 500. Within delivery system 500, as described above, the gas phase of a multi-component solution can be introduced into carrier gas 610. A thermocouple 637 can measure the temperature of carrier gas 610 before passing by analyzer 660. A pressure transmitter 638 can measure the pressure of carrier gas 610 before passing by analyzer 660. A thermocouple 639 can measure the temperature of carrier dilution gas 640. A pressure gauge 641 can measure the pressure of carrier dilution gas 640 before passing through MFC 630. A valve 611 can isolate carrier gas 610 supply.

Manifold 600 can be configured to receive a water supply 670 (e.g., deionized water) into delivery system 500. The pressure of water supply 670 pressure can be maintained with a forward pressure regulator 671. A pressure gauge 672 can measure the pressure of water supply 670 before entering delivery system 500. A valve 673 can isolate water supply 670 from delivery system 500 and a valve 674 can isolate water supply 670 from forward pressure regulator 671.

Manifold 600 can further comprise a concentration analyzer 690 configured to measure the concentration of the multi-component solution within delivery system 500.

Manifold 600 as described above was utilized in the following methods according certain embodiments of the present inventions. The following methods used aqueous hydrogen peroxide solutions having a concentration between about 30% to about 50% (w/w) at a temperature of about 40° C. Delivery system 500 was configured as an HPDS employing an HPDA like membrane contactor assembly 400. The HPDA housing and endcaps were PTFE.

Figure 7:
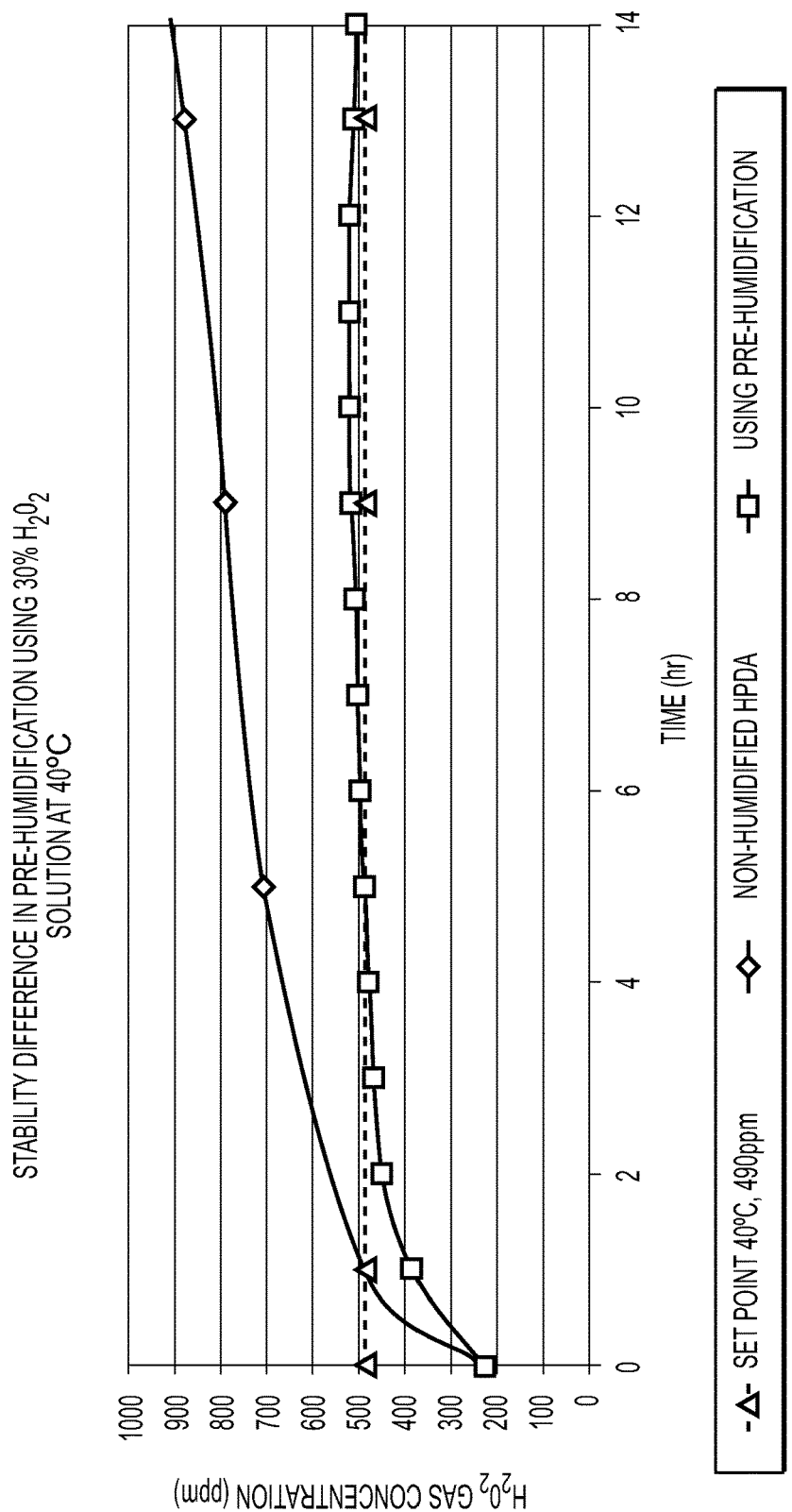
FIG. 7 is a chart depicting the concentration of $H_2O_2$ over time for a 30% $H_2O_2$ aqueous solution at about 40° C. according to certain embodiments.

In one method according to certain embodiments of the present invention, HPDS 500 was monitored while operating at a temperature of about 40° C. using a 30% $H_2O_2$ aqueous solution. For comparison, the HPDS was operated with pre-humidified nitrogen carrier gas for a period of time and with dry nitrogen carrier gas for a period of time. According to Raoult's law, the concentration of $H_2O_2$ gas was expected to be 490 ppm, which was the set point. The data collected from this procedure are depicted in FIG. 7. As shown in FIG. 7, when the pre-humidified nitrogen carrier gas was used with HPDS 500, the $H_2O_2$ concentration increased until it reached approximately the set point after about 3 hours. That $H_2O_2$ concentration was maintained for at least 11 hours, when the procedure was ended. There was no indication that the $H_2O_2$ concentration was not stable or could not be maintained for longer periods of time. By contrast, when dry (undersaturated) nitrogen carrier gas was used with HPDS 500, the $H_2O_2$ concentration increased and exceeded the set point within about one hour and then continuously increased throughout the 14-hour duration of the test. The undersaturated nitrogen gas led to an increase in the $H_2O_2$ concentration in the liquid source which, in turn, led to the increased gas-phase concentration of $H_2O_2$. By adjusting parameters such as flow rate temperature dynamically, one can select for a stable level of $H_2O_2$ concentration in the gas phase for delivery to a critical process application.

Figure 8:
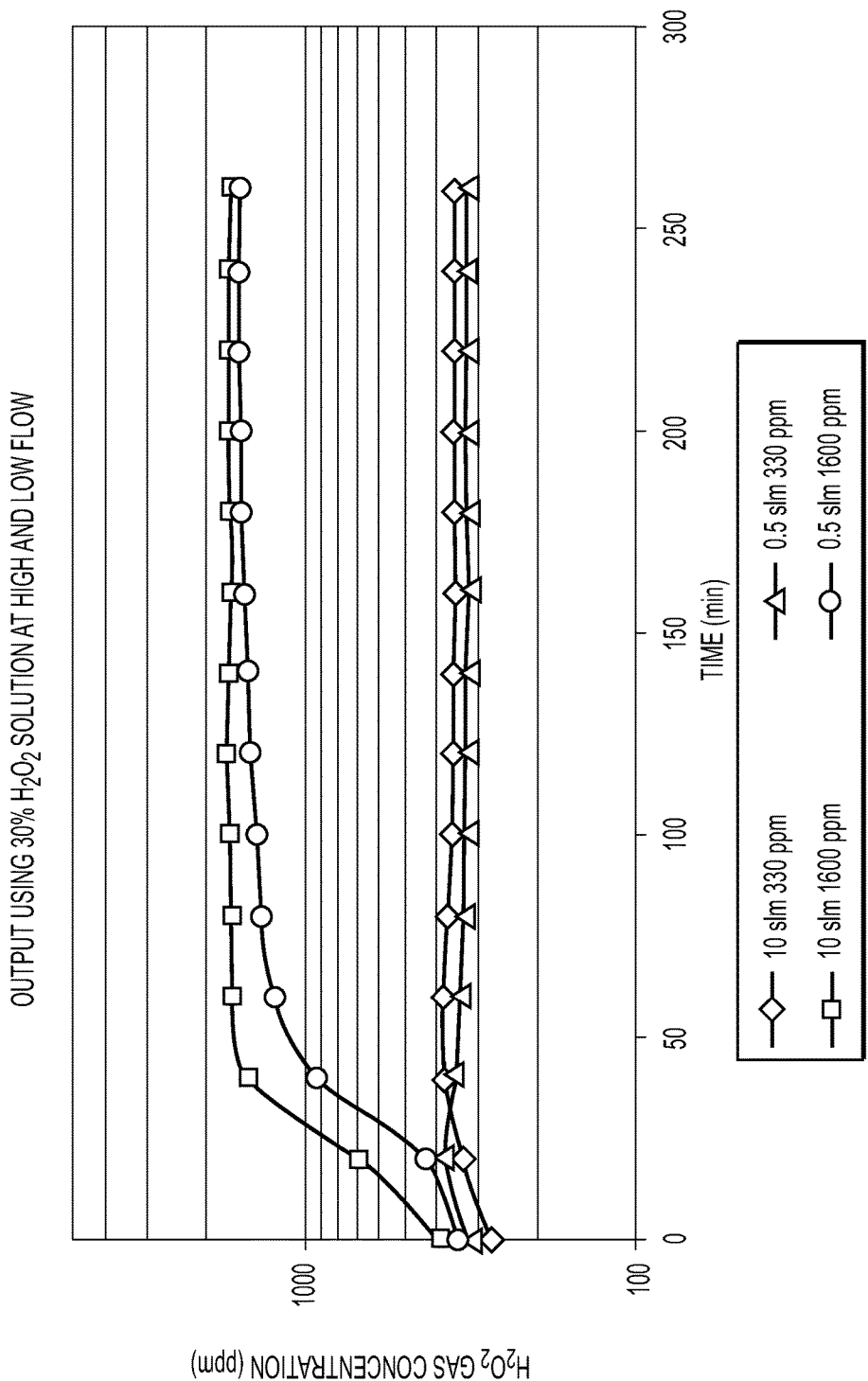
FIG. 8 is a chart depicting the concentration of $H_2O_2$ over time for a 30% $H_2O_2$ aqueous solution at different flow rates.

In another method according to certain embodiments of the present invention, HPDS 500 was monitored while operating at different concentration set points and different flow rates using a 30% $H_2O_2$ aqueous solution and pre-humidified nitrogen carrier gas. The HPDS was monitored at concentration set points of 330 ppm and 1600 ppm and flow rates, at both set points, of 0.5 slm and 10 slm. The date collected during this procedure is shown in FIG. 8. As shown in FIG. 8, in all four scenarios the $H_2O_2$ gas concentration was substantially maintained after the initial startup. The procedure was ended after about 4.5 hours. There was no indication that the $H_2O_2$ concentration was not stable or could not be maintained for longer periods of time.

Figure 9:
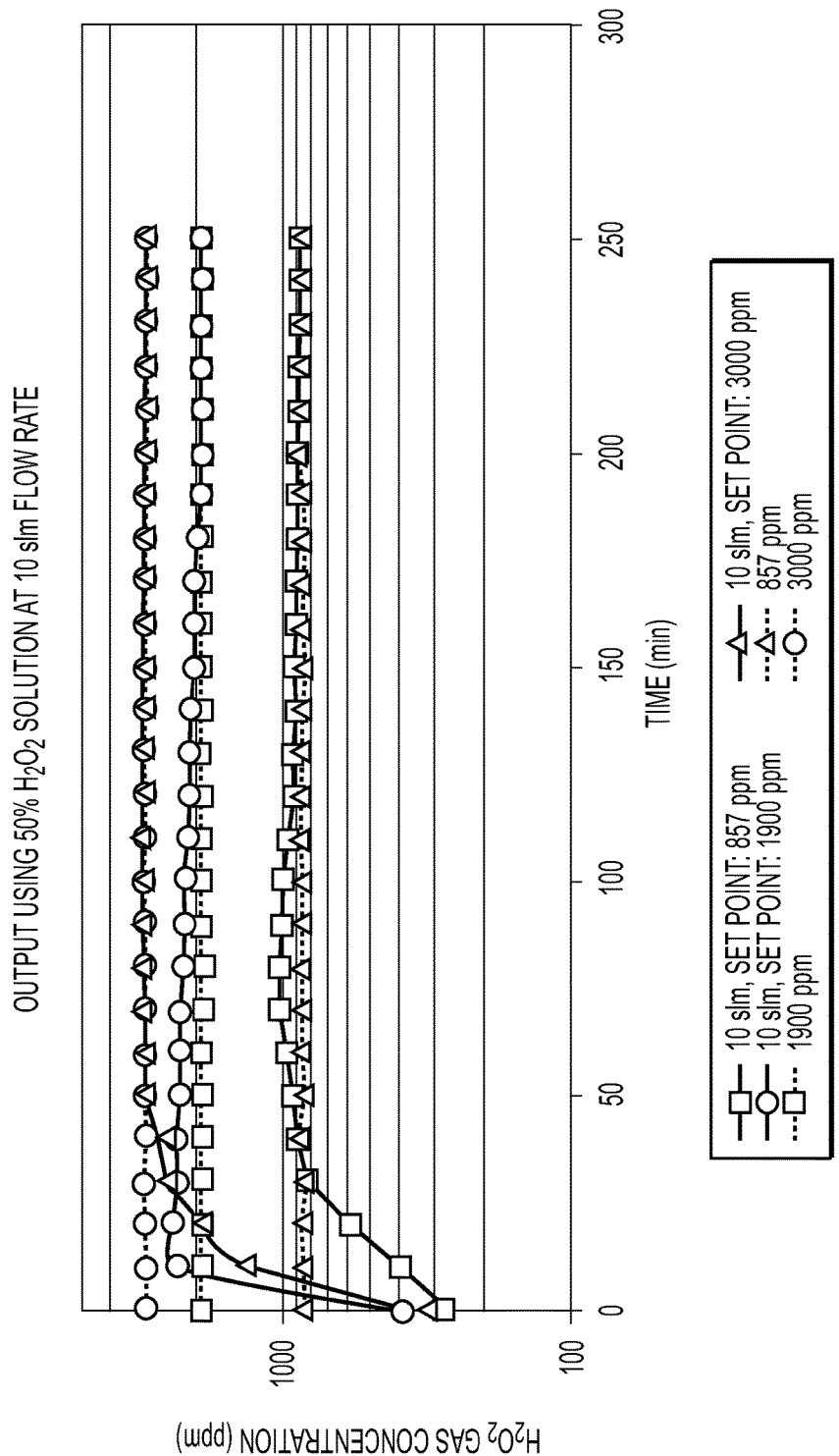
FIG. 9 is a chart depicting the concentration of $H_2O_2$ over time for a 50% $H_2O_2$ solution at different flow rates.

In another method according to certain embodiments of the present invention, an HPDS 500 containing a 50% $H_2O_2$ aqueous solution was monitored while pre-humidified nitrogen carrier gas was made to flow through the HPDS at a flow rate of 10 slm. The HPDS was monitored at three different $H_2O_2$ gas concentration set points: 857 ppm, 1900 ppm, and 3000 ppm. The data collected during this procedure is shown in FIG. 9. As shown in FIG. 9, even at the higher concentration and high flow rate, the HPDS was able to maintain the $H_2O_2$ concentration at each set point.

As discussed above, the amount of the high volatility component (e.g., water) that should be present in the carrier gas necessary to maintain a stable concentration of the lower volatile component in the multi-component liquid source may be approximated based on Raoult's Law as P (preloada)=xa(Pa−Pb). But this approximation is based on the idealized Raoult's Law and most solutions are non-ideal. Correction factors for the non-ideal behavior of real multi-component solutions can be applied. In certain embodiments, it will be advantageous to pre-determine the amount of the high volatility component in the carrier gas that is required for a certain process and, thus, to calculate the approximate setpoints for the humidifier and membrane contactor assembly.

Figure 10:
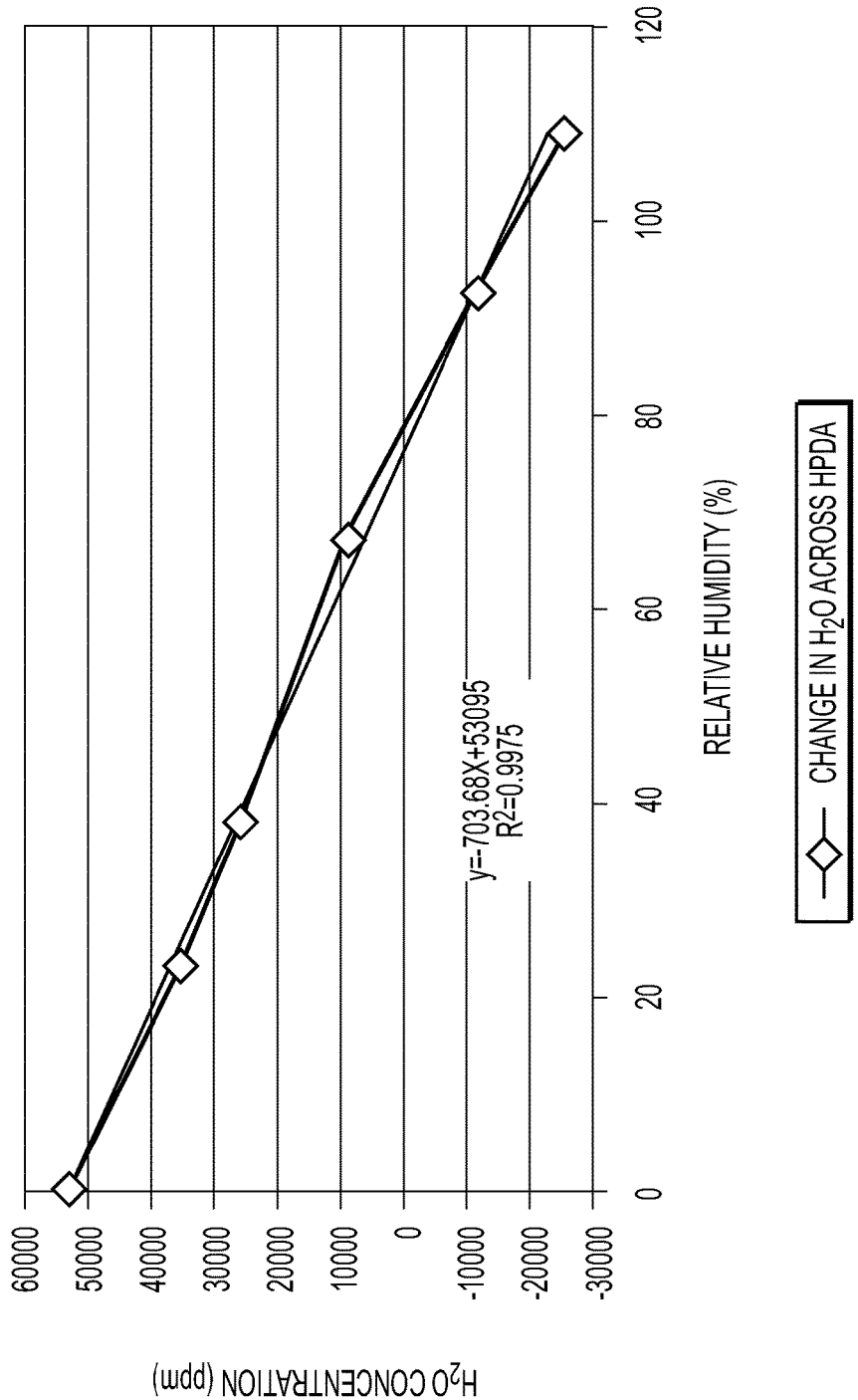
FIG. 10 is a chart plotting the relative humidity measured downstream of the humidifier and upstream of an HPDA shown against the change in $H_2O$ concentration in the gas stream; namely, the difference in $H_2O$ concentration measured before and after the gas stream passed through the HPDA.

For example, a comparison of the change in water concentration of the pre-loaded/humidified carrier gas after passing through an HPDA to the relative humidity of the pre-loaded/humidified carrier gas is shown by reference to the data in FIG. 10. The data was obtained by adding a relative humidity probe to the delivery system of FIG. 3. A relative humidity probe was added immediately downstream of humidifier 310. The amount of $H_2O_2$ and water after the membrane contactor assembly 320, which was configured as an HPDA, was then measured. The difference in water and $H_2O_2$ before and after HPDA 320 were used to adjust the temperature setpoints for humidifier 310 and HPDA 320. By reference to the analogous items in FIG. 5, changing the temperature setpoints of the humidifier and HPDA can be accomplished by adjusting the temperature setpoints of heaters 504 and 509 through dewpoint probe 503 and thermocouple 510. By using experimentally collected data, the exact temperature setpoints and preload dewpoints needed can be collected and stored for calibration of the specific device.

FIG. 10 plots the flux of water across the HPDA membranes against the relative humidity of the pre-loaded/humidified carrier gas entering the HPDA. As the water concentration of pre-loaded/humidified carrier gas was increased from 0% RH to 110% RH, the flux of water across the HPDA membranes decreases. In this example, between 0% RH and about 75% RH, water was removed from the HPDA, i.e., the flux was positive. Above about 75% RH in this example, water was added to the HPDA from the pre-loaded/humidified carrier gas the membrane into the hydrogen peroxide aqueous solution, thereby diluting the concentration of the solution.

Figure 21:
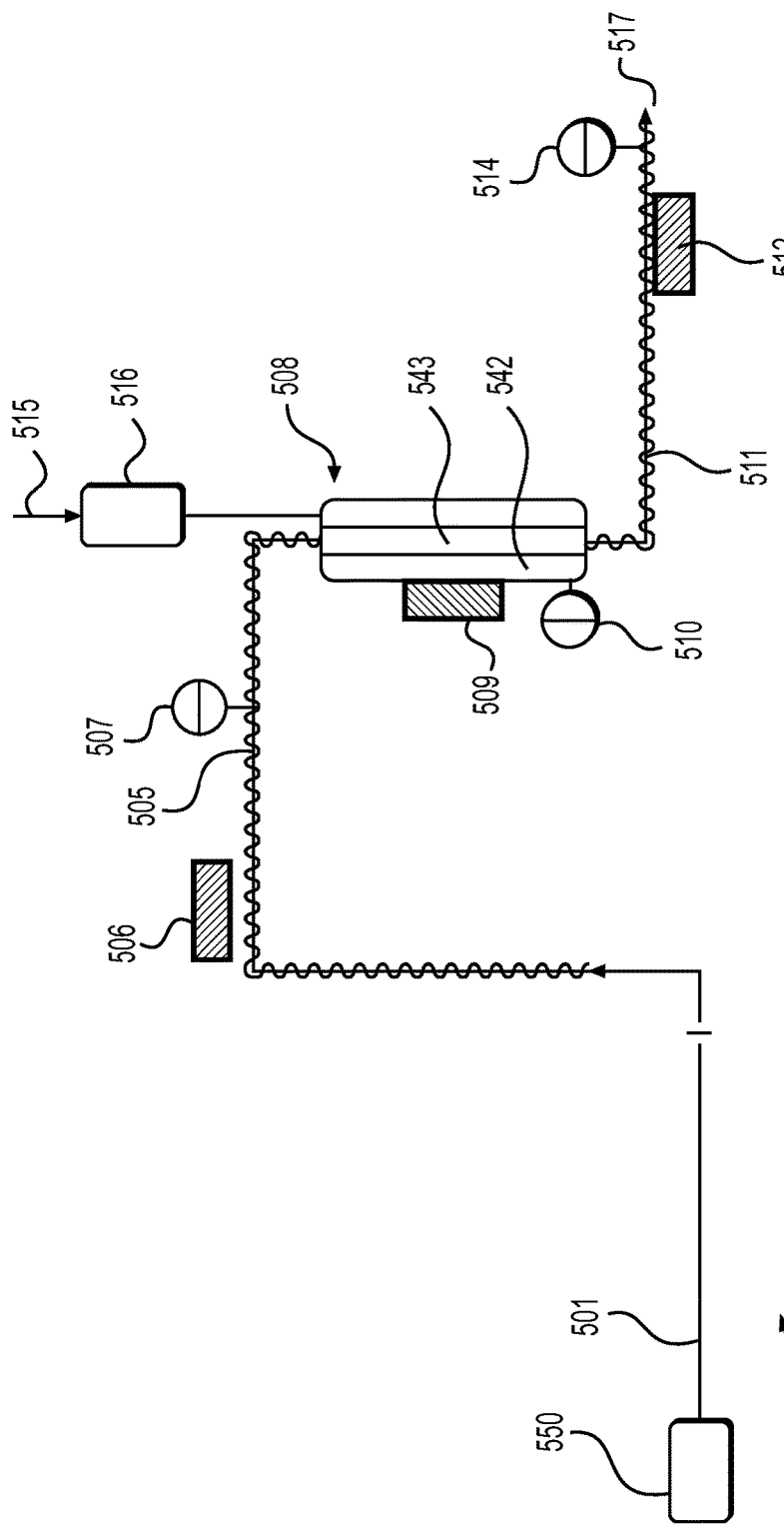
FIG. 21 is a P&ID of a delivery system according to certain embodiments of the present invention.

FIG. 21 shows a P&ID of certain embodiments of the invention for a delivery system 500A for delivering a low volatility component, e.g., hydrogen peroxide, of a multi-component liquid solution, e.g., an aqueous hydrogen peroxide solution. When configured as a hydrogen peroxide delivery system (HPDS), delivery system 500A can comprise a carrier gas 550 in fluid communication with an HPDA 508, e.g., a membrane. In such configuration, delivery system 500A can be configured to receive a carrier gas 550 through a gas tubing 501.

The temperature of the carrier gas can be maintained or changed by heating gas tube 505 with heater 506, The temperature can be measured and controlled with thermocouple 507. The temperature setpoint of heater 506 can be adjusted in order to limit condensation of water from the carrier gas.

Carrier gas can then flow into membrane contactor assembly 508, which can be an HPDA. Membrane contactor assembly 508 can comprise a plurality of membrane lumens 543 and a multi-component solution 542 (e.g., aqueous hydrogen peroxide solution) contained within the shell of membrane contactor assembly 508. Carrier gas can flow into membrane lumens 543 where multi-component solution 542 is volatized through membrane lumens 543. The concentration of gas from the multi-component solution entering the carrier gas can be controlled through thermal regulation. The temperature of the multi-component solution can be controlled with a heater 509, and the temperature of the multi-component solution can be measured with thermocouple 510. The concentration of components of the multi-component solution in the gas phase can be increased or decreased to a setpoint by increasing or decreasing the setpoint of heater 509.

The carrier gas exiting membrane contactor assembly 508 through gas tube 511 contains both components of the multi-component solution in the gas or gas phase as the case may be. The temperature of that carrier gas can be controlled using a heater 512 and a thermocouple 514. Heater 512 can wrap around gas tube 511. That carrier gas, which contains the desired low volatility component can be delivered to a process throughout outlet 517.

The multi-component solution 542 contained in membrane contactor assembly 508 can be filled and replenished through fill tube 515, which fills membrane contactor assembly 508 and then a reservoir 516. In one embodiment, this replenishment occurs so that the volume of multi-component solution 542 remains approximately constant. Reservoir 516 can serve the purpose of maintaining level of multi-component solution 542 in membrane contactor 508 for longer periods of time.

Figure 22:
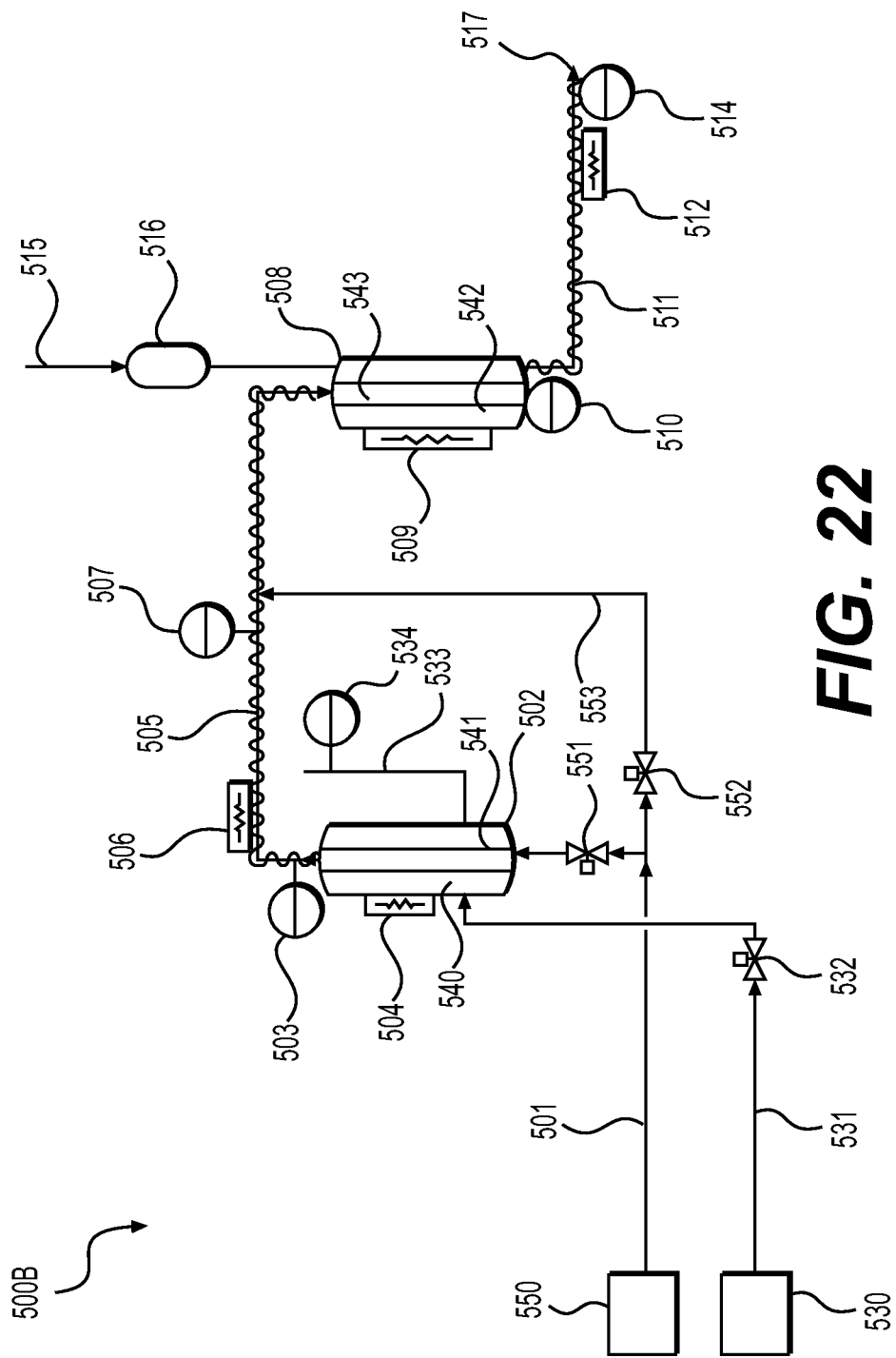
FIG. 22 is a P&ID of a delivery system according to certain embodiments of the present invention.

FIG. 22 shows a P&ID of certain embodiments of the invention for a delivery system 500B for delivering a low volatility component, e.g., hydrogen peroxide, of a multi-component liquid solution, e.g., an aqueous hydrogen peroxide solution with a bypass line fitted in. When configured as a hydrogen peroxide delivery system (HPDS), delivery system 500 can comprise a humidifier 502 in fluid communication with an HPDA 508, e.g., a membrane. In such configuration, delivery system 500 can be configured to receive a carrier gas 550 into humidifier 502 through a gas tubing 501. Carrier gas 550 can flow into a plurality of membranes 541 within humidifier 502. Valve 551 may be used to shut off flow to humidifier 502 thus bypassing it through gas line 553. The bypass may be diverted back to the humidifier with valve 552.

Dry carrier gas from gas tubing 501 can be diverted to bypass the humidifier 502 by closing valve 551 and opening valve 552. The dry carrier gas exits gas tubing 501 through valve 552. Then the dry carrier gas exits gas tubing 553 into gas tube 505. The dry carrier gas then exits gas tube 505 and enters into membrane contactor assembly 508.

When the dry carrier gas is not diverted, humidifier 502 can be configured to receive a water source 530 (e.g., DI water) through a water tubing 531 into water/gas chamber 540 within humidifier 502. Humidifier 502 can be configured to increase the moisture content of carrier gas 550 flowing through membranes 541. The moisture concentration of the pre-loaded/humidified carrier gas exiting humidifier 502 can be controlled by a heater 504 and a dewpoint probe 503. The moisture concentration of the pre-loaded/humidified carrier gas can be increased or decreased to a setpoint by increasing or decreasing the temperature setpoint of heater 504. By changing the setpoint, one can provide a carrier gas that is undersaturated, saturated, or oversaturated with humidity. The flow rate of the carrier gas can also be changed to alter the saturation of the carrier gas.

When valve 551 is open, pre-loaded/humidified carrier gas can exit humidifier 502 into a gas tube 505. The temperature of the carrier gas can be maintained above the dew point by heating gas tube 505 with heater 506, and the temperature can be measured and controlled with thermocouple 507. Alternatively, the temperature of the carrier gas can be maintained below the dew point by selectively heating gas tube 505 with heater 506, and the temperature can be measured and controlled with thermocouple 507. The temperature setpoint of heater 506 can be greater than the temperature setpoint of heater 504 in order to limit condensation of water from the pre-loaded/humidified carrier gas. Alternatively, by setting the temperature of heater 506 so that it is less that the temperature setpoint of heater 504, one can create an undersaturated pre-loaded/humidified carrier gas.

Pre-loaded/humidified carrier gas can then flow into membrane contactor assembly 508, which can be an HPDA. Membrane contactor assembly 508 can comprise a plurality of membrane lumens 543 and a multi-component solution 542 (e.g., aqueous hydrogen peroxide solution) contained within the shell of membrane contactor assembly 508. Pre-loaded/humidified carrier gas can flow into membrane lumens 543 where multi-component solution 542 is volatized through membrane lumens 543. The concentration of gas from the multi-component solution entering the pre-loaded/humidified carrier gas can be controlled through thermal regulation. The temperature of the multi-component solution can be controlled with a heater 509, and the temperature of the multi-component solution can be measured with thermocouple 510. The concentration of components of the multi-component solution in the gas phase can be increased or decreased to a setpoint by increasing or decreasing the setpoint of heater 509.

The carrier gas exiting membrane contactor assembly 508 through gas tube 511 contains both components of the multi-component solution in the gas or gas phase as the case may be. The temperature of that carrier gas can be controlled using a heater 512 and a thermocouple 514. Heater 512 can wrap around gas tube 511. That carrier gas, which contains the desired low volatility component can be delivered to a process throughout outlet 517.

The water level in humidifier 502 can be maintained through automatic filling. As the water in humidifier 502 is transferred into carrier gas 550 the water level can drop. When the level drops below a set level sensed by fill sensor 534 located on a water level leg 533, a valve 532 can open to allow water to flow into humidifier 502. The water level can rise in the humidifier 502 up to a set level sensed by fill sensor 534. When the water level reaches the set level of fill sensor 534, valve 532 can close.

The multi-component solution 542 contained in membrane contactor assembly 508 can be filled and replenished through fill tube 515, which fills membrane contactor assembly 508 and then a reservoir 516. This can be accomplished automatically in a manner similar to humidifier 502. In one embodiment, this replenishment occurs so that the volume of multi-component solution 542 remains approximately constant. Reservoir 516 can serve the purpose of maintaining level of multi-component solution 542 in membrane contactor 508 for longer periods of time.

When valve 552 is open and valve 551 is closed, the apparatus in FIG. 22 may operate in the same manner as in FIG. 21.

By the approach described herein, the molar ratio of hydrogen peroxide and water in the solution used for replenishing the aqueous hydrogen peroxide source can be the same as the molar ratio of these constituents in the resulting gas phase. For example, flowing a carrier gas through a gas phase of an aqueous hydrogen peroxide source to remove the gas phase containing the hydrogen peroxide can preferentially remove water, and reduce the initial volume of the aqueous hydrogen peroxide source. Using a substantially dry carrier gas accelerates removal of water from the aqueous hydrogen peroxide source. The hydrogen peroxide concentration in the remaining volume of the aqueous hydrogen peroxide source will increase as a consequence. Replenishing the partially depleted aqueous hydrogen peroxide source by adding an aqueous hydrogen peroxide solution, for example to maintain an essentially constant volume, provides a way to stabilize the molar ratio of hydrogen peroxide and water in the resulting combined gas phase (i.e., the gas mixture resulting from the carrier continuously sweeping away the gas phase generated by the aqueous hydrogen peroxide source). Importantly, the maintained constant volume can be the initial volume of the aqueous hydrogen peroxide source, or a lesser volume. Thus, hydrogen peroxide gas generated as a result of the carrier gas contacting the aqueous hydrogen peroxide source can be delivered in a stable steady-state concentration when the aqueous hydrogen peroxide source is maintained at a constant volume by addition of an aqueous hydrogen peroxide solution having a hydrogen peroxide concentration lower than the aqueous hydrogen peroxide source at the time the replenishing solution is added.

Generally speaking, by adjusting temperature and carrier gas flow conditions, the steady-state concentration of $H_2O_2$ delivered by the disclosed apparatus and method easily can be adjusted. For example, when the aqueous hydrogen peroxide source that provides a gas phase in accordance with the invention is maintained at about 86.3° C., and when the carrier gas flow rate is 5 slm, the outputted gas phase concentration of hydrogen peroxide was measured to be 50,395 ppm. Other values can be obtained by changing, for example temperature and/or flow rate. For use in decontamination procedures, stable steady-state gas phase hydrogen peroxide concentrations can be used in the range of from about 500 ppm to about 300,000 ppm, including ranges in between including from about 500 ppm to about 800 ppm. Other ranges include about 1 ppb to 1000 ppm, about 1000 ppm to about 5,000 ppm, about 5,000 ppm to about 15,000 ppm and about 15,000 ppm to about 60,000 ppm.

The methods, systems, and devices according to certain embodiments of the present invention can self-adjust to a predetermined setpoint. If the temperature setpoints of the preload chemical and the multicomponent liquid source are initially incorrect, the concentration of the multi-component liquid source will self-adjust to the temperature-dependent concentration setpoint by either absorbing the high volatility component from the carrier gas to dilute the multi-component solution or adding the high volatility component to carrier gas to concentrate the multi-component solution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

Example 1 describes a procedure in which the initial hydrogen peroxide concentration of 31.3% in an aqueous hydrogen peroxide source was increased to a higher second concentration of 60.0% following contact between a carrier gas and the gas phase of the aqueous hydrogen peroxide source. Thereafter, an aqueous hydrogen peroxide solution that included hydrogen peroxide at a third concentration was added to the aqueous hydrogen peroxide source (to refill or replenish the aqueous hydrogen peroxide source). In this Example, the concentration of added hydrogen peroxide at the third concentration was the same as the initial concentration in the aqueous hydrogen peroxide source. Subsequent Examples describe variations on these parameters.

Example 1

General Procedure to be Used for Concentrating Peroxide

The following procedure may be used to concentrate a 31.3% $H_2O_2$ solution to a 60.0% solution in 112 minutes. The liquid bath temperature of a solution of 31.3% $H_2O_2$ solution in an HPDS may be set to 79.0° C. and the dew point may be set to 72.2° C. for the incoming carrier gas containing nitrogen and water. An Anton-Paar Density Meter may be used to measure the concentration of hydrogen peroxide in the solution. The HPDS is set up to refill the bath solution to maintain a constant volume using the same initial 31.3% $H_2O_2$. The dewpoint values as a function of time for the procedure are as set forth in Table 1. All concentrations in the examples, unless otherwise specified, are by weight percent.

TABLE 1

Dew Point Set Point Profile

| Time (min) | 0 | 27.5 | 57.5 | 112.0 |
|---|---|---|---|---|
| Dewpoint Set Point | 55.0° C. | 45.0° C. | 35.0° C. | 52.0° C. |

Figure 11:
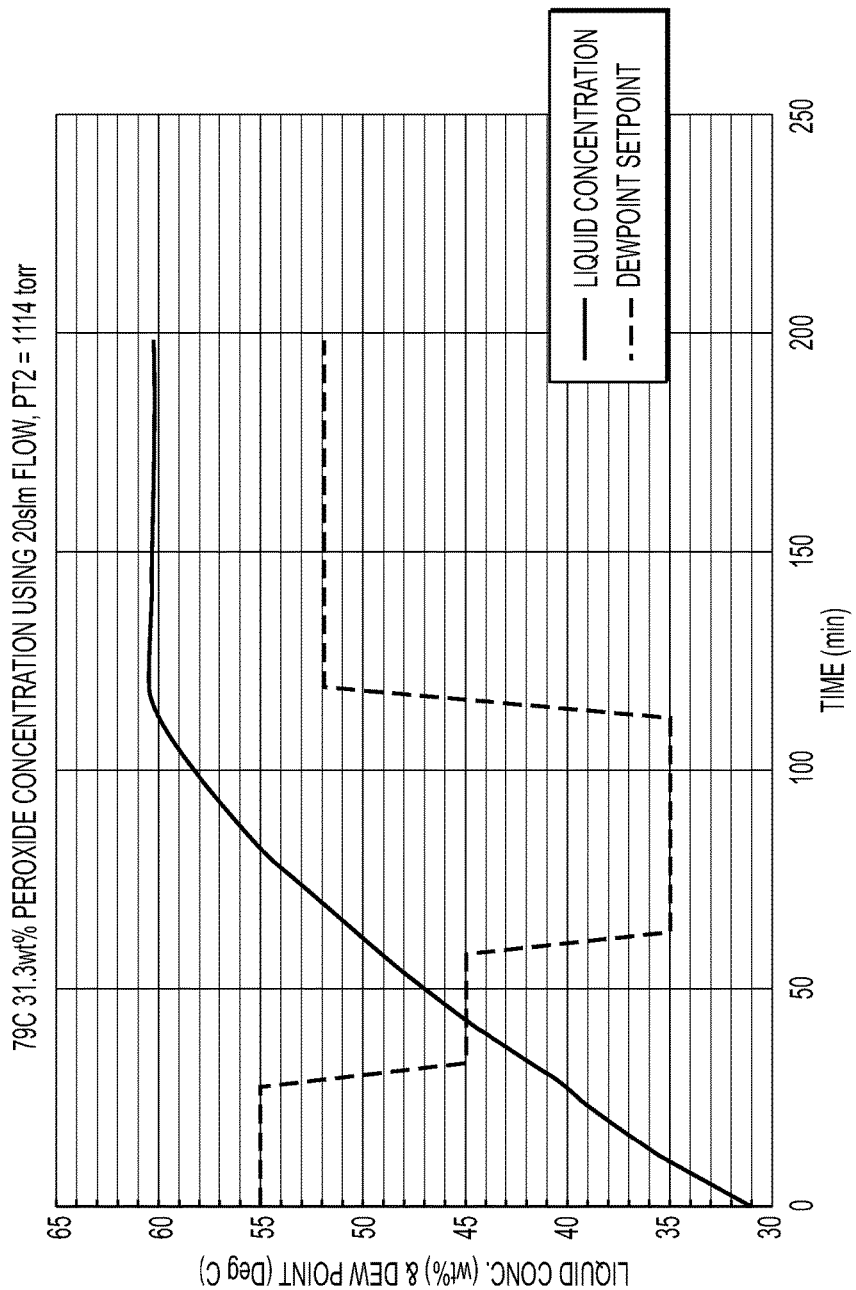
FIG. 11 is a graph of a theoretical HPDA liquid peroxide concentration vs. time.

At 60, 112, and 172 minutes, 2 mL samples from the peroxide in solution were pulled to check the concentration. FIG. 11 illustrates a theoretical HPDA liquid peroxide concentration vs. time.

Example 2

Concentrating Peroxide

Figure 12:
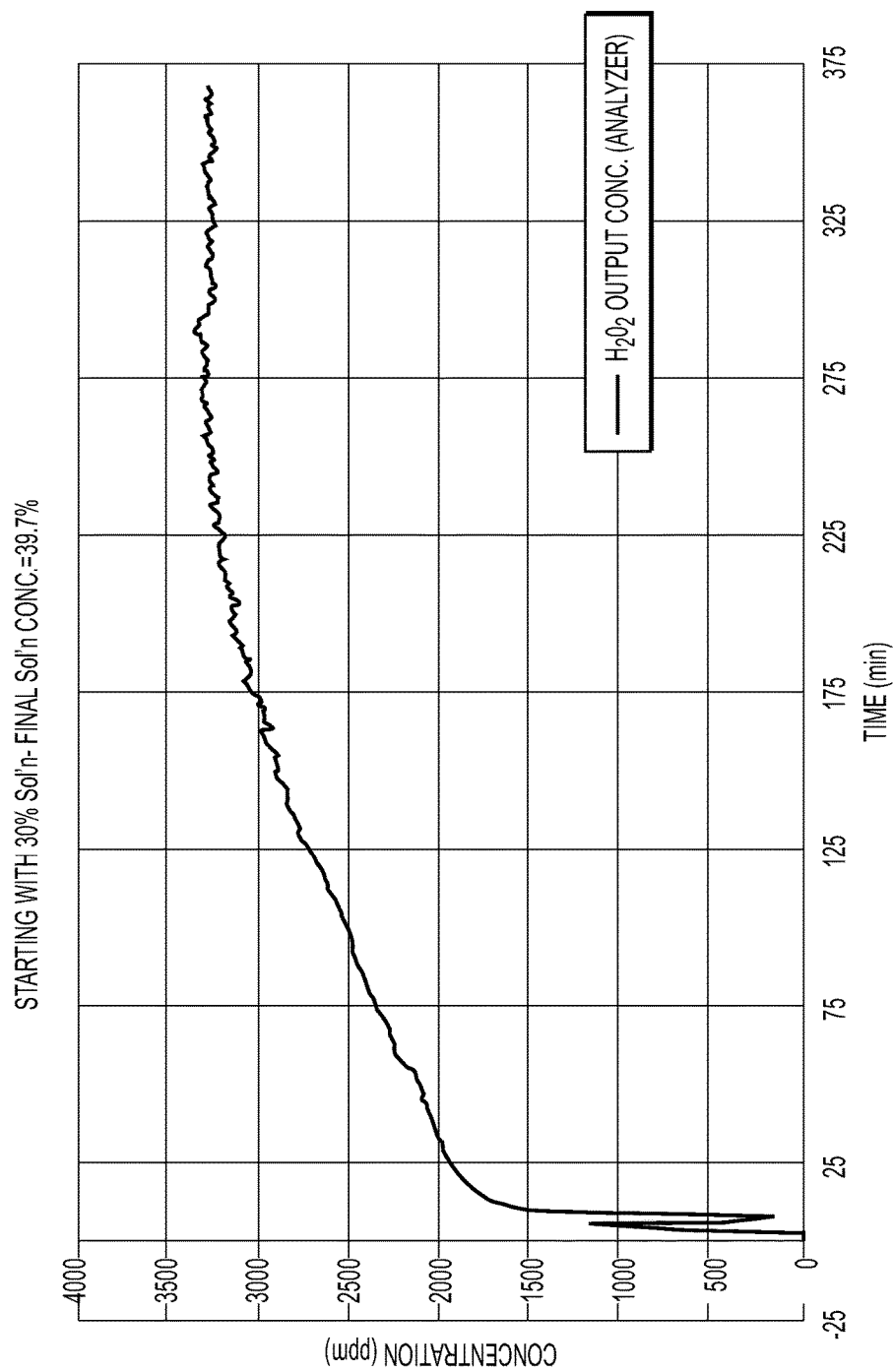
FIG. 12 is a graph of a peroxide gas output curve.

The dew point of the preload carrier gas was set 10 degrees below its original setpoint using a procedure as set forth in Example 1. The dew point was about 62.3° C., 10 degrees below what it would have been if the goal had been maintaining solution concentration the same throughout the test. Replenishment was with the same initial concentration peroxide solution. The carrier gas was set to 20 slm of nitrogen and the $H_2O_2$ output was set to 3430 ppm. The final gas output was around 3266 ppm, and final solution concentration was about 39.7% as seen in FIG. 12.

Example 3

Concentrating Peroxide

Figure 13:
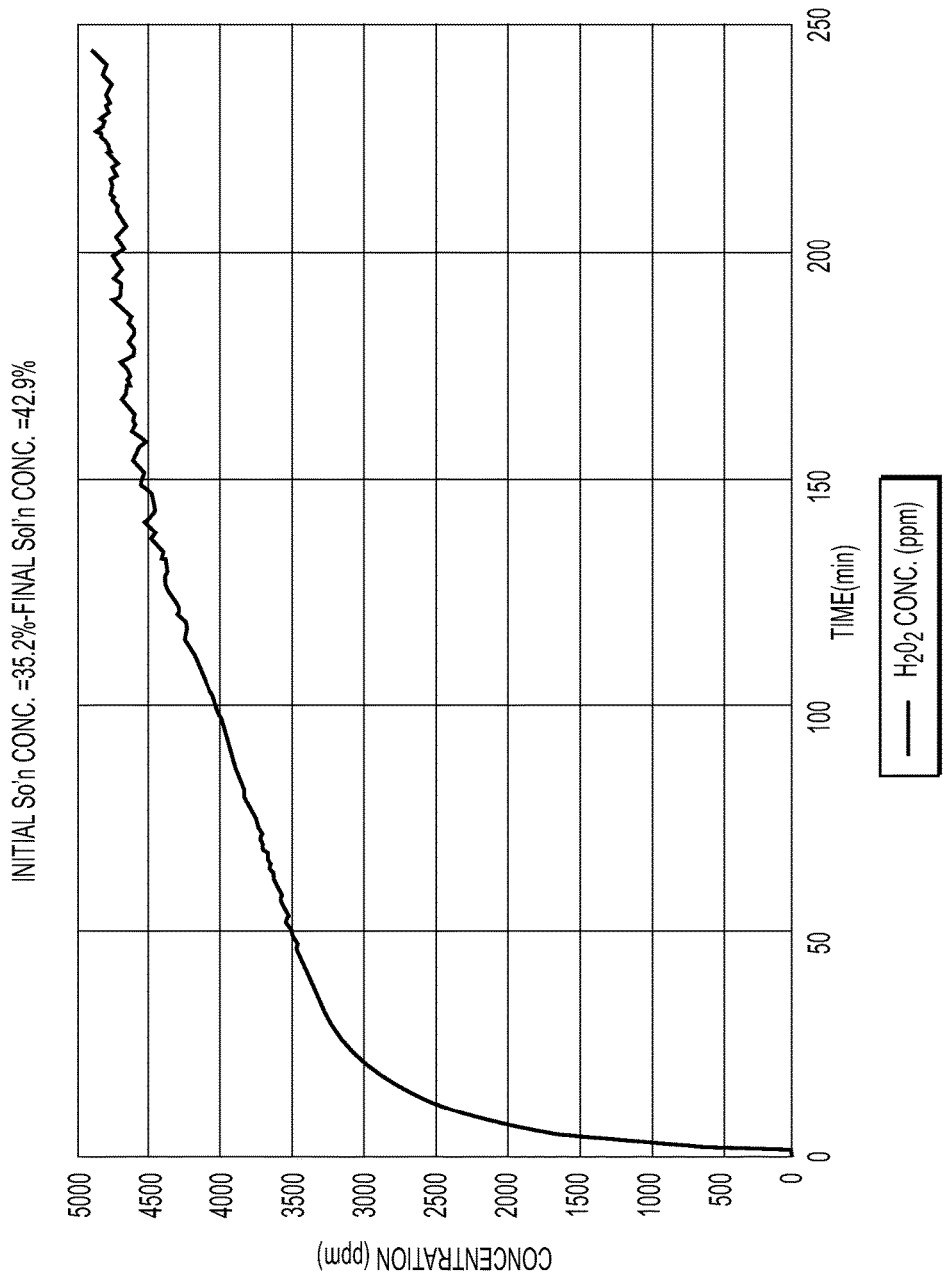
FIG. 13 is a graph of a peroxide gas output curve.

Using the procedure of Example 1, starting with a 35% $H_2O_2$ solution, and a $H_2O_2$ output was set to 4500 ppm. Replenishment was with the same initial concentration peroxide solution. FIG. 13 shows the output for the example which is a concentration of 42.9% in solution. For this example, the dew point was set to 60.9° C. The final output of peroxide in the gas phase was about 4800 ppm. The carrier gas for this test was 10 slm of $N_2$.

Example 4

Stabilized Peroxide Delivery

Figure 14:
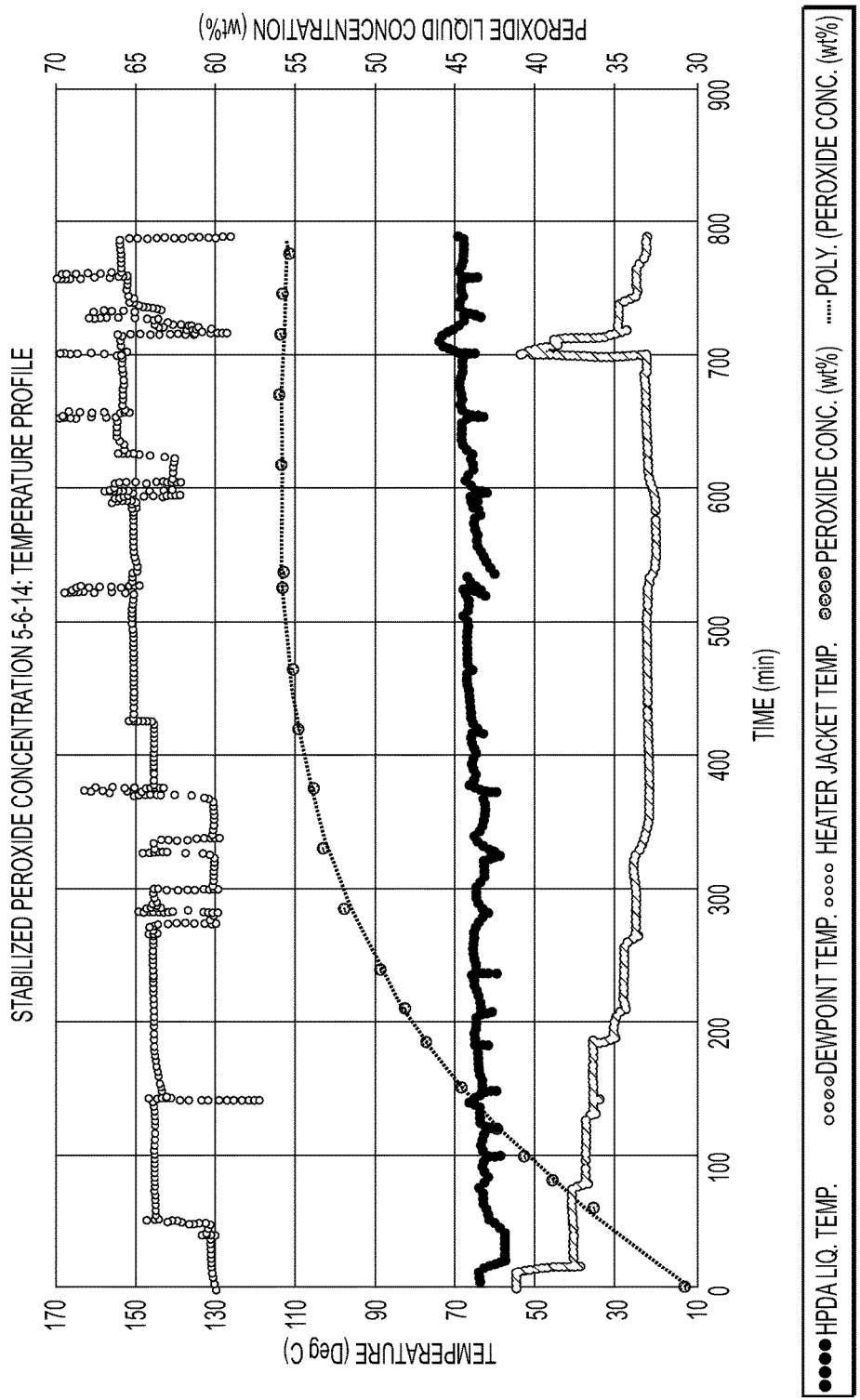
FIG. 14 is a stabilized peroxide concentration temperature profile.
Figure 15:
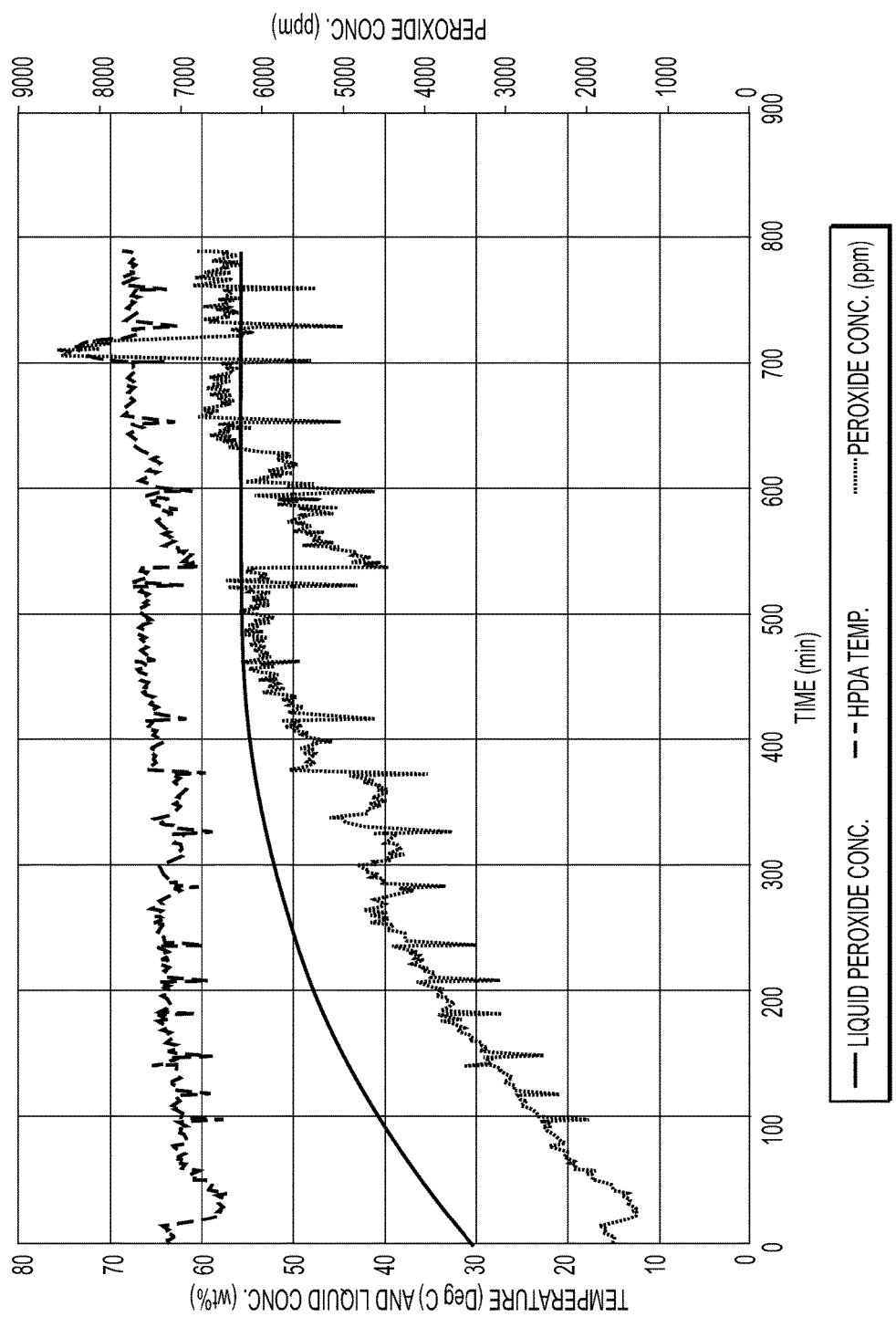
FIG. 15 is a peroxide liquid/gas concentration and HPDA temperature profile.

Using the general procedure of Example 1, but starting with 30.8% $H_2O_2$ and running a 20 slm nitrogen flow rate, the HPDA bath concentration was concentrated from 30.8% to 56.3% over a 540 minute period. Replenishment was with the same initial concentration peroxide solution. The 56.3% concentration peroxide was stabilized over a 240 minute period to ensure that stabilized peroxide delivery is possible. FIG. 14 displays temperature profiles and HPDA liquid concentration over the two day test duration. FIG. 15 shows the theoretical $H_2O_2$ concentration in the gas phase.

Example 5

Stabilized Peroxide Delivery

Figure 16:
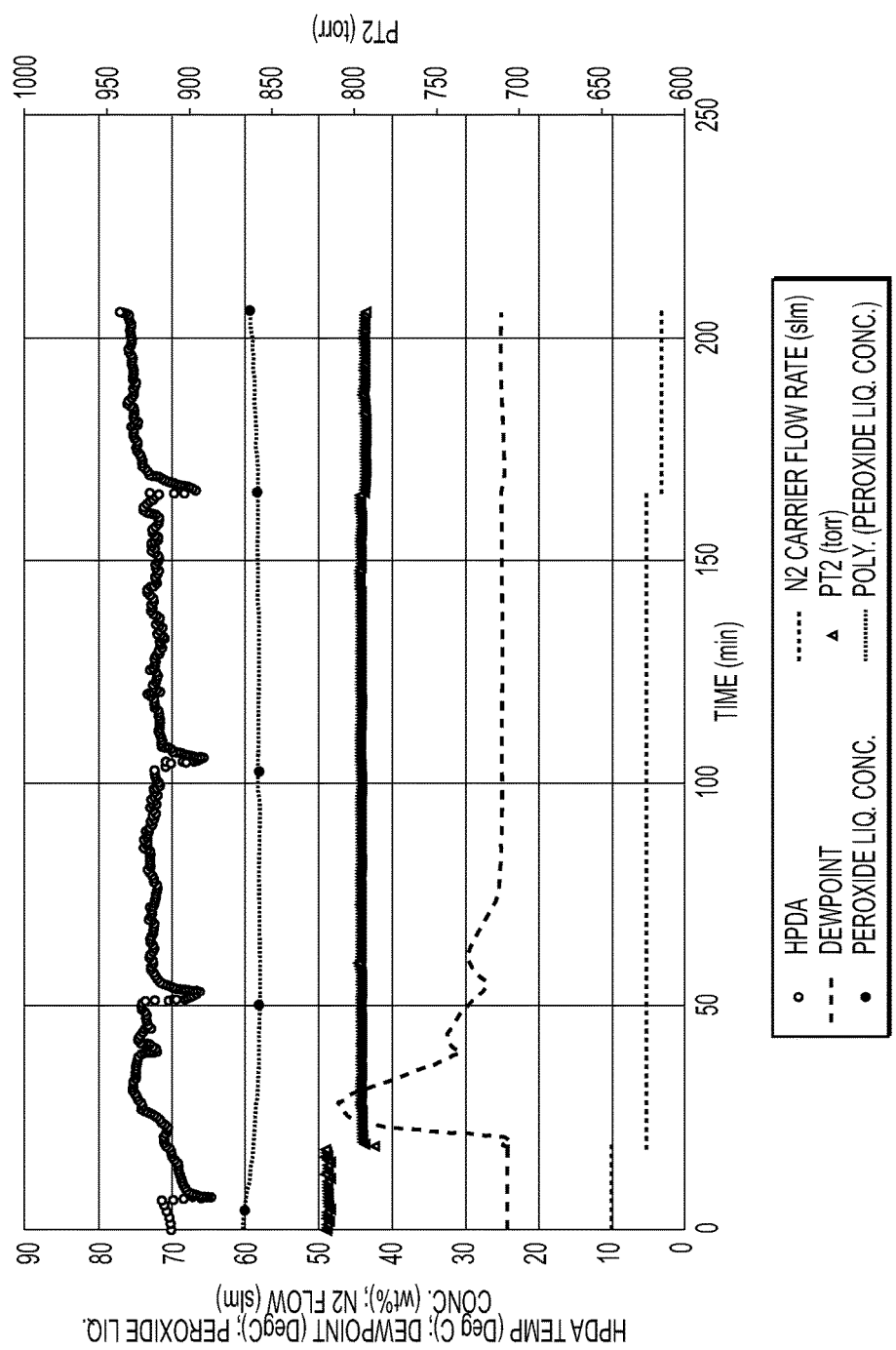
FIG. 16 is a temperature/pressure profile and HPDA liquid concentration.
Figure 17:
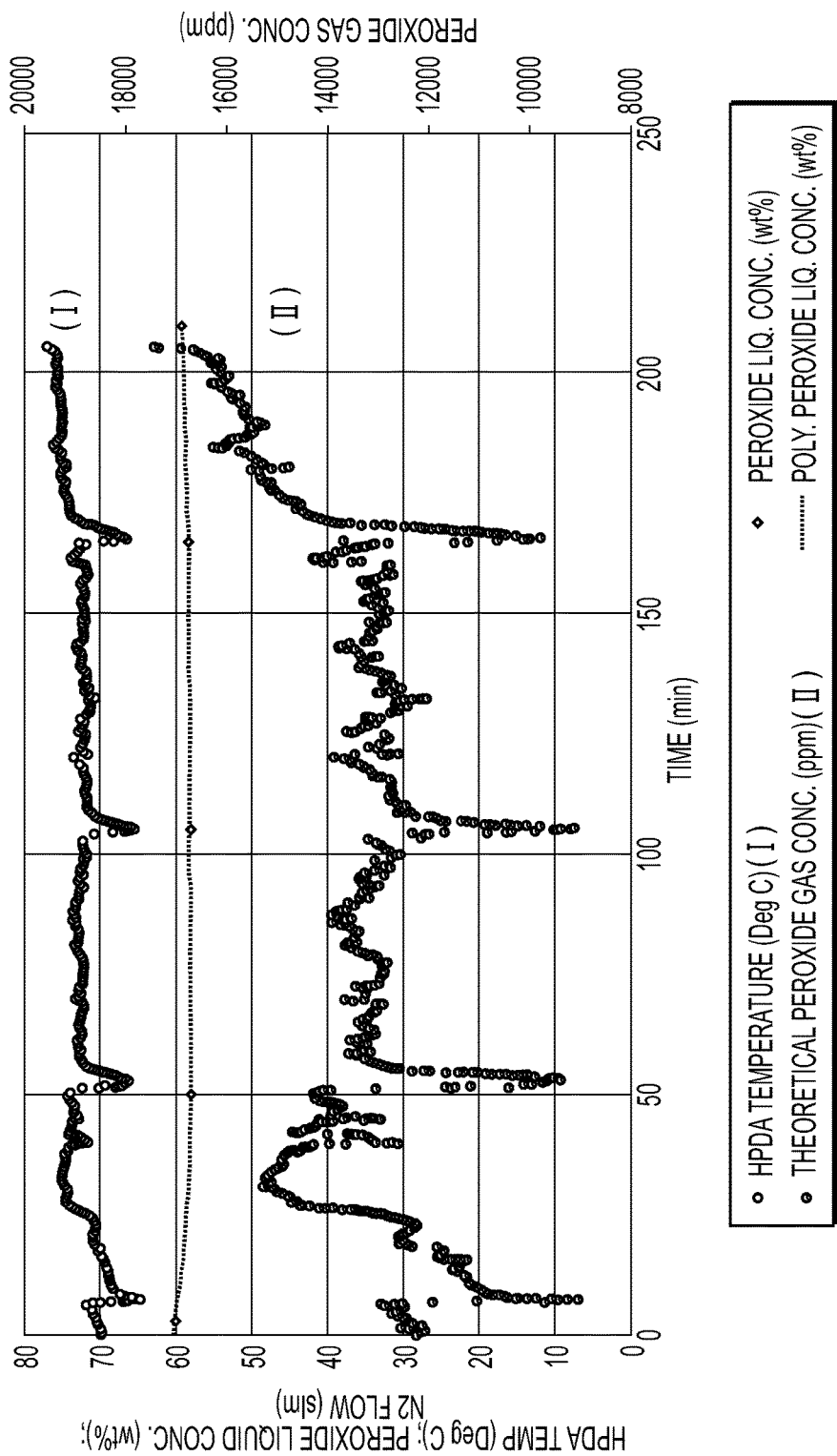
FIG. 17 is a graph of a HPDA temperature and peroxide concentration curve.

The following stabilized gas delivery experiment was run over a 210 minute period using a 31.4% peroxide liquid source and increased the concentration to an HPDA peroxide concentration of about 60.0% which was maintained over a 210 minute duration plus or minus 2%. This resulted in a peroxide gas output concentrations between 12000-17000 PPM. Replenishment was with the same initial concentration peroxide solution. FIG. 16 displays temperature and pressure profiles and HPDA liquid concentration over the test duration. The downward spikes in HPDA temperature occur every time a 4 mL liquid peroxide sample is taken. FIG. 17 displays the peroxide gas output concentration profile vs time. The downward spikes in HPDA temperature cause downward spikes in the peroxide output. If the system were to run without sampling these downward peaks would not be present. The measurements of peroxide gas concentration are indirectly derived from Raoult's law based on known composition and temperature.

Example 6

Stabilized Peroxide Delivery

Figure 18:
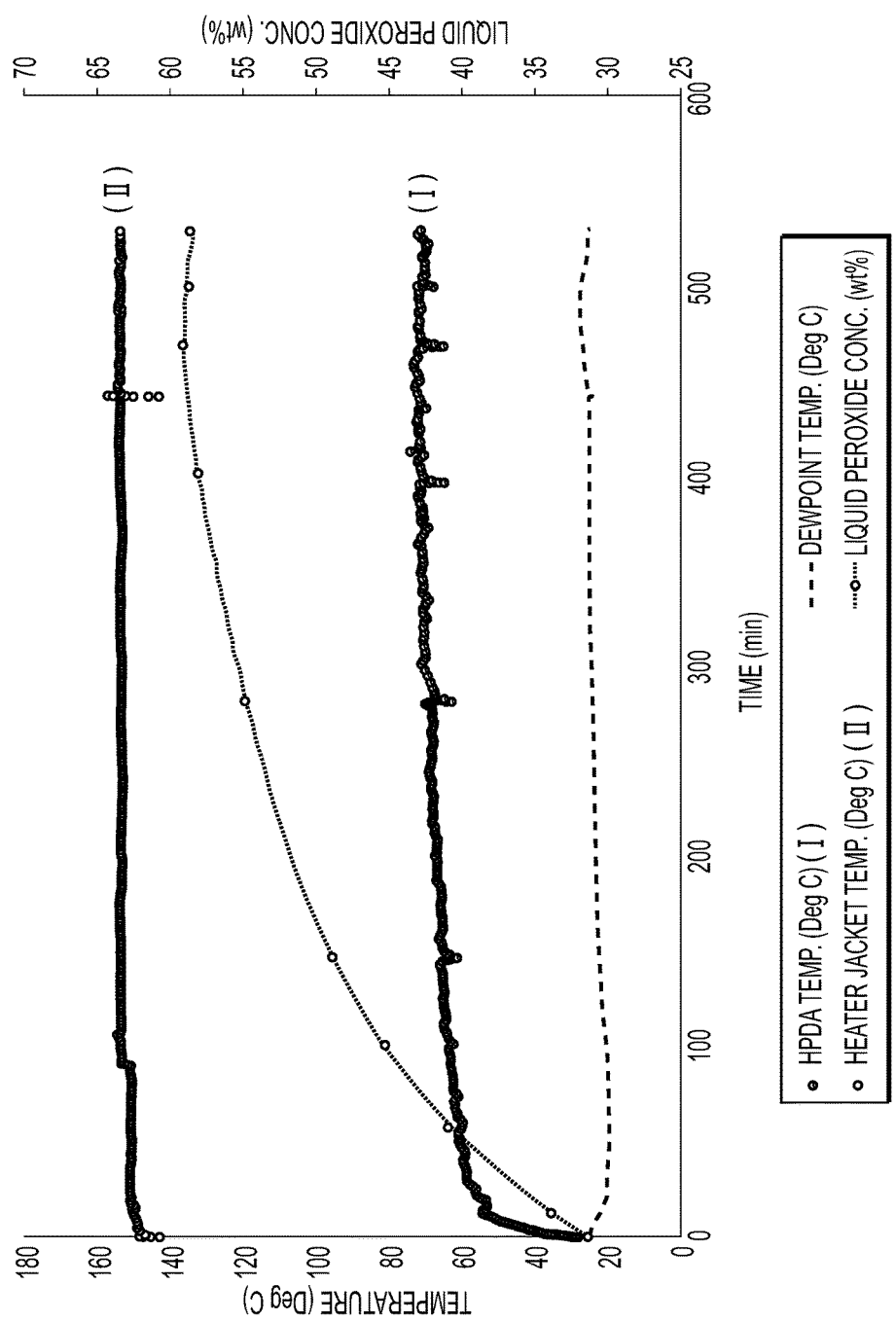
FIG. 18 is a temperature profile and peroxide liquid concentration graph.
Figure 19:
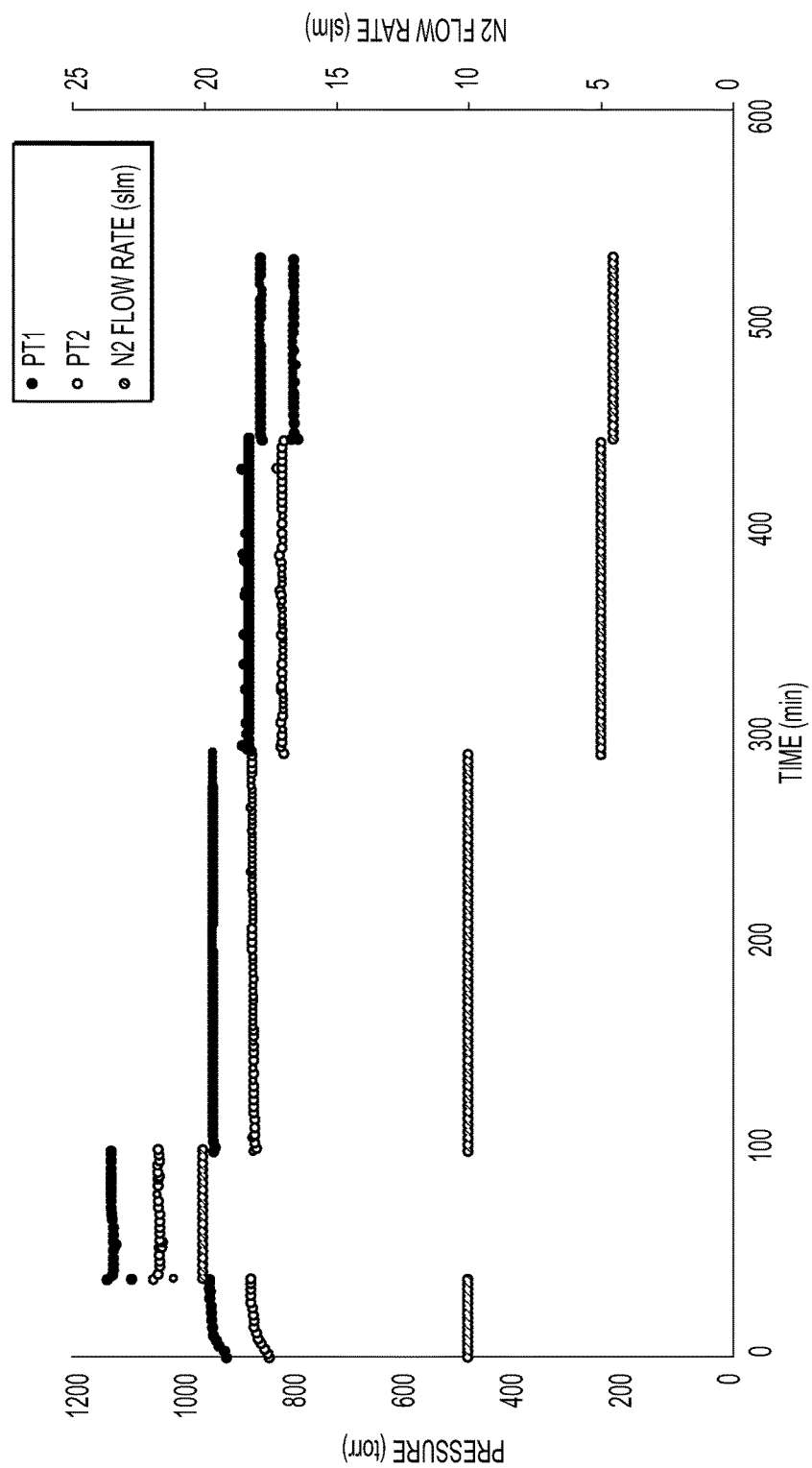
FIG. 19 is a graph showing nitrogen flow rate.
Figure 20:
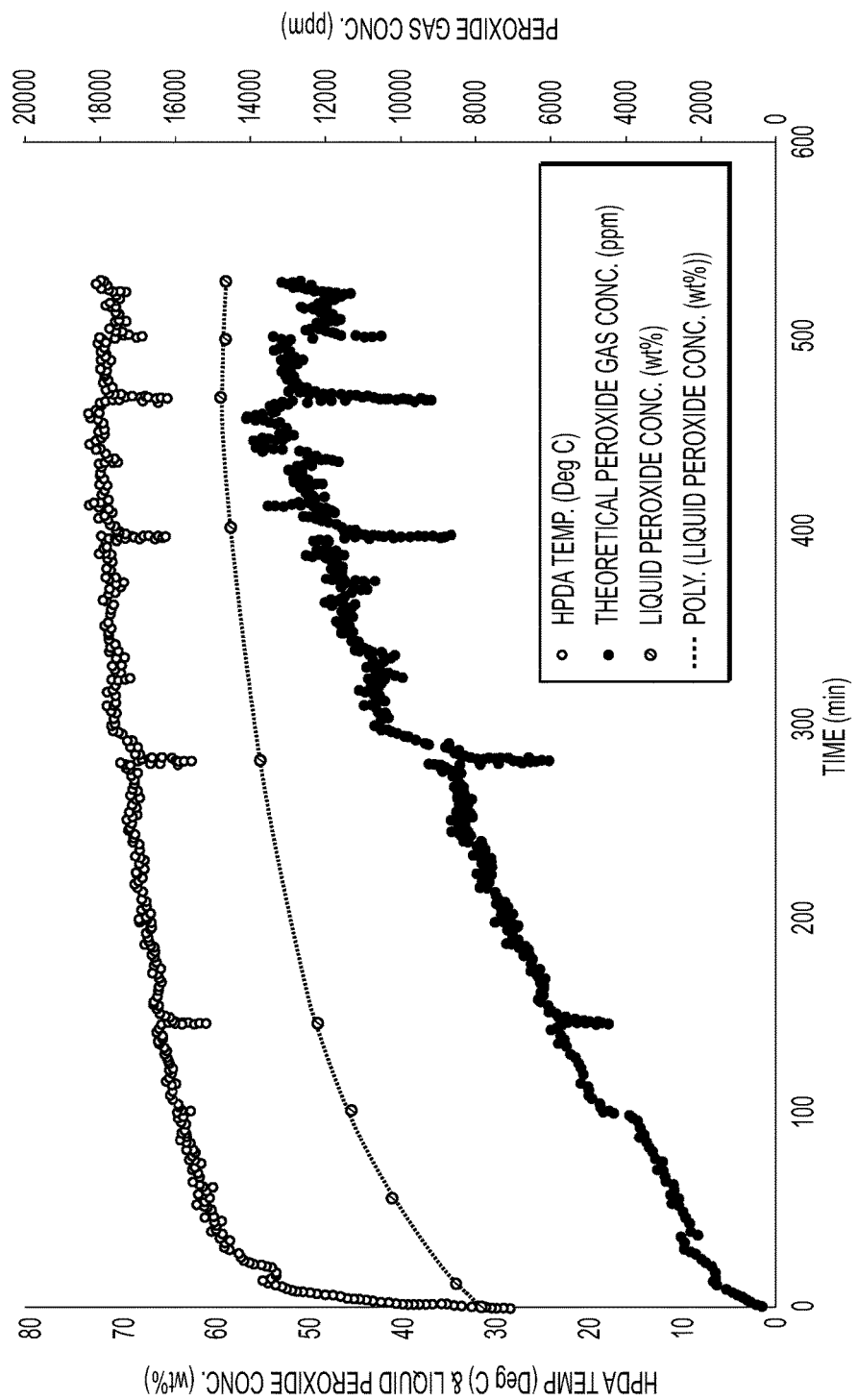
FIG. 20 is a graph displaying the peroxide gas output concentration profile vs time.

The following stabilized concentration test was run using a 31.4% peroxide liquid source and running a variable nitrogen carrier gas flow rate through an HPDA. The HPDA bath concentration was concentrated from 31.4 to 59.2% over a 480 minute period and then the 59% peroxide was stabilized over a 60 minute period at 4.5 SLM nitrogen flow. Replenishment was with the same initial concentration peroxide solution. FIG. 18 displays temperature profiles and HPDA liquid concentration over the test duration. Downstream pressures were modulated to achieve the nitrogen flow rate in FIG. 19. FIG. 20 displays the peroxide gas output concentration profile vs time. Liquid peroxide sampling cause troughs in the HPDA temperature. The troughs in the HPDA temperature cause downward spikes in the peroxide gas output. If the system were to run without sampling these downward peaks would not be present.

Example 7

Stabilized Peroxide Delivery Using Dry Nitrogen Carrier Gas

A stabilized concentration experiment was run using a 35.0 wt % peroxide liquid source and a fixed 5 slm dry nitrogen carrier gas flow rate through a multi-lumen fluorinated ion-exchange polymer prepared as an ammonium salt as part of an HPDA using the configuration of FIG. 21. Prior to measuring the hydrogen peroxide gas, the HPDA bath concentration was increased from 35 wt % to 64.6 wt % over a 6 hour duration by passing dry nitrogen gas into the HPDA which was held at 77.5±1° C. and a pressure of 785±1 torr for the entire experiment. In each of examples 7-10, a refill bath solution was used to maintain a constant volume using the same initial concentration of $H_2O_2$.

Figure 23:
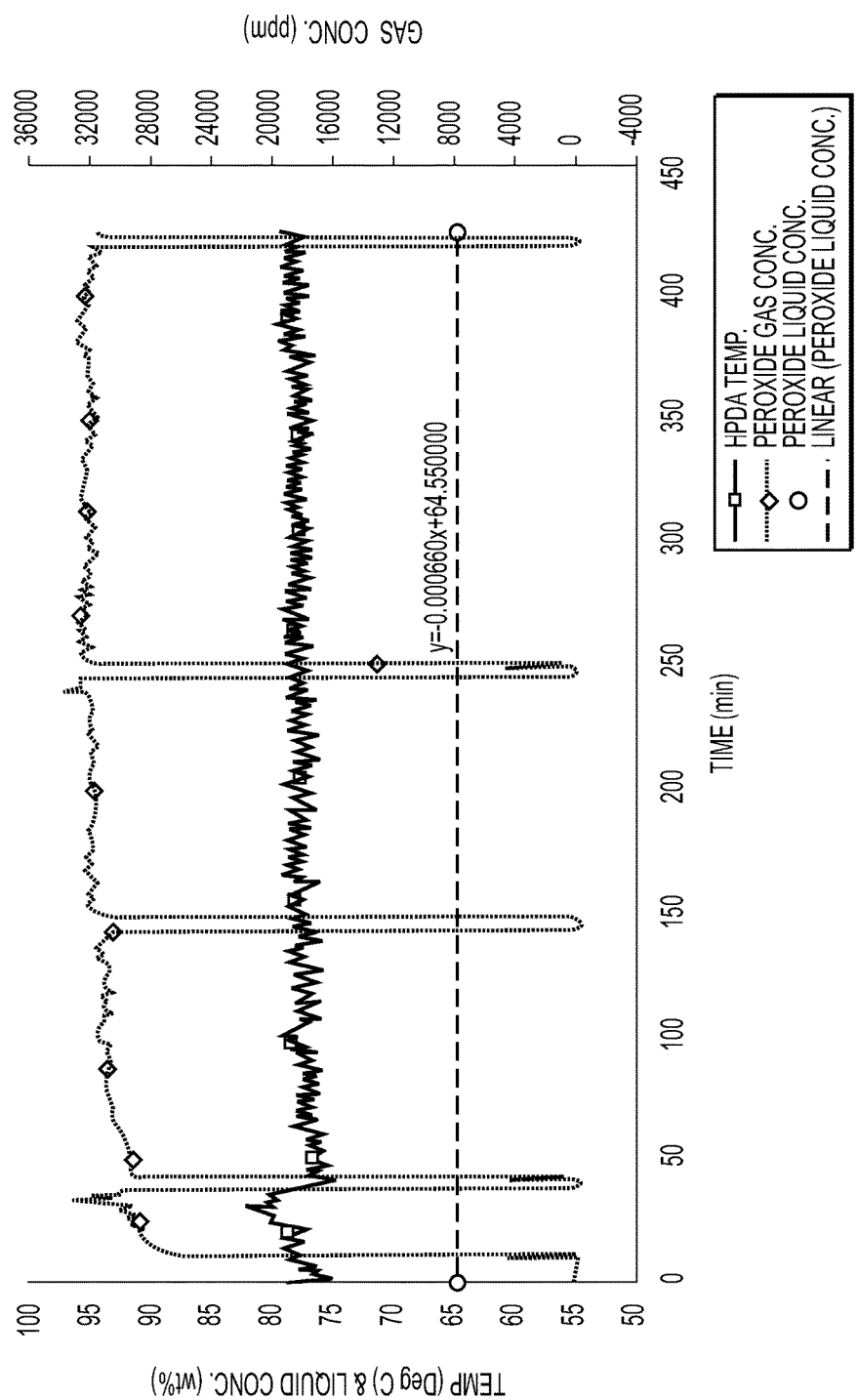
FIG. 23 is graph displaying the peroxide gas output concentration profile vs time.

After this 6 hour concentration period, the concentration of hydrogen peroxide gas was measured periodically (the downward spikes are artifacts due to the measurement device). FIG. 23 shows the stability of the 64.6 wt % solution in the HPDA and the stable delivery of high concentration peroxide gas over a 420 minute period after the 6 hour concentration period. The liquid concentration of hydrogen peroxide in the HPDA decreased by 0.4 wt % over the 420 minute interval. The peroxide gas delivered had an averaged concentration of 32214 ppm with a standard deviation of 235.2 ppm.

Example 8

Stabilized Peroxide Delivery Using Dry Nitrogen Carrier Gas

Figure 24:
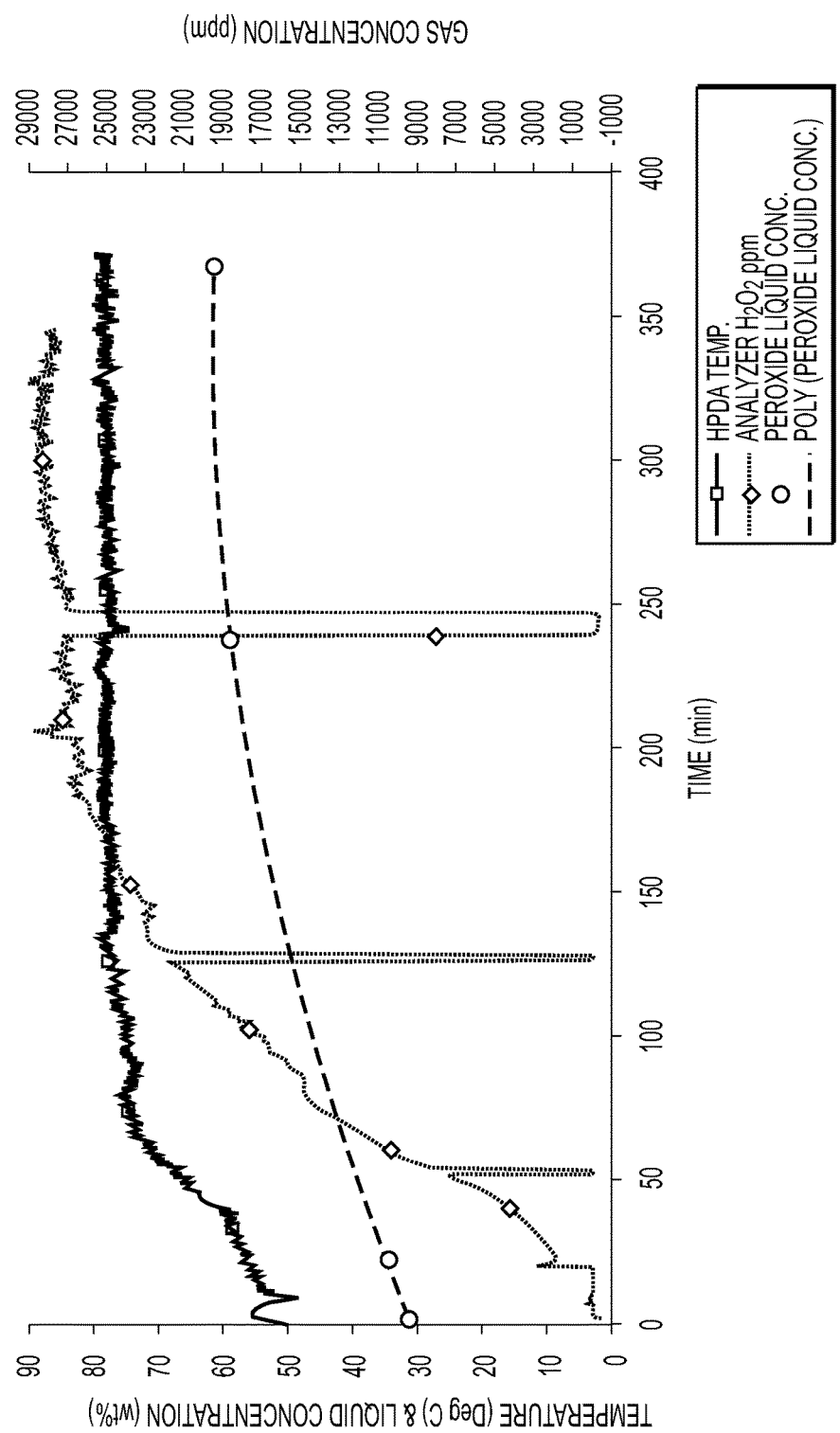
FIG. 24 is a graph displaying the peroxide gas output concentration profile vs time.

A stabilized concentration experiment was run using a 31.3 wt % peroxide liquid source and a fixed 5 slm dry nitrogen carrier gas flow rate through a multi-lumen fluorinated ion-exchange polymer prepared as an ammonium salt as part of an HPDA using the configuration of FIG. 21. Prior to measuring the hydrogen peroxide gas, the HPDA bath concentration was increased from 31.3 wt % to 61.2 wt % over a 300 minute duration and then held constant at 61.2 wt % for the last 70 minutes of the experiment by passing dry nitrogen gas into the HPDA which was held at 77.8±1° C. and a pressure of 785±1 torr for the entire experiment. FIG. 24 displays the results where the concentration reaches an asymptotic value of 61.2 wt % while delivering a peroxide gas concentration of 28197 ppm with a standard deviation of 262 ppm.

Example 9

Stabilized Peroxide Delivery Using Dry Nitrogen Carrier Gas

Figure 25:
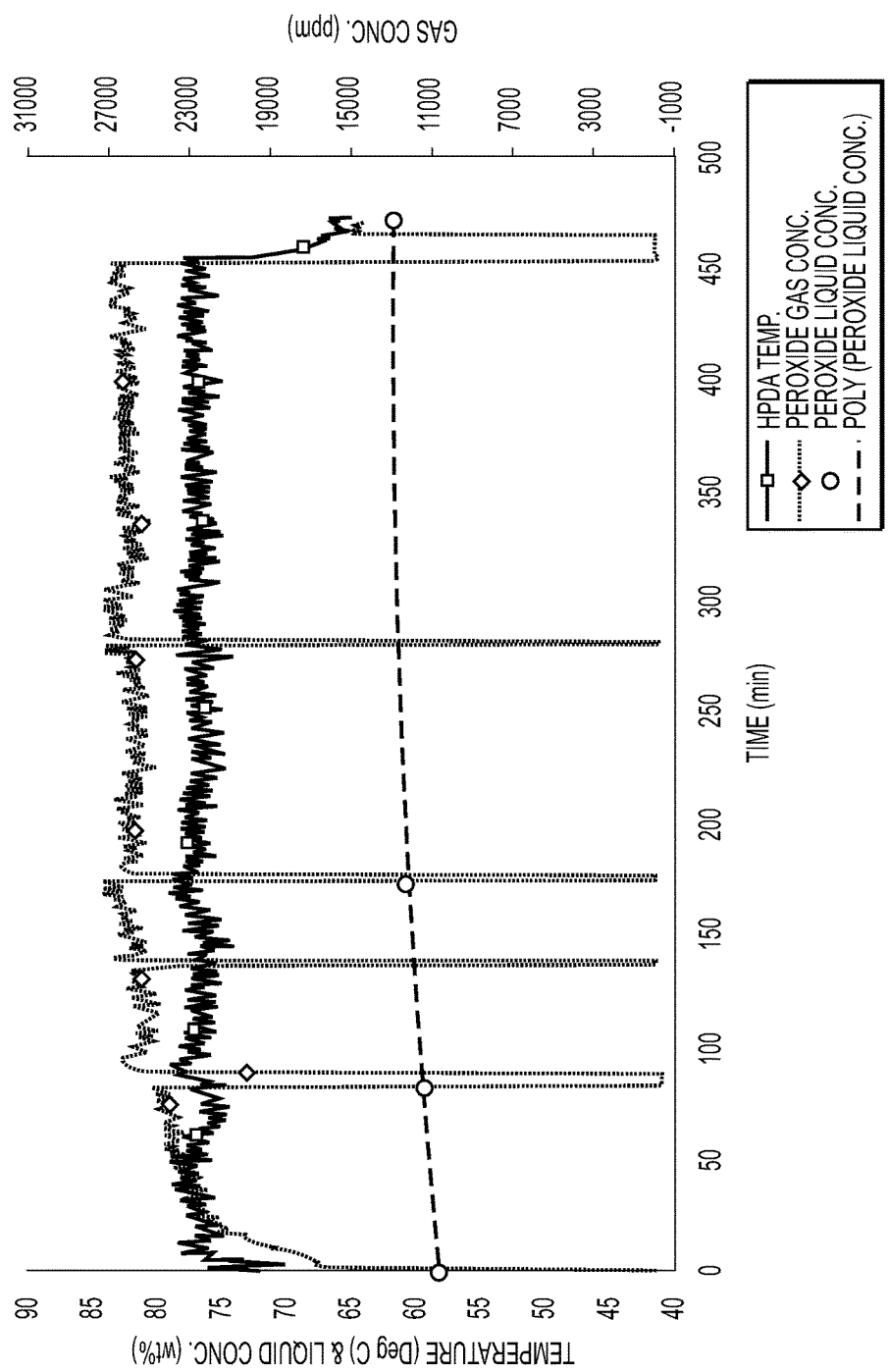
FIG. 25 is a graph displaying the peroxide gas output concentration profile vs time.

A stabilized concentration experiment was run using a 31.3 wt % peroxide liquid source and a fixed 5 slm dry nitrogen carrier gas flow rate through a multi-lumen fluorinated ion-exchange polymer prepared as an ammonium salt as part of an HPDA using the configuration of FIG. 21. The HPDA was manually filled with a starting concentration of 58.2 wt %. Prior to measuring the hydrogen peroxide gas, the HPDA bath concentration was increased to 61.8 wt % over a 300 minute duration with dry nitrogen gas and then held constant at 61.8 wt % for the last 150 minutes of the experiment. The HPDA solution was held at 77.5±1° C. and a gas pressure of 785±1 torr for the experiment. FIG. 25 displays the results where the concentration reaches an asymptotic value of 61.7 wt % while delivering a peroxide gas concentration of 26108 ppm with a standard deviation of 344 ppm.

Example 10

Stabilized Peroxide Delivery Using Dry Nitrogen Carrier Gas

Figure 26:
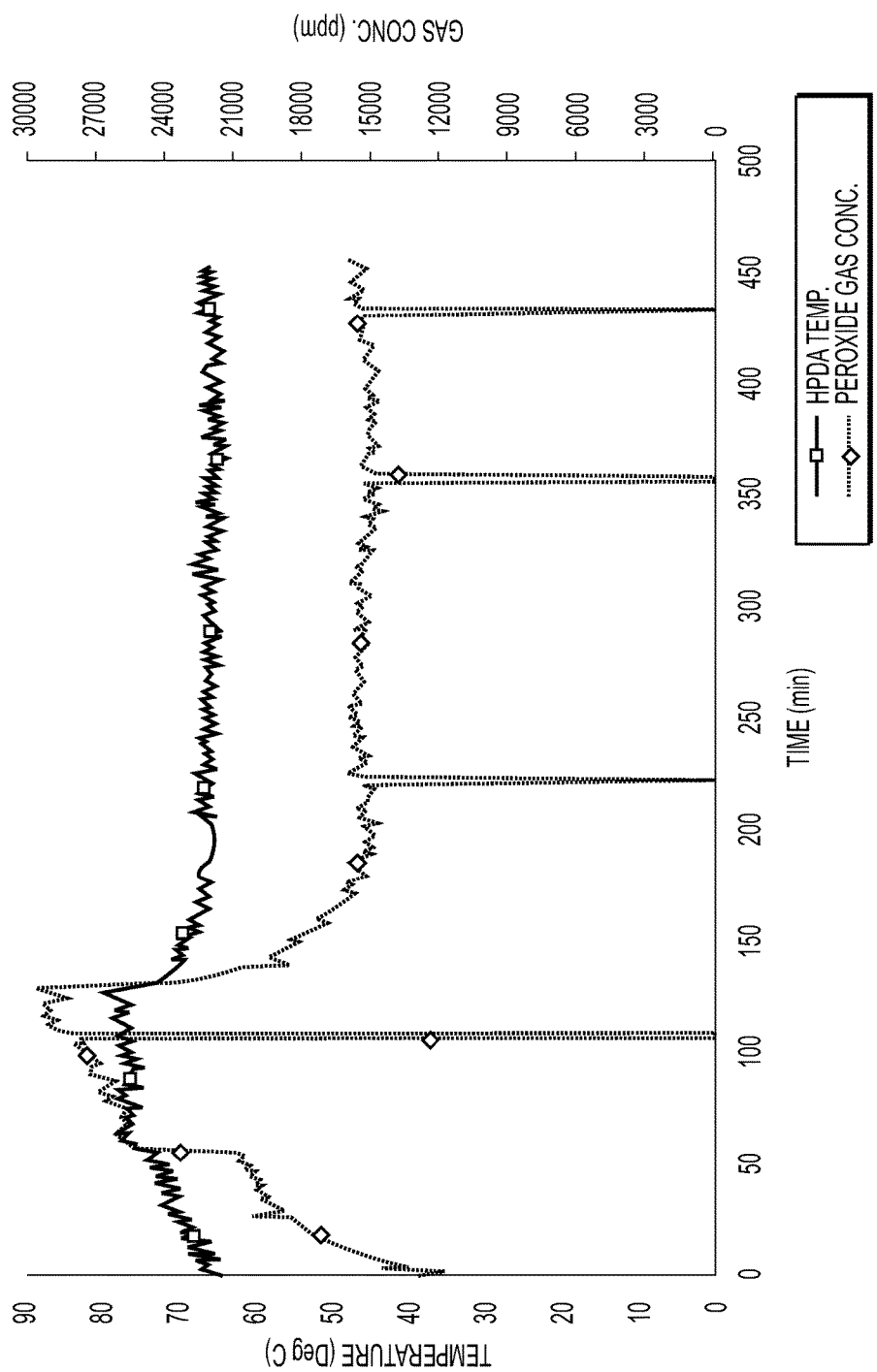
FIG. 26 is a graph displaying the peroxide gas output concentration profile vs time.

A stabilized concentration experiment was run using a 31.3 wt % peroxide liquid source and a fixed 5 slm dry nitrogen carrier gas flow rate through a multi-lumen fluorinated ion-exchange polymer prepared as an ammonium salt as part of an HPDA using the configuration of FIG. 21. This experiment started with an HPDA liquid peroxide concentration of 61.2 wt %. The solution was brought up to 77.5° C. during the first hundred minutes to verify that the peroxide gas output was approximately 26000 ppm and was in agreement with the results from example 9, which it did. At 130 minutes, the HPDA solution temperature was lowered and held at 66.0±1° C. to stabilize a lower peroxide output. FIG. 26 displays the test results. The final liquid concentration reached an equilibrium of 65.1 wt % while delivering a stabilized peroxide gas concentration of 15267 ppm with a standard deviation of 279 ppm.

Decontamination Examples

The Examples presented below illustrate procedures and results supporting the conclusion that gas phase hydrogen peroxide, produced using the above-described apparatus, effectively killed microorganisms and rendered DNA non-amplifiable in DNA polymerase-based in vitro nucleic acid amplification reactions. Results obtained during development of the invention indicated that treatment of bacterial samples with gas phase aqueous hydrogen peroxide did not significantly reduce the number of viable organisms where a visible mist or fog was visible indicating the presence of droplets in the hydrogen peroxide which condensed onto the sample. By comparison, when samples were treated with gas-phase hydrogen peroxide, efficient decontamination was observed as indicated below.

Example 11

Experimental Set Up

Figure 27:
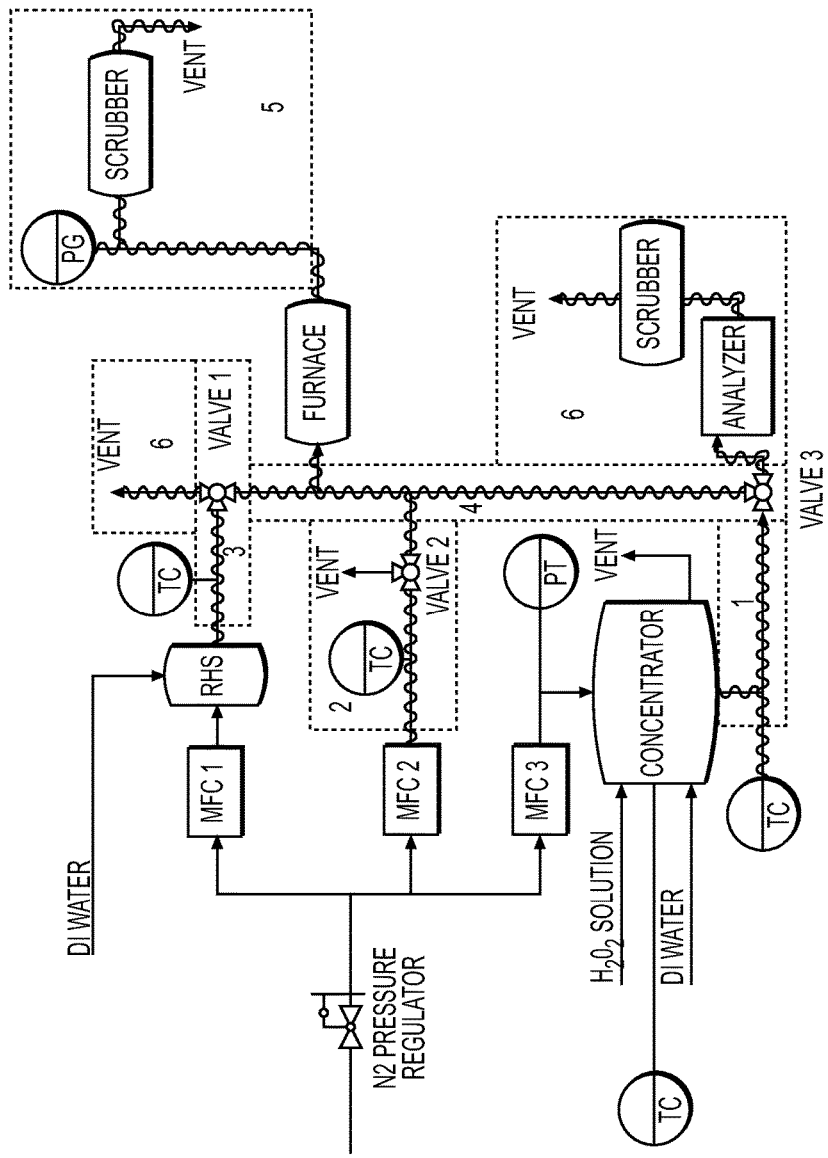
FIG. 27 is a setup graphic illustrating arrangement of various components of the apparatus used for carrying out the decontamination testing.

FIG. 27 schematic illustrates the apparatus used in this experiment. Equipment included: a purified clean dry air (CDA) gas supply; a pressurized deionized (DI) water supply; a pressure regulator with gauge, a Filterite MPTE-010-1/4CS 0.01 micron gas filter; 3 mass flow controllers (MFCs); an MFC control box; a Stable Gas Delivery (SGD) System ("Concentrator" in FIG. 27) and a relative humidity system (RHS) (RASIRC, San Diego, Calif.). Membranes using a fluorinated ion-exchange polymer prepared as an ammonium salt were utilized. Also shown are 3 three-way valves; 6 Teflon coated J-type thermocouples (TC); a quartz furnace; a DirectLogic PLC; a pressure gauge (PG); 2 hydrogen peroxide scrubbers; and heat tracing for test manifold (EZ Zone Watlow Controllers, TCs, Heater Tape, and Insulation).

Figure 28:
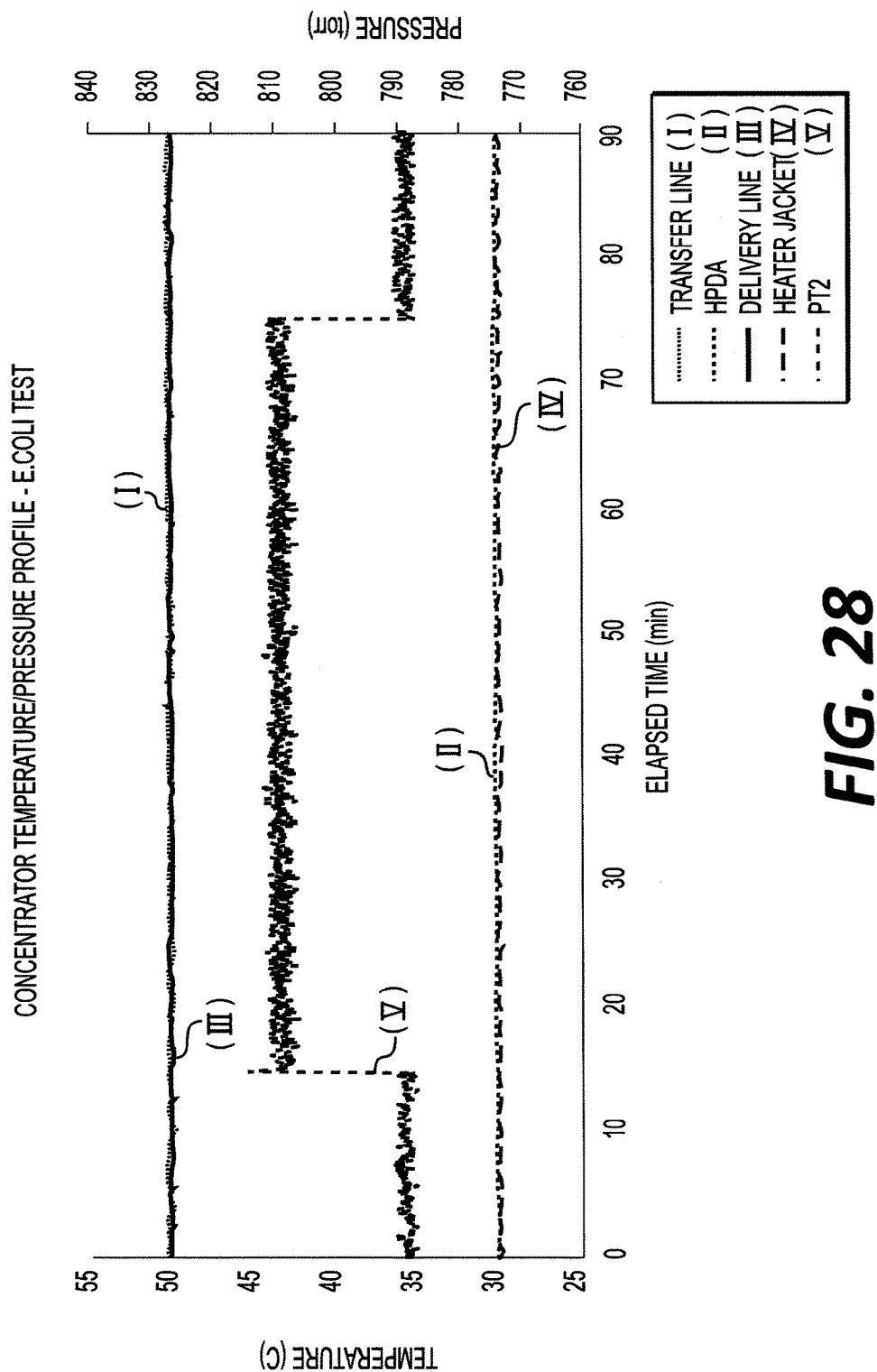
FIG. 28 is a graph showing the Concentrator temperature/pressure profile during decontamination testing of *E. coli*.
Figure 29:
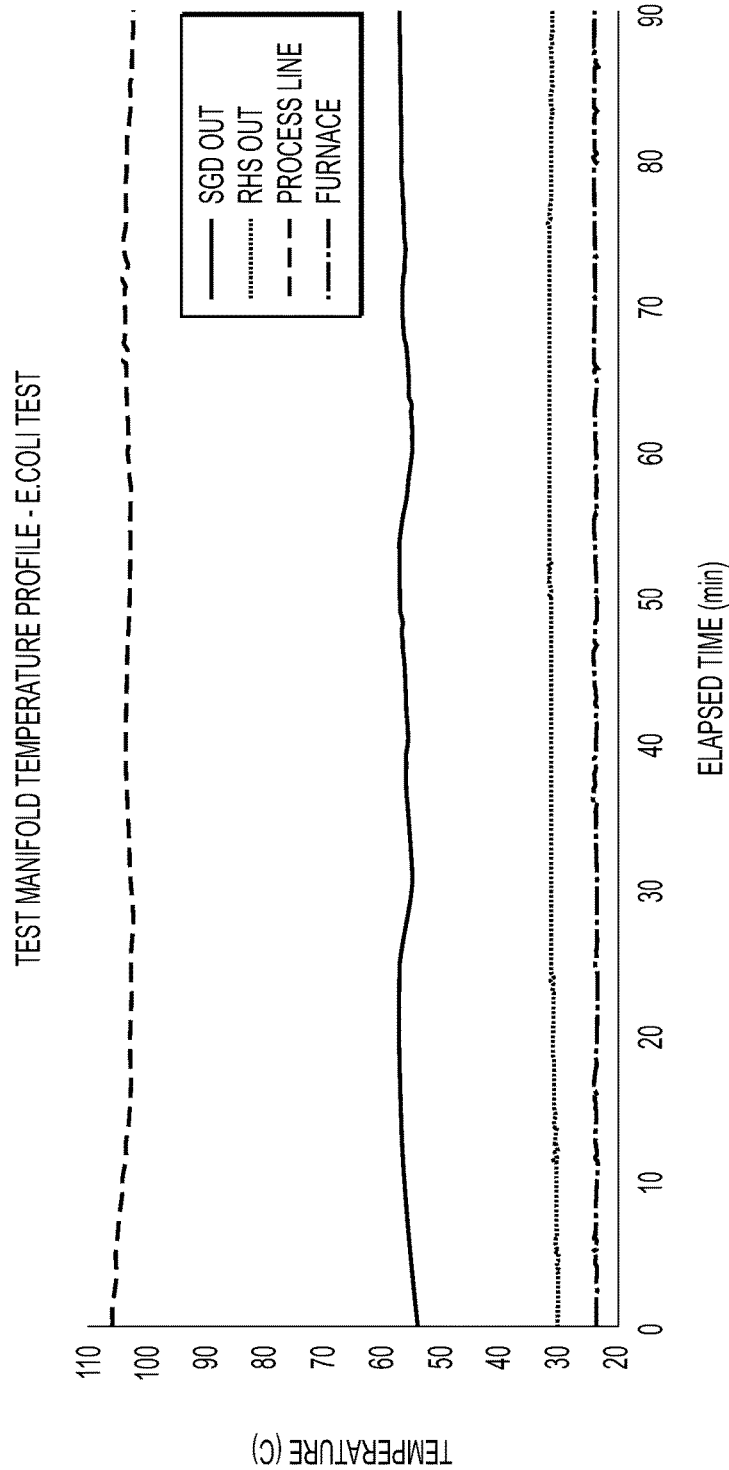
FIG. 29 is a graph showing the test manifold temperature profile during decontamination testing of *E. coli*.
Figure 30:
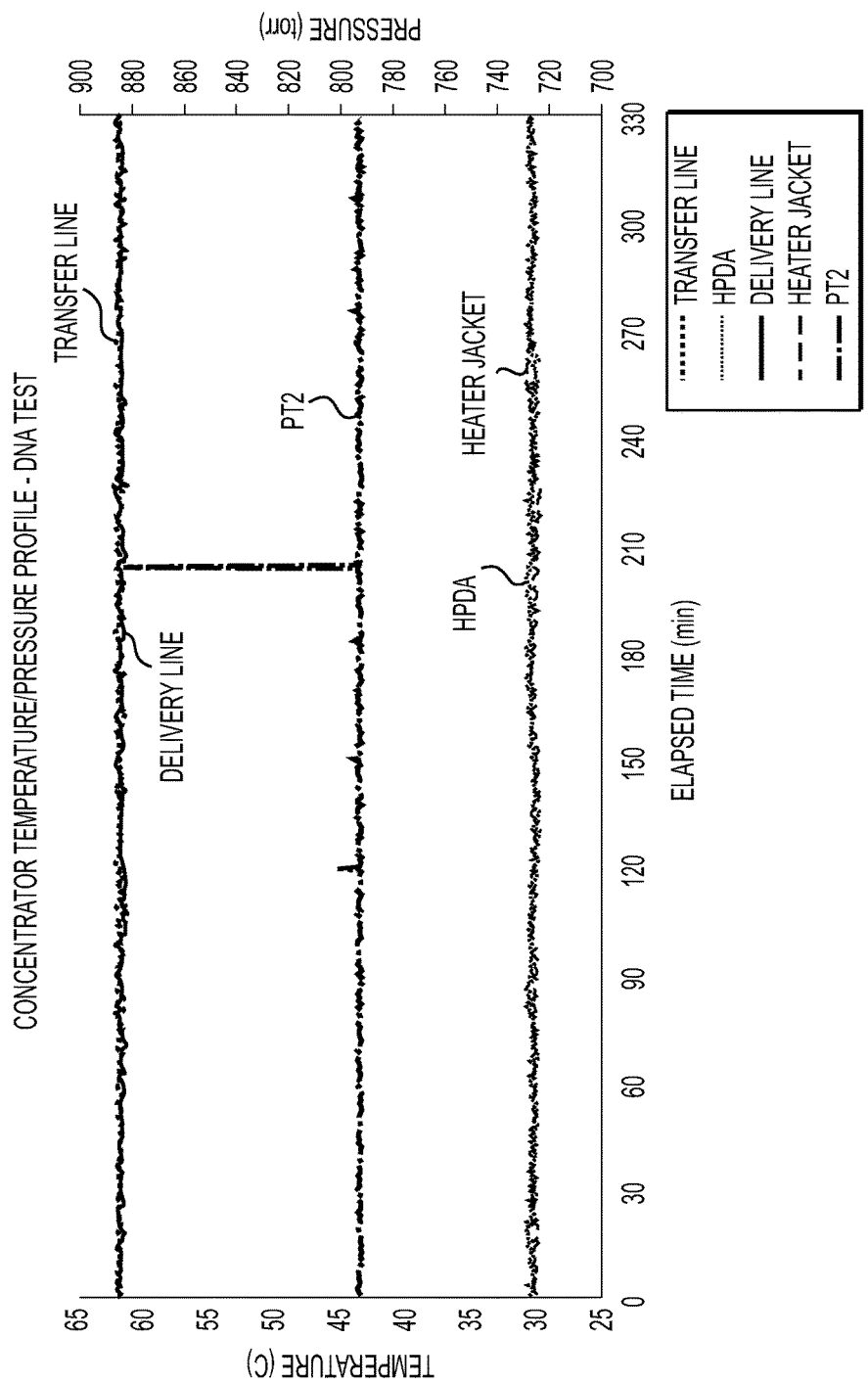
FIG. 30 is a graph showing the Concentrator temperature/pressure profile during decontamination testing of DNA.
Figure 31:
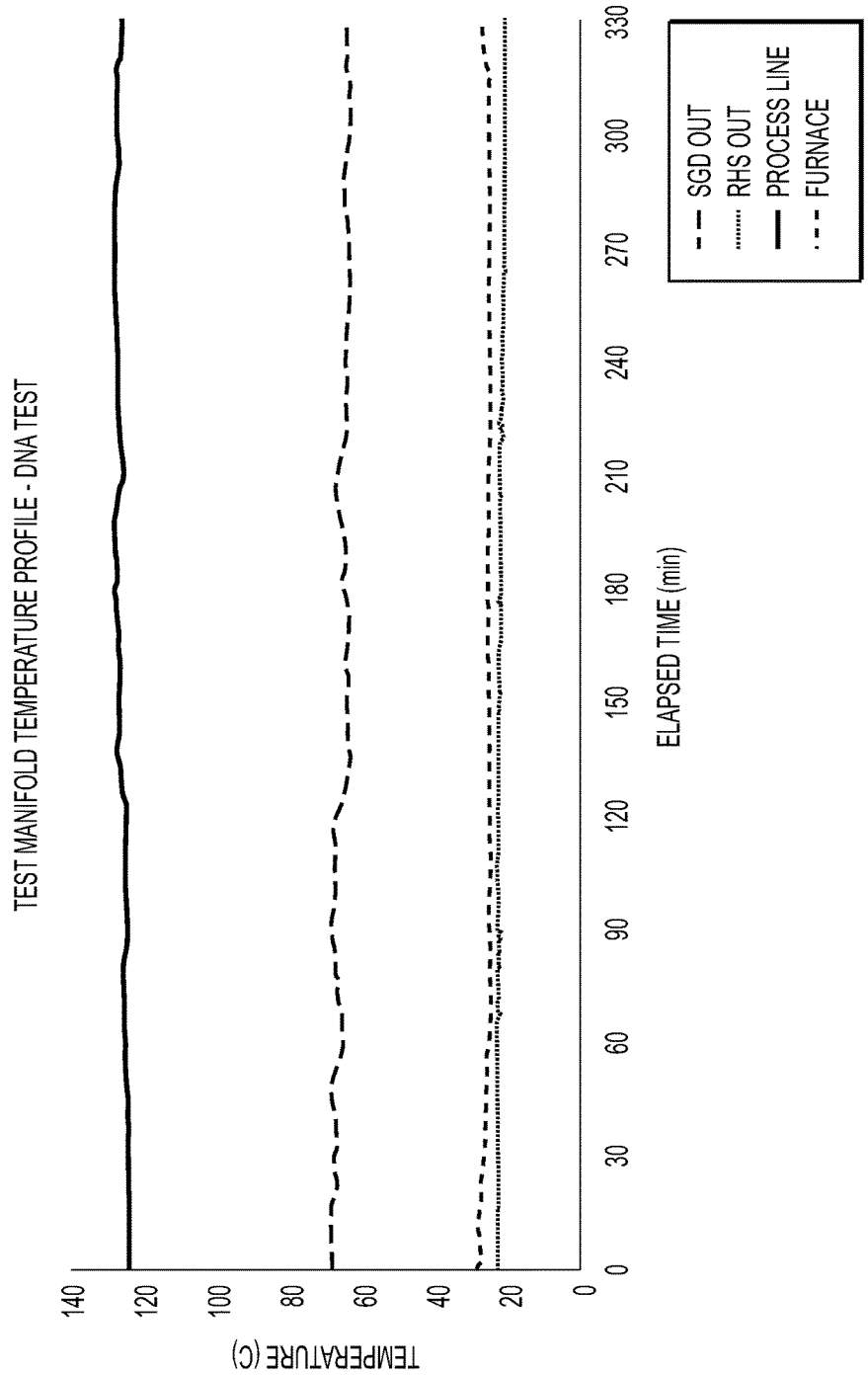
FIG. 31 is a graph showing the test manifold temperature profile during decontamination testing of DNA.

Operation of the decontamination apparatus can be understood with reference to FIG. 27. The CDA gas pressure was maintained at 25 psig with the pressure regulator. A 0.01 micron filter removed particulates from the gas stream. The MFCs controlled the flow of the carrier gas streams and the dilution gas stream. The RHS was used to add water to the gas stream. The SGD was used to add hydrogen peroxide and water to the gas stream. The water temperature was used to control the output of the humidifier. The valves (V-1, V-2, and V-3) were used to send either the dry CDA gas stream, the RHS gas stream, and/or SGD gas stream through the furnace or out to vent. TC-1 may be used to measure the temperature of the dry CDA gas stream. TC-2 may be used to measure gas temperature downstream of the RHS. TC-3 and TC-4 were used to measure the gas temperature downstream of the SGD. The furnace was used to keep the bacterial samples at temperature to prevent condensation. TC-5 was used to measure the temperature in the quartz furnace. TC-6 was used to measure the gas temperature downstream of the furnace. A pressure gauge (PG-1) was used to monitor the pressure in the furnace. A Teledyne Prototype Analyzer was used to determine stability of the peroxide gas and its temperature was kept at 120° C. A scale was used to determine the consumption rate of liquid by weight and to calculate the concentration of the peroxide and water in the gas stream. Two scrubbers were used to decompose the hydrogen peroxide. The boxed sections show the individual heat traced control zones for this experiment. The control zones are as follows:

Zone 1=SGD Outlet
Zone 2=CDA Dilution Gas
Zone 3=RHS Outlet
Zone 4=Quartz Furnace Inlet
Zone 5=Quartz Furnace Outlet
Zone 6=SGD/RHS/Analyzer Vent FIG. 28 and FIG. 29 present records of operational parameters measured during *E. coli* decontamination testing. FIG. 30 and FIG. 31 present operational parameters measured during DNA decontamination testing. Example 12 describes measurements used for performing the decontamination testing. For both trials, initial concentrations of hydrogen peroxide in the aqueous hydrogen peroxide sources were 31%. Contacting the gas phases of the respective aqueous hydrogen peroxide sources with a carrier gas under continuous flow conditions increased the concentrations of hydrogen peroxide to higher second levels of 65.8% for the DNA decontamination procedure, and 59.3% for the *E. coli* decontamination procedure. In both procedures, the third concentration of hydrogen peroxide in the aqueous hydrogen peroxide solution that was added to the aqueous hydrogen peroxide source was 31%. The addition took place while the carrier gas was contacting the gas phase of the aqueous hydrogen peroxide source in the continuous flow. As this procedure was taking place, and after addition of the aqueous hydrogen peroxide solution to the aqueous hydrogen peroxide source had begun (e.g., to maintain a constant volume in the aqueous hydrogen peroxide source), a gas stream was withdrawn and employed in the decontamination procedures. As indicated in Table 4, the withdrawn gas streams used for *E. coli* and DNA decontamination testing exhibited stable steady-state concentrations of hydrogen peroxide that varied by less than ±10%.

Example 12

Sample Preparation for Decontamination

Samples tested in this procedure were *E. coli* and purified bovine genomic DNA. Table 2 presents the composition and flow rates of the two gas streams used in the experiment. "DP" represents the dew point. Gas flow is measured in standard liters per minute.

Results from monitoring the hydrogen peroxide output of the Concentrator during decontamination testing of *E. coli* and purified DNA are presented in Table 3. Notably, hydrogen peroxide output remained very stable throughout the testing periods.

TABLE 3

Concentrator Output Logs for Test Runs

| *E. coli* Testing | | DNA Testing | |
| --- | --- | --- | --- |
| Run Time (min) | Output† (ppm) | Run Time (min) | Output† (ppm) |
| 1 | 3886.10 | 0 | 2993.54 |
| 10 | 3883.31 | 20 | 2614.29 |
| 24 | 3838.03 | 40 | 2475.12 |
| 30 | 3829.81 | 60 | 2518.74 |
| 40 | 3818.4 | 80 | 2407.37 |
| 50 | 3776.75 | 100 | 2518.74 |
| 60 | 3782.45 | 120 | 2551.01 |
| 70 | 3743.70 | 140 | 2639.92 |
| 80 | 3735.56 | 160 | 2889.44 |
| 90 | 3737.1 | 180 | 2950.06 |
| | | 200 | 2953.38 |
| | | 220 | 2859.30 |
| | | 240 | 2912.85 |
| | | 260 | 2917.39 |
| | | 280 | 3006.13 |
| | | 300 | 3006.48 |
| | | 320 | 3084.65 |

†Hydrogen peroxide output before dilution

Results from the output logs presented above are summarized in Table 4.

TABLE 4

Averaged Hydrogen Peroxide Output Measured During Test Runs

| Test Run | Concentrator $H_2O_2$ Output (ppm) | $H_2O_2$ After Dilution (ppm) |
| --- | --- | --- |
| *E. coli* | 3800 ± 54 | 772 ± 11 |
| DNA | 2780 ± 220 | 563 ± 44 |

Example 13 summarized operation of the apparatus that provided hydrogen peroxide gas for the decontamination procedures described subsequently.

Example 13

Operating Parameters for Decontamination Testing

The SGD was filled with a 31% w/w hydrogen peroxide solution. The initial test manifold was set to the following temperatures:

TABLE 2

General Gas Parameters

| | $H_2O_2$ ppm Before Dilution | $H_2O$ ppm Before Dilution | Carrier Gas Flow (slm) | Dilution Gas Flow (slm) | Total Flow (slm) | $H_2O_2$ ppm After Dilution | $H_2O$ ppm After Dilution |
| --- | --- | --- | --- | --- | --- | --- | --- |
| Humidified CDA (RHS) | 0 | 55563 DP = 35° C. | 0.18 | 4.81 | 5 (10 sscm of $H_2O$ gas) | 0 | 2118 |
| $H_2O_2$ Gas (SGDC) | 2500 | 10500 | 1 | 4 | 5 | 505 | 2122 |

Zone 1=72° C. (Outlet temperature of SGD)
Zone 3=90° C. (Due to high RHS outlet temperature setting. Gas temperature is above 80° C. without heat tracing).
Zone 2, 4, 5, 6, and oven=25° C.
Zone 7=≥60° C.

The dilution gas flow rate was set to 5 slm, the RHS carrier gas to 180 sccm, and the SGD carrier gas flow to 1 slm. The RHS was then set to a 35° C. dew point, and the SGD to 30° C., running both gas streams to vent. The furnace and the heat-traced line temperatures were adjusted to achieve the desired gas temperatures. The SGD and RHS systems were allowed to stabilize. Samples were treated and processed as described in the following Examples.

Example 14 describes procedures that confirmed microorganism viability was dramatically reduced following exposure to gas phase hydrogen peroxide under mild conditions. More particularly, the procedure employed E. coli (a gram-negative bacterium) as the model microorganism. While the following demonstration was carried out using challenge bacteria under laboratory conditions, it is to be understood application of the gas phase hydrogen peroxide has many practical applications falling within the scope of the present invention. Some non-limiting examples include decontamination of: food crops or other agricultural materials; industrial and residential surfaces, including all or part of rooms in healthcare facilities; medical devices; medical waste; and the like.

Example 14

Bacterial Inactivation by Gas-Phase Hydrogen Peroxide

Sterile glass microscope slides were spotted with 20 μl samples of either a control phosphate buffer, or a liquid stock of E. coli ($8.4 \times 10^8$ cfu/ml). It is to be understood that one colony-forming unit ("cfu") corresponds to one viable bacterial cell. Accordingly, each spotted sample of bacteria initially contained $1.7 \times 10^7$ cfu of the microorganism. Two slides harboring phosphate buffer controls, and two slides harboring the bacterial samples were covered and maintained at room temperature as untreated controls. Two slides harboring phosphate buffer controls, and two slides harboring the bacterial samples were inserted into a vented, temperature-controlled chamber maintained at 25° C. during the subsequent exposure to hydrogen peroxide gas. The chamber was initially purged for 15 minutes with clean dry air (i.e., "CDA") humidified to 2118 ppm $H_2O$. The samples to be treated were then exposed to gas-phase $H_2O_2$ at 505 ppm and $H_2O$ at 2122 ppm for 60 minutes. Finally, the chamber was purged for an additional 15 minutes with humidified CDA. Following the exposures, sample spots were independently taken up in phosphate buffer, subjected to serial dilution in the same phosphate buffer, and aliquots of the dilutions titered for growth on tryptic soy agar (i.e., "TSA") plates. Results from the different treatment conditions are presented in Table 5.

TABLE 5

Quantitative Evidence for Sterilization of Bacterial Samples

| Trial | $H_2O_2$ treatment | Untreated |
|---|---|---|
| Control slide 1 | | No Growth |
| Control slide 2 | No Growth | |
| Control slide 3 | No Growth | |
| Bacterial slide 1 | | $9.7 \times 10^6$ colonies |

TABLE 5-continued

Quantitative Evidence for Sterilization of Bacterial Samples

| Trial | $H_2O_2$ treatment | Untreated |
|---|---|---|
| Bacterial slide 2 | No Growth | |
| Bacterial slide 3 | No Growth | |

Results indicated that bacterial samples treated with gas-phase hydrogen peroxide generated by the apparatus and techniques described herein were effectively sterilized. None of the control slides showed evidence for viable bacteria, as expected. Thus, any bacteria detected in the experiment must have originated from the E. coli stock. Recovery of viable bacteria from untreated Bacterial slide 1 provided the baseline for comparison with treated samples. As well, this untreated sample provided empirical evidence for recovery of about 56% of the starting quantity of E. coli following all processing steps in the absence of hydrogen peroxide exposure. The remaining samples treated with hydrogen peroxide gas showed no evidence for viable organisms. Thus, the exposure to hydrogen peroxide gas was responsible for reducing the number of viable bacteria to an undetectable level. This finding was consistent with an at least 7 log reduction in the number of viable bacteria. At the very least, results supported a 6-7 log reduction in the number of viable bacteria. This demonstrated effective killing of the challenge microorganism.

Example 15 describes use of the invented hydrogen peroxide delivery apparatus in a method of rendering nucleic acid non-amplifiable in an in vitro nucleic acid amplification reaction. The procedure employed treatment of DNA samples with hydrogen peroxide gas, followed by use of the treated samples as templates in standard PCR reactions. Bovine genomic DNA served as a model DNA responsible for carryover contamination of an instrument used for conducting nucleic acid amplification. The procedure was made quantitative by comparison of treated results with a standard curve.

Example 15

Chemical Inactivation of DNA Using Gas-Phase Hydrogen Peroxide

A PCR plate to be used for quantifying amplifiable DNA was prepared with three replicates at each target input level (i.e., ranging from 0 ng to 1,000 ng). In each instance, measured aliquots of an aqueous solution of bovine genomic DNA were added to individual wells of the plate, and then dried. Plates harboring DNA samples were exposed to gas phase hydrogen peroxide treatment in a temperature-controlled chamber maintained at 25° C. The chamber was initially purged for 15 minutes with CDA. Trials receiving hydrogen peroxide treatment were then exposed to gas-phase $H_2O_2$ at 505 ppm and $H_2O$ at 2122 ppm for 5 hours. Finally, the chamber was purged for an additional 15 minutes with CDA. Each well containing treated sample next received an aliquot of liquid reagents needed to carry out PCR amplification reactions. These reagents included: a pair of unlabeled DNA primers capable of amplifying the template; nucleotide triphosphates; buffer and salts; a dual-labeled hydrolysis probe specific for the DNA amplification product; and a thermostable DNA polymerase having 5'-3' exonuclease activity. Amplification reactions were carried out using procedures familiar to those of ordinary skill in the art, and the appearance of fluorescent signals monitored as a function of time in a real-time format. Calculated Ct values and corresponding amounts of DNA remaining after hydrogen peroxide exposure were determined using a threshold value that was manually set to include samples yielding the highest Ct values (close to 40 cycles). These high Ct samples represented very low concentrations of DNA (i.e., at the limits of sensitivity), and so displayed larger coefficients of variation in the results. Separately, standard reactions prepared using known quantities of template DNA that had not been subjected to hydrogen peroxide exposure were used to prepare a calibration plot for quantifying intact starting amounts of template DNA in samples that had undergone treatment. Tabulated results are shown below.

TABLE 6

Quantifying DNA Inactivation Mediated by Hydrogen Peroxide Gas

| Replicate | Input ng DNA | Calculated ng After Treatment | Remaining % | Decrease % | Average Decrease % |
|---|---|---|---|---|---|
| 1 | 0 | 0 | — | — | |
| 1 | 0 | 0 | — | — | |
| 1 | 0 | 0 | — | — | |
| 2 | 1 | 0 | 0 | 100 | 100.00 |
| 2 | 1 | 0 | 0 | 100 | |
| 2 | 1 | 0 | 0 | 100 | |
| 3 | 10 | 0.145 | 1.45 | 98.55 | 97.44 |
| 3 | 10 | 0.072 | 0.72 | 99.28 | |
| 3 | 10 | 0.55 | 5.5 | 94.5 | |
| 4 | 100 | 0.81 | 0.81 | 99.19 | 99.70 |
| 4 | 100 | 0.08 | 0.08 | 99.92 | |
| 4 | 100 | 0.022 | 0.022 | 99.978 | |
| 5 | 1000 | 0.043 | 0.0043 | 99.9957 | 99.99 |
| 5 | 1000 | 0.047 | 0.0047 | 99.9953 | |
| 5 | 1000 | 0.33 | 0.033 | 99.967 | |

The results presented in Table 6 demonstrated that gas-phase hydrogen peroxide efficiently compromised the ability of treated DNA to serve as a template in a nucleic acid amplification reaction. In each case, the treatment substantially reduced the average amount of DNA that could be amplified. Amplifiable DNA in the sample containing the lowest amount of starting material was completely undetectable. Amplifiable DNA in the sample containing the greatest amount of starting material was reduced by about 4 logs. This indicated that DNA was rendered non-amplifiable using standard DNA polymerase-based nucleic acid amplification techniques.

Example 16

Experimental Set Up for Additional Embodiments for Decontamination

Figure 4:
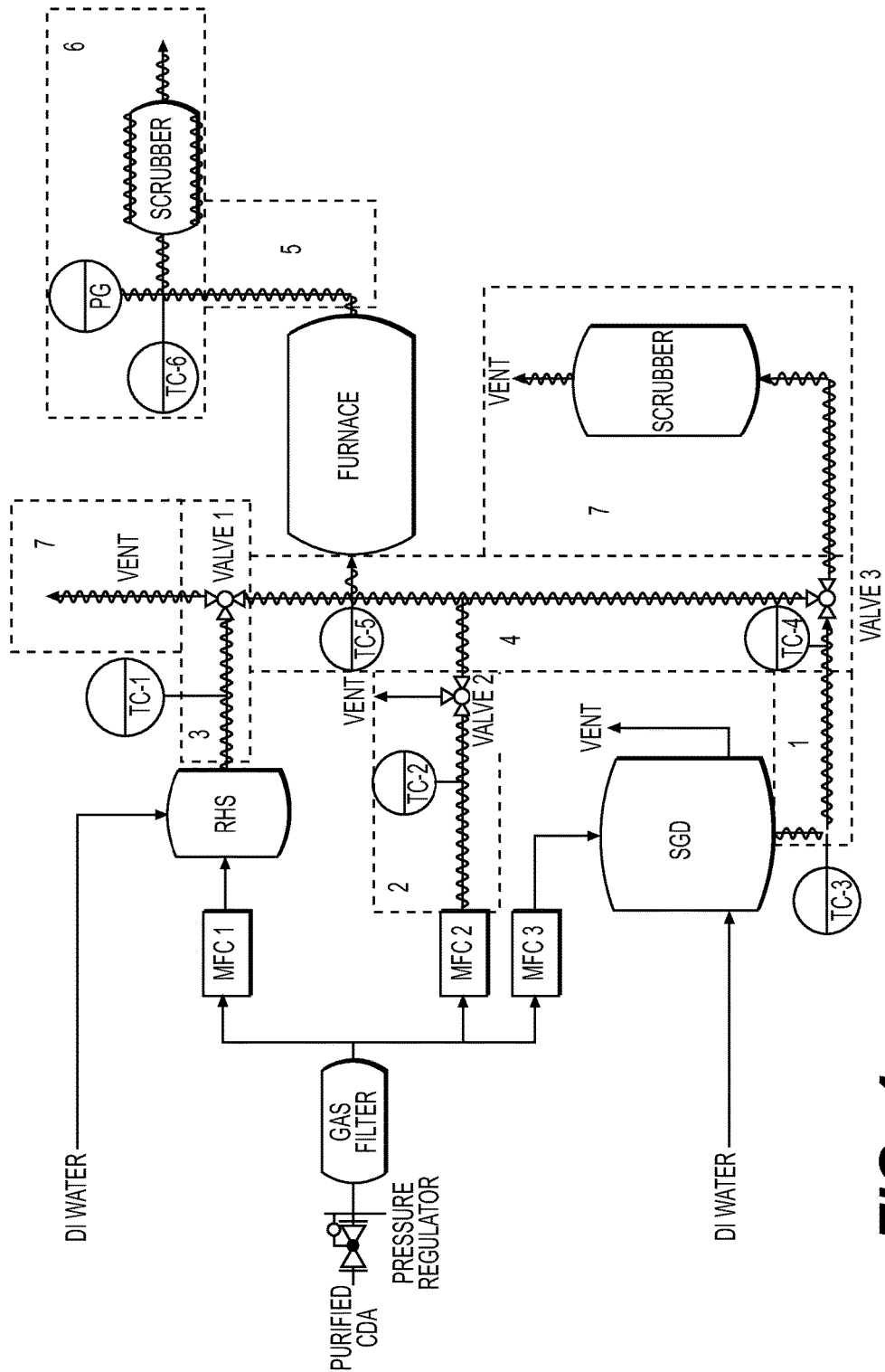
FIG. 4 is a P&ID diagram according to certain embodiments of the invention showing a setup for decontamination and control tests.

FIG. 4 was the schematic for Examples 16, 17, 18 and 19. Equipment used in FIG. 4 include purified CDA Gas Supply, Pressurized DI Water Supply, Pressure Regulator with Gauge, Filterite MPTE-010-1/4CS 0.01 Micron Gas Filter, 3 MFCs, MFC Control Box, Rasirc's SGD System. Membranes using a fluorinated ion-exchange polymer prepared as an ammonium salt were utilized. Rasirc's RHS. 3 Three-way Valves, 6 Teflon Coated J-type Thermocouple (TC), a Quartz Furnace, a DirectLogic PLC, a Pressure Gauge, 2 Hydrogen Peroxide Scrubbers, and Heat Tracing for Test Manifold (EZ Zone Watlow Controllers, TCs, Heater Tape, and Insulation).

The clean dry air gas pressure was maintained at 25 psig with the pressure regulator. A 0.01 micron filter removed particulates from the gas stream. The mass flow controllers (MFCs) controlled the flow of the carrier gas streams and the dilution gas stream. The relative humidity system (RHS) was used to add water gas to the gas stream. The SGD was used to add hydrogen peroxide and water to the gas stream. The SGD operates in accordance with FIG. 2B. The water temperature was used to control the output of the humidifier. The valves (V-1, V-2, and V-3) were used to send either the dry CDA gas stream, the RHS gas stream, and/or SGD gas stream through the quartz furnace or out to vent. Thermocouple 1 (TC-1) was used to measure the temperature of the dry CDA gas stream. Thermocouple 2 (TC-2) was used to measure gas temperature downstream of the RHS. Thermocouple 3 (TC-3) and thermocouple 4 (TC-4) were used to measure the gas temperature downstream of the SGD. The furnace was used to keep the bacterial samples at temperature to prevent condensation. Thermocouple 5 (TC-5) was used to measure the temperature in the furnace. Thermocouple 6 (TC-6) was used to measure the gas temperature downstream of the furnace. A pressure gauge (PG-1) was used to monitor the pressure in the quartz furnace. Two scrubbers were used to decompose the hydrogen peroxide. The boxed sections show the individual heat traced control zones for this experiment. The control zones are as follows:
Zone 1=SGD Outlet
Zone 2=CDA Dilution Gas
Zone 3=RHS Outlet
Zone 4=Quartz Furnace Inlet
Zone 5=Quartz Furnace Outlet
Zone 6=Quartz Furnace Vent
Zone 7=SGD and RHS Vent Example 17

Bacterial Sample Preparation for Decontamination

The bacterial samples tested were *E. coli, S. epi*, and *S. cerev*. Table 7 is the composition and flow rate of the two gas streams for this experiment. DP represents the dew point. Gas flow is measured in standard liters per minute.

TABLE 7

Bacterial Sterilization Test Gas Parameters

| | H2O2 Conc Before Dilution | H2O Conc Before Dilution | H2O2 Conc After Dilution | H2O Conc After Dilution | Carrier Gas Flow | Dilution Gas Flow | Total Flow |
|---|---|---|---|---|---|---|---|
| Humidified Purge Gas (RHS) | 0 | 55563 (DP = 35 C.) | 0 | 23090 (DP = 20 C.) | 2.1 | 3.2 | 5.4 |
| Peroxide Gas (SVD) | 2305 | 158209 | 509 | 34957 (DP = 26.9) | 1 | 4.2 | 5.4 |

Table 8 represents the bacterial samples used for the individual test runs. Four samples were loaded into the furnace for each test run. The samples were purged with humidified gas for 15 minutes before exposing them to hydrogen peroxide gas for 30 minutes. After the sterilization step, the furnace was purged with humidified gas for 15 minutes before removing from the furnace. The quartz oven and heat-traced zones was heated to maintain the gas stream temperatures ≥25° C. to prevent condensation. Control samples were initially run with just humidified gas to determine if flow rate and/or temperature conditions will kill the bacteria and which did confirm the humidification was not responsible for bacterial death.

TABLE 8

Bacterial Decontamination Test Run Samples - Treatment and Controls

| Treatment or Control Test | Type of Run | # E. Coli Samples | # of S. epi Samples | # of S. cerev Yeast Samples |
|---|---|---|---|---|
| 1 | Control | 2 | 2 | 0 |
| 2 | Treatment | 2 | 2 | 0 |
| 3 | Control | 0 | 0 | 2 |
| 4 | Treatment | 0 | 0 | 2 |

Example 18

Operating Parameters for Decontamination

The SGD was filled with a 31% w/w hydrogen peroxide solution. The initial test manifold was set to the following temperatures:
Zone 1=72° C. (Outlet temperature of SGD)
Zone 3=90° C. (Due to high RHS outlet temperature setting. Gas temperature is above 80 C without heat-tracing).
Zone 2, 4, 5, 6, and oven=25° C.
Zone 7=80° C.
Prior to testing for sterilization, the gas reached the following temperatures to minimize condensation and promote gas stability:
TC-1=90° C.
TC-2=25° C.
TC-3=72° C.
TC-4=25° C.
TC-5=25° C.
TC-6=≥60° C.

The dilution flow gas rate was set to 5.4 slm, the RHS carrier gas to 2.1 slm, and the SGD carrier gas flow to 1 slm. The RHS was then set to a 35° C. dew point and the SGD to 2305 ppm for a 31% solution where both gas streams were run vent. The furnace and the zones were adjusted to achieve the desired gas temperatures and were allowed to stabilize. The humidified gas stream parameters of table 1 were set and to flow through the furnace. Slides containing samples were transferred into the oven and exposed to humidified gas for 50 minutes and removed to determine the effect of humidified gas. New sample slides were then loaded into the furnace and exposed to humidified gas for 10 minutes, then to a peroxide gas stream for 30 minutes, and back to humidified gas for 10 minutes making the necessary gas flow changes. Samples were then removed from the furnace for analysis.

Example 19

Results

Figure 32:
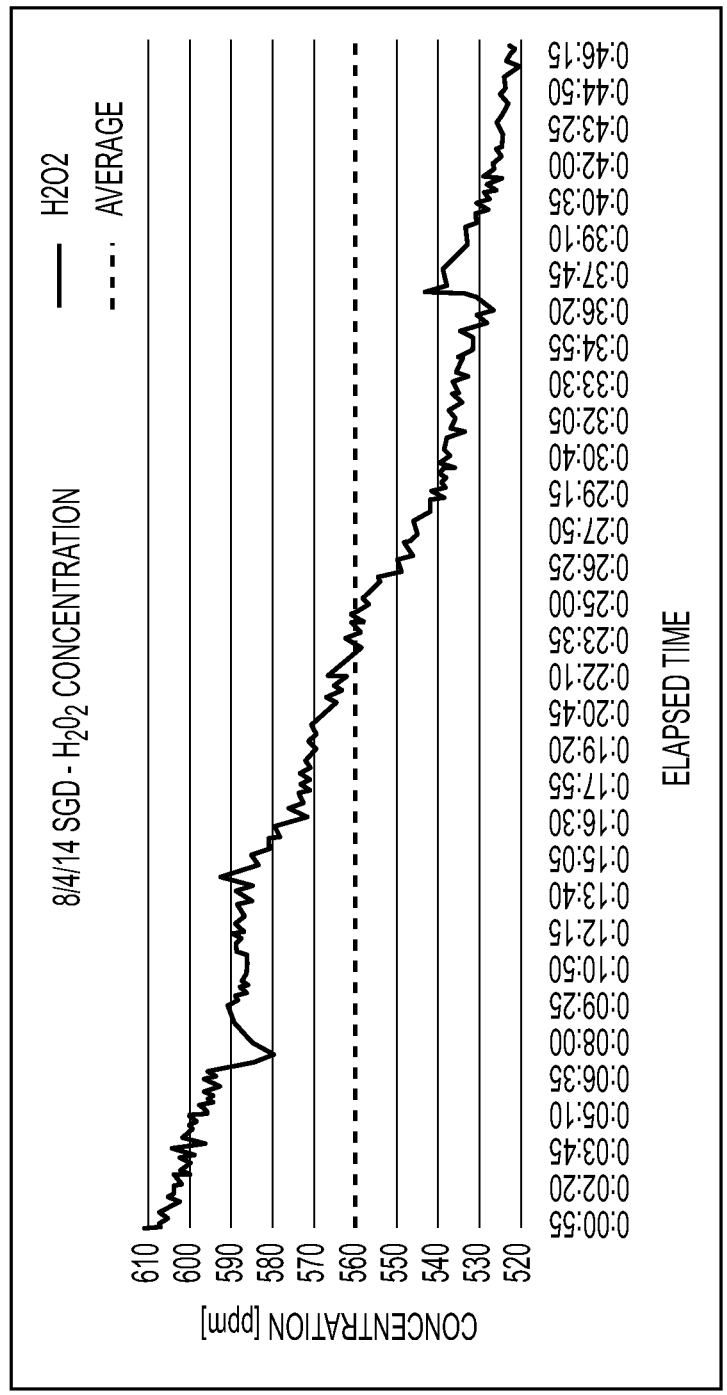
FIG. 32 is the $H_2O_2$ output for Treatment Test 2.
Figure 33:
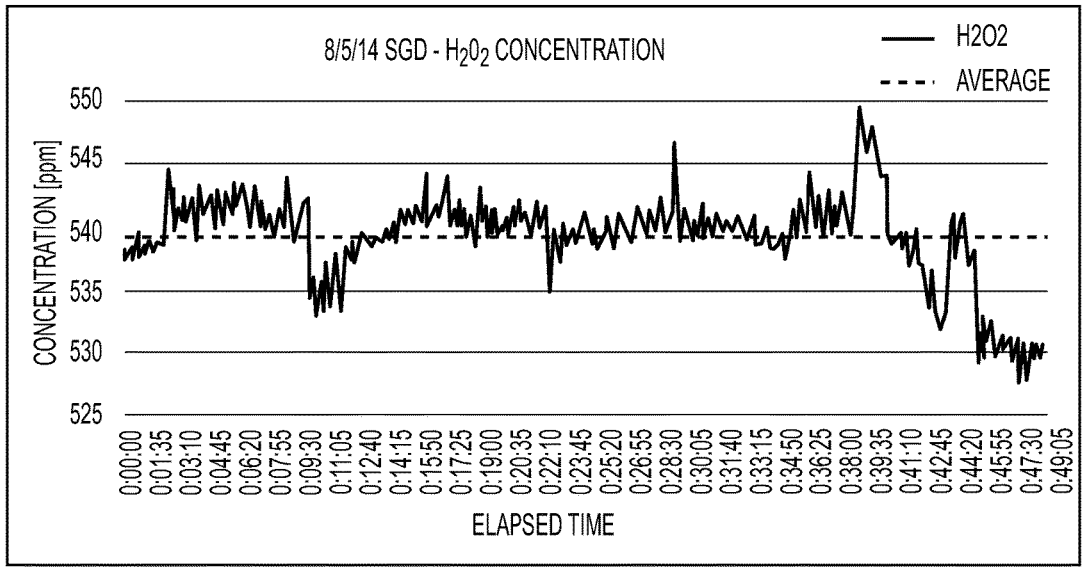
FIG. 33 is the $H_2O_2$ output for Treatment Test 4.
Figure 34:
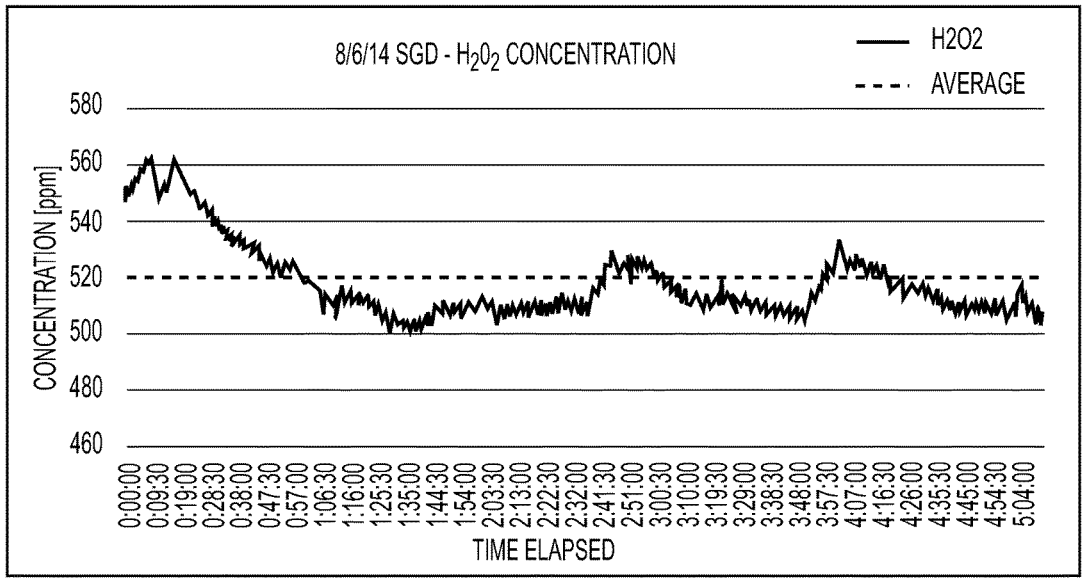
FIG. 34 is the $H_2O_2$ output for Treatment Test 5.

FIGS. 32, 33, and 34 are the SGD's theoretical $H_2O_2$ outputs, based off of temperature and Raoult's law, for Treatment Test Runs 2, 4, and 5 respectively. The average $H_2O_2$ output for Treatment Test Runs 2 and 4 were 561±27 ppm and 539±3 ppm (to within one standard deviation during the length of the experiment). Table 9 represents the results from the control and treatment test runs for the E. coli and S. epi.

For tests associated with FIGS. 32 and 33, only the E. coli was completely sterilized under these conditions. Inadvertent contamination after treatment occurred with all of the S. cerev samples, rendering the results from this portion of the experiment unusable. It is also believed that contamination occurred in the S. epi samples. To test this hypothesis, a fifth experiment was performed (see FIG. 34 for the hydrogen peroxide stability during this experiment) with a 5 hour $H_2O_2$ exposure step. The average $H_2O_2$ output was 518±14 ppm. Table 10 represents the results from this test run. As shown, the S. epi was sterilized.

TABLE 9

| SAMPLE | CONCENTRATION |
|---|---|
| E. coli stock | $2.5 \times 10^7$ |
| E. coli manually air dried & resuspended | $3.2 \times 10^7$ |
| E. coli in device with no $H_2O_2$ | $5.9 \times 10^6$ |
| E. coli in device with $H_2O_2$ | NO GROWTH |
| S. epi stock | $5.0 \times 10^6$ |
| S. epi manually air dried & resuspended | $3.0 \times 10^6$ |
| S. epi in device with no $H_2O_2$ | $1.3 \times 10^6$ |
| S. epi in device with $H_2O_2$ | ~$10^4$ to $10^5$ estimated |

TABLE 10

| SAMPLE | CONCENTRATION |
|---|---|
| S. epi stock | $3.5 \times 10^6$ |
| S. epi in device with $H_2O_2$ | NO GROWTH |

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method for delivering a gas to a critical process application, comprising:
   (a) providing a gas phase of an multicomponent liquid, wherein the multicomponent liquid comprises a first component and a second component which is less volatile than the first component, and wherein the less volatile component is present at an initial concentration;
   (b) contacting the gas phase of the multicomponent liquid with a carrier gas to form a mixed gas stream, whereby the concentration of the less volatile component in the multicomponent liquid increases to a second concentration that is higher than the initial concentration;
   (c) adding to the multicomponent liquid, while step (b) is occurring, a multicomponent liquid comprising the second component at a third concentration that is lower than the second concentration;
   (d) withdrawing, after step (c) has begun, the mixed gas stream comprising a stable steady-state concentration of the less volatile component; and
   (e) delivering the mixed gas stream to a critical process application.

2. The method of claim 1, wherein the gas phase and the multicomponent liquid are separated by a substantially gas-impermeable membrane.

3. The method of claim 2, wherein the membrane is a fluorinated ion-exchange membrane in an acid form.

4. The method of claim 2, wherein critical process application is positioned in a vented chamber configured to permit continuous flow of the mixed gas stream delivered in step (e).

5. The method of claim 2, wherein the substantially gas-impermeable membrane is a salt of a fluorinated ion-exchange membrane.

6. The method of claim 1, wherein the multicomponent liquid is aqueous hydrogen peroxide.

7. The method of claim 6, wherein the initial concentration of hydrogen peroxide in the aqueous hydrogen peroxide liquid provided in step (a) is between about 20% and about 50%.

8. The method of claim 7, wherein the third concentration is the same as the initial concentration of hydrogen peroxide in the aqueous hydrogen peroxide liquid.

9. The method of claim 6, wherein the stable steady-state concentration of hydrogen peroxide in the mixed gas stream is between about 500 ppm and about 300,000 ppm.

10. The method of claim 9, wherein the stable steady-state concentration of hydrogen peroxide is between about 500 ppm and about 800 ppm.

11. The method of claim 6, wherein the concentration of hydrogen peroxide in the mixed gas stream is between about 500 ppm and 15,000 ppm.

12. The method of claim 1, wherein the carrier gas is a substantially dry carrier gas.

13. The method of claim 12, wherein the carrier gas is selected from the group consisting of nitrogen, argon, hydrogen, oxygen, $CO_2$, clean dry air, helium, and any combination thereof.

14. The method of claim 1, further comprising heating the mixed gas stream to between about 20° C. to 120° C. prior to delivering.

15. The method of claim 1, wherein the multicomponent liquid being added in step (c) has a molar ratio that is equal to the molar ratio of the second component to the first component in the mixed gas stream.

16. A method for delivering a gas to a critical process application, comprising:
(a) providing a gas phase of a multi-component liquid, wherein the multi-component liquid comprises water and a component less volatile than water, wherein the component less volatile than water has an initial concentration;
(b) contacting a carrier gas with the gas phase of a multi-component liquid to form a mixed gas stream, wherein the carrier gas is undersaturated with respect to water, whereby the concentration of the component less volatile than water in the multicomponent liquid increases to a second concentration;
(c) adding water to the carrier gas to maintain a constant ratio of components in the multi-component liquid at the second concentration;
(d) replenishing the multi-component liquid with a multi-component liquid comprising the component less volatile than water at a third concentration that is lower than the second concentration to maintain a relatively constant volume of the multi-component liquid; and
(e) delivering the mixed gas stream to a critical process application.

17. The method of claim 16, wherein the multicomponent liquid is aqueous hydrogen peroxide.

18. The method of claim 17, wherein the critical process application is positioned in a vented chamber configured to permit continuous flow of the mixed gas stream delivered in step (e).

19. A delivery device for a critical process application, comprising:
(a) a multicomponent liquid source and a gas phase provided by the multicomponent liquid source, wherein the multicomponent liquid source comprises a first component and a second component which is less volatile than the first component, wherein the less volatile component is at an initial concentration, and wherein the gas phase comprises both components;
(b) a carrier gas in fluid contact with the gas phase, whereby a mixed gas stream is formed comprising the less volatile component, where the concentration of the less volatile component in the multicomponent liquid source increases to a second concentration that is higher than the initial concentration;
(c) a fill tube that replenishes the multicomponent liquid source using a replenishment solution comprising the less volatile component at a third concentration that is lower than the second concentration; and
(d) an apparatus that delivers the mixed gas stream to the critical process application, wherein the delivered mixed gas stream comprises the less volatile component at a stable steady-state concentration.

20. The delivery device of claim 19, wherein the gas phase is separated from the liquid source by a substantially gas-impermeable membrane.

21. The delivery device of claim 20, further comprising an assembly whereby the carrier gas is delivered to the gas phase so that the gas phase is continuously removed to form the gas stream.

22. The delivery device of claim 20, wherein the device comprises an outlet of a head space containing the gas phase, and wherein the outlet leads to the critical process application so that the mixed gas stream flows from the head space to the critical process application.

23. The delivery device of claim 20, wherein the substantially gas-impermeable membrane is a fluorinated ion-exchange membrane in an acid form.

24. The delivery device of claim 20, wherein the substantially gas-impermeable membrane is a salt of a fluorinated ion-exchange membrane.

25. The delivery device of claim 19, wherein the fill tube replenishes the liquid source so that the liquid source maintains a substantially constant volume.

26. The delivery device of claim 19, wherein the multi-component liquid source is aqueous hydrogen peroxide.

27. The delivery device of claim 26, wherein the carrier gas is a substantially dry carrier gas.

* * * * *